United States Patent
Nokura et al.

(10) Patent No.: US 9,120,792 B2
(45) Date of Patent: Sep. 1, 2015

(54) FUSED HETEROCYCLIC COMPOUND

(71) Applicant: Sumitomo Chemical Company, Limited, Tokyo (JP)

(72) Inventors: Yoshihiko Nokura, Takarazuka (JP); Mai Ito, Takarazuka (JP); Chie Shimizu, Takarazuka (JP); Hajime Mizuno, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/403,224

(22) PCT Filed: May 23, 2013

(86) PCT No.: PCT/JP2013/064962
§ 371 (c)(1),
(2) Date: Nov. 24, 2014

(87) PCT Pub. No.: WO2013/180193
PCT Pub. Date: Dec. 5, 2013

(65) Prior Publication Data
US 2015/0094329 A1  Apr. 2, 2015

(30) Foreign Application Priority Data
May 31, 2012  (JP) .................... 2012-124678

(51) Int. Cl.
*C07D 471/04* (2006.01)
*A01N 43/76* (2006.01)
(Continued)

(52) U.S. Cl.
CPC .............. *C07D 471/04* (2013.01); *A01N 43/76* (2013.01); *A01N 43/78* (2013.01); *A01N 43/90* (2013.01);
(Continued)

(58) Field of Classification Search
None
See application file for complete search history.

(56) References Cited

U.S. PATENT DOCUMENTS

2004/0048868 A1  3/2004  Edwards et al.
2006/0014756 A1  1/2006  Edwards et al.
(Continued)

FOREIGN PATENT DOCUMENTS

JP  2000-001481 A  1/2000
JP  2011-219420 A  11/2011
(Continued)

OTHER PUBLICATIONS

U.S. Appl. No. 14/403,021 by Takahashi, filed Nov. 21, 2014.
(Continued)

Primary Examiner — Janet L Andres
Assistant Examiner — Timothy R Rozof
(74) Attorney, Agent, or Firm — Panitch Schwarze Belisario & Nadel LLP

(57) ABSTRACT

A compound represented by formula (1) and an N-oxide thereof have excellent pest control effect. (In the formula, Het to which $R^1$—$S(O)_n$ is bonded represents a five-membered aromatic heterocyclic ring represented by formula H1, H2, H3 or H4 (wherein $Y^1$ represents an oxygen atom or the like; $Y^2$ represents an oxygen atom or the like; $G^1$, $G^2$ and $G^3$ may be the same or different and each represents a nitrogen atom or the like; $R^1$ represents a $C_1$-$C_6$ alkyl group which may have one or more atoms or groups selected from the group X, or the like; and n represents 0, 1 or 2); $A^1$ represents an oxygen atom or the like; $A^2$ represents a nitrogen atom or the like; $A^3$ represents a nitrogen atom or the like; and $R^2$ and $R^3$ may be the same or different and each represents a $C_1$-$C_6$ chain hydrocarbon group which may have one or more atoms or groups selected from the group X, or the like.).

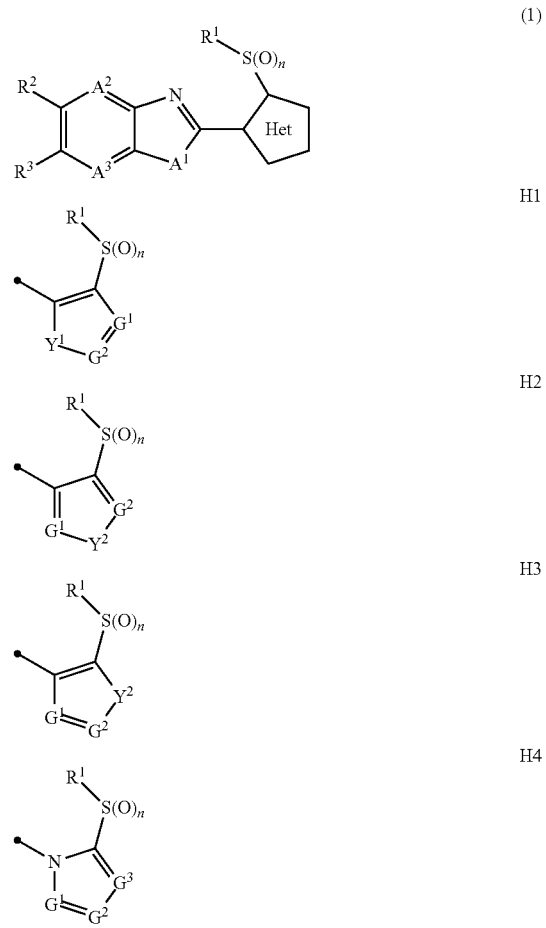

17 Claims, No Drawings

(51) Int. Cl.
*A01N 43/78* (2006.01)
*A01N 43/90* (2006.01)
*C07D 409/12* (2006.01)
*C07D 413/04* (2006.01)
*C07D 417/04* (2006.01)
*C07D 417/12* (2006.01)
*C07D 513/04* (2006.01)
*C07D 401/04* (2006.01)
*C07D 403/04* (2006.01)

(52) U.S. Cl.
CPC ............ *C07D 401/04* (2013.01); *C07D 403/04* (2013.01); *C07D 409/12* (2013.01); *C07D 413/04* (2013.01); *C07D 417/04* (2013.01); *C07D 417/12* (2013.01); *C07D 513/04* (2013.01)

(56) References Cited

U.S. PATENT DOCUMENTS

2011/0039843 A1  2/2011  Iwakoshi et al.
2012/0015975 A1  1/2012  Takahashi et al.
2012/0108586 A1  5/2012  Iwakoshi et al.
2012/0178779 A1  7/2012  Takahashi et al.
2012/0196891 A1  8/2012  Iwakoshi
2012/0245167 A1  9/2012  Iwakoshi et al.
2014/0018373 A1  1/2014  Takyo et al.
2014/0194290 A1  7/2014  Takahashi et al.

FOREIGN PATENT DOCUMENTS

WO  9952882 A1  10/1999
WO  0107413 A1  2/2001

OTHER PUBLICATIONS

Amareshwar et al, "2-Phenyl-4-bis(methylthio)methyleneoxazol-5-one: versatile template for diversity oriented synthesis of heterocycles," Org. Biomol. Chem., vol. 9, No. 16, pp. 5793-5801 (2011).
Int'l Search Report issued Jun. 25, 2013 in Int'l Application No. PCT/JP2013/064962.

FUSED HETEROCYCLIC COMPOUND

CROSS-REFERENCE TO RELATED APPLICATION

This application is a Section 371 of International Application No. PCT/JP2013/064962, filed May 23, 2013, which was published in the Japanese language on Dec. 5, 2013, under International Publication No. WO 2013/180193 A1, and the disclosure of which is incorporated herein by reference.

TECHNICAL FIELD

The present invention relates to a fused heterocyclic compound and a use thereof for pest control.

BACKGROUND ART

A certain kind of fused heterocyclic compounds is known to have an insecticidal activity (refer to WO 2001/07413 and WO 1999/52882).

However, the insecticidal activity of these fused heterocyclic compounds is not necessarily sufficient.

SUMMARY OF THE INVENTION

The present invention provides a compound having an excellent effect in the control of pests.

More specifically, the present invention is as described below.

[1]
A compound represented by formula (1) or an N-oxide thereof, (1)

wherein
Het to which $R^1$—$S(O)_n$ is bonded represents a 5-membered aromatic heterocyclic group represented by the following formula H1, H2, H3 or H4:

H1

H2

H3

H4 wherein
$Y^1$ represents an oxygen atom, a sulfur atom, or $NR^4$;
$Y^2$ represents an oxygen atom, a sulfur atom, or $NR^5$;
$G^1$, $G^2$ and $G^3$ are the same or different and represent $CR^6$ or a nitrogen atom;
$R^1$ represents a C1 to C6 alkyl group optionally having one or more atoms or groups selected from group X, a C2 to C6 alkenyl group optionally having one or more atoms or groups selected from group X, a C1 to C6 alkynyl group optionally having one or more atoms or groups selected from group X, or a C3 to C6 alicyclic hydrocarbon group optionally having one or more atoms or groups selected from group Y;
$R^4$ and $R^6$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^7$, $S(O)_mR^7$, $S(O)_2NR^7R^8$, $NR^7R^8$, $NR^7CO_2R^8$, $NR^7C(O)R^8$, $CO_2R^7$, $C(O)R^8$, $C(O)NR^7R^8$, $SF_5$, a cyano group, a nitro group, a halogen atom, or a hydrogen atom;
$R^5$ represents a C1 to C6 chain hydrocarbon group optionally having one or more atoms or groups selected from group X, a 5- or 6-membered heterocyclic group optionally having one or more atoms or groups selected from group Z, $OR^{12}$, $S(O)_pR^{12}$, $S(O)_2NR^{12}R^{13}$, $NR^{12}R^{13}$, $NR^{12}CO_2R^{13}$, $NR^{12}C(O)R^{13}$, $CO_2R^{12}$, $C(O)R^{12}$, $C(O)NR^{12}R^{13}$, $SF_5$, a cyano group, a nitro group, a halogen atom, or a hydrogen atom;
$R^7$, $R^8$, $R^{12}$ and $R^{13}$ are the same or different and represent a C1 to C6 chain hydrocarbon group optionally having one or more atoms or groups selected from group X, or a hydrogen atom;
each m independently represents 0, 1, or 2;
n represents 0, 1, or 2; and
each p independently represents 0, 1, or 2;
wherein, when m is 1 or 2 in $S(O)_mR^7$, $R^7$ does not represent a hydrogen atom, and when p is 1 or 2 in $S(O)_pR^{12}$, $R^{12}$ does not represent a hydrogen atom,
$A^1$ represents an oxygen atom, a sulfur atom, or $NR^9$;
$A^2$ represents a nitrogen atom or $CR^{10}$;
$A^3$ represents a nitrogen atom or $CR^{11}$;
$R^2$ and $R^3$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^{14}$, $S(O)_qR^{14}$, $S(O)_2NR^{14}R^{15}$, $NR^{14}R^{15}$, $NR^{14}CO_2R^{15}$, $NR^{14}C(O)R^{15}$, $CO_2R^{14}$, $C(O)R^{15}$, $SF_5$, a cyano group, a nitro group, a halogen atom, or a hydrogen atom;

$R^9$ represents a C1 to C6 chain hydrocarbon group optionally having one or more atoms or groups selected from group X, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $CO_2R^{16}$, $C(O)R^{16}$, a C3 to C6 alicyclic hydrocarbon group optionally having one or more atoms or groups selected from group Y, or a hydrogen atom;

$R^{10}$ and $R^{11}$ are the same or different and represent a C1 to C6 chain hydrocarbon group optionally having one or more halogen atoms, $OR^{17}$, $S(O)_rR^{17}$, $NR^{17}R^{18}$, $CO_2R^{17}$, $C(O)R^{17}$, a cyano group, a nitro group, $SF_5$, a halogen atom, or a hydrogen atom;

$R^{14}$, $R^{15}$, $R^{16}$, $R^{17}$ and $R^{18}$ are the same or different and represent a C1 to C6 chain hydrocarbon group optionally having one or more atoms or groups selected from group X, or a hydrogen atom;

each q independently represents 0, 1, or 2; and each r independently represents 0, 1, or 2;

wherein $R^2$ and $R^3$ do not simultaneously represent a hydrogen atom;

when q is 1 or 2 in $S(O)_qR^{14}$, $R^{14}$ does not represent a hydrogen atom; and when r is 1 or 2 in $S(O)_rR^{17}$, $R^{17}$ does not represent a hydrogen atom.

Group X: a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, $C_3$ to $C_6$ cycloalkyl groups optionally having one or more halogen atoms or one or more C1 to C3 alkyl groups, cyano groups, hydroxy groups, and halogen atoms.

Group Y: a group consisting of C1 to C6 chain hydrocarbon groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, and halogen atoms.

Group Z: a group consisting of C1 to C6 chain hydrocarbon groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C1 to C6 alkylamino groups optionally having one or more halogen atoms, C2 to C8 dialkylamino groups optionally having one or more halogen atoms, halogen atoms, amino groups, cyano groups, $SF_5$, and nitro groups.

[2]

The compound according to [1], wherein $R^1$ is a C1 to C6 alkyl group optionally having one or more atoms or groups selected from group X or a C3 to C6 alicyclic hydrocarbon group optionally having one or more atoms or groups selected from group Y;

$R^2$ and $R^3$ are the same or different and are a C1 to C6 chain hydrocarbon group optionally having one or more atoms or groups selected from group X, $OR^{14}$, $S(O)_qR^{14}$, $SF_5$, a cyano group, a halogen atom, or a hydrogen atom;

$R^4$ and $R^6$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^7$, $S(O)_mR^7$, $SF_5$, a cyano group, a halogen atom, or a hydrogen atom;

$R^5$ is a C1 to C6 chain hydrocarbon group optionally having one or more atoms or groups selected from group X, a 5- or 6-membered heterocyclic group optionally having one or more atoms or groups selected from group Z, $OR^{12}$, $S(O)_p R^{12}$, $SF_5$, a cyano group, a halogen atom, or a hydrogen atom;

$R^9$ is a C1 to C6 chain hydrocarbon group optionally having one or more atoms or groups selected from group X, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), or a C3 to C6 alicyclic hydrocarbon group optionally having one or more atoms or groups selected from group Y;

$R^{10}$ and $R^{11}$ are the same or different and are a C1 to C6 chain hydrocarbon group optionally having one or more halogen atoms, $OR^{17}$, $S(O)_rR^{17}$, $SF_5$, a halogen atom, or a hydrogen atom; and $R^7$, $R^{12}$, $R^{14}$ and $R^{17}$ are the same or different and are a C1 to C6 chain hydrocarbon group optionally having one or more atoms or groups selected from group X.

[3]

The compound according to [1] or [2], wherein $R^1$ is a C2 to C6 alkyl group optionally having one or more atoms or groups selected from halogen atoms and a cyclopropyl group (wherein the cyclopropyl group optionally has one or more halogen atoms or one or more C1 to C3 alkyl groups);

$R^2$ is a C1 to C6 alkyl group optionally having one or more halogen atoms, $OR^{14}$, $S(O)_qR^{14}$, $SF_5$, or a halogen atom;

$R^3$ is a hydrogen atom; and $R^{10}$ is a hydrogen atom.

[4]

The compound according to any one of [1] to [3], wherein $R^9$ is a C1 to C6 alkyl group optionally having one or more halogen atoms.

[5]

The compound according to any one of [1] to [4], wherein $A^2$ is CH;

$A^3$ is a nitrogen atom; and $R^3$ is a hydrogen atom.

[6]

The compound according to any one of [1] to [5], wherein $R^4$ and $R^6$ are the same or different and are a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, $OR^7$, $S(O)_m R^7$, $SF_5$, a cyano group, a halogen atom, or a hydrogen atom.

[7]

The compound according to any one of [1] to [5], wherein Het to which $R^1$—$S(O)_n$ is bonded is H1;

$G^1$ and $G^2$ are the same or different and are $CR^6$; and $R^6$ is a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, or a hydrogen atom.

[8]

The compound according to any one of [1] to [5] and [7], wherein Het to which $R^1$—$S(O)_n$ is bonded is H1;

$G^1$ is CH; and $G^2$ is $CR^6$, and $CR^6$ is a C1 to C6 alkyl group optionally having one or more halogen atoms or a hydrogen atom.

[9]

The compound according to any one of [1] to [5], wherein Het to which $R^1$—$S(O)_n$ is bonded is H2;

$Y^2$ is an oxygen atom or a sulfur atom;

$G^1$ is a nitrogen atom;

$G^2$ is $CR^6$; and $R^6$ is a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, or a hydrogen atom.

[10]

The compound according to any one of [1] to [5], wherein Het to which $R^1$—$S(O)_n$ is bonded is H3;

$G^1$ is a nitrogen atom;

$Y^2$ is an oxygen atom or a sulfur atom;

$G^2$ is $CR^6$; and $R^6$ is a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, or a hydrogen atom.

[11]

The compound according to any one of [1] to [5] and [10], wherein Het to which $R^1$—$S(O)_n$ is bonded is H3;

$G^1$ is a nitrogen atom;

$Y^2$ is a sulfur atom; and $G^2$ is $CR^6$, and $CR^6$ is a C1 to C6 alkyl group optionally having one or more halogen atoms, or a hydrogen atom.

[12]

The compound according to any one of [1] to [5], wherein Het to which $R^1$—$S(O)_n$ is bonded is H4;

$G^2$ and $G^3$ are the same or different and are $CR^6$; and $R^6$ is a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, or a hydrogen atom.

[13]

The compound according to any one of [1] to [1,2], wherein $A^2$ is $CR^{10}$; and $R^6$ is a hydrogen atom.

[14]
A compound represented by formula (2-2)

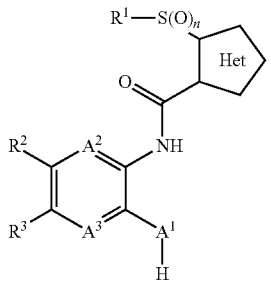

wherein
Het to which R¹—S(O)ₙ is bonded represents a 5-membered aromatic heterocyclic group represented by the following formula H1, H2, H3 or H4:

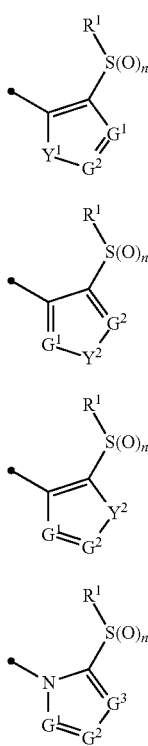

wherein R¹, Y¹, Y², G¹, G², G³ and n represent the same meaning as those above, A¹, A², A³, R² and R³ represent the same meaning as those above
or an N-oxide thereof.

[15]
The compound according to [14],
wherein R¹ represents a C2 to C6 alkyl group optionally having one or more atoms or groups selected from halogen atoms and a cyclopropyl group (wherein the cyclopropyl group optionally has one or more halogen atoms or one or more C1 to C3 alkyl groups);
R⁴ and R⁶ are the same or different and represent a phenyl group (wherein the phenyl group optionally has one or more atoms or groups selected from C1 to C3 alkyl groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, halogen atoms and SF₅), a 5- or 6-membered heterocyclic group (wherein the 5- or 6-membered heterocyclic group optionally has one or more atoms or groups selected from C1 to C3 alkyl groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, halogen atoms and SF₅), or a C1 to C6 alkyl group optionally having one or more halogen atoms;
R⁵ represents a 5- or 6-membered heterocyclic group (wherein the 5- or 6-membered heterocyclic group optionally has one or more atoms or groups selected from C1 to C3 alkyl groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, halogen atoms and SF₅) or a C1 to C6 alkyl group optionally having one or more halogen atoms;
$A^2$ represents CH;
$R^2$ and $R^{11}$ are the same or different and represent a C1 to C6 alkyl group optionally having one or more halogen atoms, $OR^{14}$, $S(O)_qR^{14}$, $SF_5$, or a halogen atom;
$R^9$ and $R^{14}$ are the same or different and represent a C1 to C6 alkyl group optionally having one or more halogen atoms;
and
$R^3$ represents a hydrogen atom;
wherein, when q is 1 or 2 in $S(O)_qR^{14}$, $R^{14}$ does not represent a hydrogen atom.

[16]
A pest control agent comprising the compound as defined in any of [1] to [13], and an inert carrier.

[17]
A use of the compound as defined in any of [1] to [13] for controlling pests.

[18]
A method for controlling pests comprising a step of applying an effective amount of the compound as defined in any of [1] to [13] to a pest or pest habitats.

MODE FOR CARRYING OUT THE INVENTION

In the compound of the present invention, an N-oxide is a compound in which the nitrogen atom constituting the ring on the heterocyclic group is oxidized. Examples of the heterocyclic group that may form an N-oxide include a pyridine ring and fused rings containing a pyridine ring.

The terms used in the present specification will be described below with examples.

The notation of "Ca to Cb chain hydrocarbon group" in the present specification represents a straight or branched saturated or unsaturated hydrocarbon group having the number of carbon atoms of a to b.

Examples of the "C1 to C6 chain hydrocarbon group" include C1 to C6 alkyl groups such as a methyl group, an ethyl group, a propyl group, an isopropyl group, a butyl group, an isobutyl group, a sec-butyl group, a tert-butyl group, a pentyl group, a neopentyl group and a hexyl group; C2 to C6 alkenyl groups such as a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group and a 1-hexenyl group; and C2 to C6 alkynyl groups such as an ethynyl group, a propargyl group, a 2-butynyl group, a 3-butynyl group, a 1-pentynyl group and a 1-hexynyl group.

The notation of "Ca to Cb alkyl group" in the present specification represents a straight or branched chain hydrocarbon group having the number of carbon atoms of a to b.

Examples of the "C1 to C6 alkyl group" include a methyl group, an ethyl group, a propyl group, an isopropyl group, a butyl group, an isobutyl group, a sec-butyl group, a tert-butyl group, a pentyl group, a neopentyl group, and a hexyl group.

Examples of the "C2 to C6 alkyl group" include an ethyl group, a propyl group, an isopropyl group, a butyl group, an isobutyl group, a sec-butyl group, a tert-butyl group, a pentyl group, a neopentyl group, and a hexyl group.

Examples of the "C1 to C3 alkyl group" include a methyl group, an ethyl group, a propyl group, and an isopropyl group.

The notation of "Ca to Cb alkenyl group" in the present specification represents a straight or branched chain unsaturated hydrocarbon group having the number of carbon atoms of a to b, and having one or two or more double bonds in the molecule.

Examples of the "C2 to C6 alkenyl group" include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, and a 1-hexenyl group.

The notation of "Ca to Cb alkynyl group" in the present specification represents a straight or branched unsaturated hydrocarbon group having the number of carbon atoms of a to b, and having one or two or more triple bonds in the molecule.

Examples of the "C2 to C6 alkynyl group" include an ethynyl group, a propargyl group, a 2-butynyl group, a 3-butynyl group, a 1-pentynyl group, and a 1-hexynyl group.

The notation of "Ca to Cb haloalkyl group" in the present specification represents a straight or branched hydrocarbon group having the number of carbon atoms of a to b, in which one or more hydrogen atoms bound to the carbon atom are substituted by a halogen atom, and at that time, when having two or more halogen atoms, those halogen atoms may be the same or different from each other.

Examples of the "C1 to C6 haloalkyl group" include a fluoromethyl group, a chloromethyl group, a bromomethyl group, an iodomethyl group, a difluoromethyl group, a dichloromethyl group, a trifluoromethyl group, a chlorodifluoromethyl group, a bromodifluoromethyl group, a trichloromethyl group, a 2-fluoroethyl group, a 2-chloroethyl group, a 2-bromoethyl group, a 2,2-difluoroethyl group, a 2,2,2-trifluoroethyl group, a pentafluoroethyl group, a heptafluoropropyl group, and a heptafluoroisopropyl group.

Examples of the "C1 to C3 haloalkyl group" include groups exemplified in the "C1 to C6 haloalkyl group" described above.

The "C1 to C6 perfluoroalkyl group" represents a straight or branched hydrocarbon group having the number of carbon atoms of 1 to 6, in which all hydrogen atoms bound to the carbon atom are substituted by a fluorine atom, and includes a trifluoromethyl group, a pentafluoroethyl group, a heptafluoropropyl group, and a heptafluoroisopropyl group.

The notation of "Ca to Cb alkoxy group" in the present specification represents a straight or branched group represented by alkyl-O— having the number of carbon atoms of a to b.

Examples of the "C1 to C6 alkoxy group" include a methoxy group, an ethoxy group, a propoxy group, an isopropoxy group, a butoxy group, an isobutoxy group, a sec-butoxy group, a tert-butoxy group, a pentyloxy group, a neopentyloxy group, and a hexyloxy group.

Examples of the "C1 to C3 alkoxy group" include a methoxy group, an ethoxy group, a propoxy group, and an isopropoxy group.

The notation of "Ca to Cb alkenyloxy group" in the present specification represents a straight or branched group represented by alkenyl-O— having the number of carbon atoms of a to b, and having one or two or more double bonds in the molecule.

Examples of the "C2 to C6 alkenyloxy group" include a vinyloxy group, a 1-propenyloxy group, a 2-propenyloxy group, a 1-methylvinyloxy group, a 2-methyl-1-propenyloxy group, a 1-butenyloxy group, a 2-butenyloxy group, a 3-butenyloxy group, a 1-pentenyloxy group, and a 1-hexenyloxy group.

The notation of "Ca to Cb alkynyloxy group" in the present specification represents a straight or branched group represented by alkynyl-O— having the number of carbon atoms of a to b, and having one or two or more triple bonds in the molecule.

Examples of the "C2 to C6 alkynyloxy group" include an ethynyloxy group, a propargyloxy group, a 2-butynyloxy group, a 3-butynyloxy group, a 1-pentynyloxy group, and a 1-hexynyloxy group.

The notation of "Ca to Cb alkylthio group" in the present specification represents a straight or branched group represented by alkyl-S— having the number of carbon atoms of a to b.

Examples of the "C1 to C6 alkylthio group" include a methylthio group, an ethylthio group, a propylthio group, an isopropylthio group, a butylthio group, a pentylthio group, and a hexylthio group.

Examples of the "C1 to C3 alkylthio group" include a methylthio group, an ethylthio group, a propylthio group, and a isopropylthio group.

The notation of "Ca to Cb alkylsulfinyl group" in the present specification represents a straight or branched group represented by alkyl-S(O)— having the number of carbon atoms of a to b.

Examples of the "C1 to C6 alkylsulfinyl group" include a methylsulfinyl group, an ethylsulfinyl group, a propylsulfinyl group, an isopropylsulfinyl group, a butylsulfinyl group, a pentylsulfinyl group, and a hexylsulfinyl group.

Examples of the "C1 to C3 alkylsulfinyl group" include a methylsulfinyl group, an ethylsulfinyl group, a propylsulfinyl group, and an isopropylsulfinyl group.

The notation of "Ca to Cb alkylsulfonyl group" in the present specification represents a straight or branched group represented by alkyl-S(O)$_2$— having the number of carbon atoms of a to b.

Examples of the "C1 to C6 alkylsulfonyl group" include a methylsulfonyl group, an ethylsulfonyl group, a propylsulfonyl group, an isopropylsulfonyl group, a butylsulfonyl group, a pentylsulfonyl group, and a hexylsulfonyl group.

Examples of the "C1 to C3 alkylsulfonyl group" include a methylsulfonyl group, an ethylsulfonyl group, a propylsulfonyl group, and an isopropylsulfonyl group.

The notation of "Ca to Cb alkylcarbonyl group" in the present specification represents a group represented by a straight or branched alkyl-C(O)— having the number of carbon atoms of a to b.

Examples of the "C2 to C6 alkylcarbonyl group" include an acetyl group, a propionyl group, a butyryl group, a pentanoyl group, and a hexanoyl group.

The notation of "Ca to Cb alkoxycarbonyl group" in the present specification represents a straight or branched group represented by alkyl-O—C(O)— having the number of carbon atoms of a to b.

Examples of the "C2 to C6 alkoxycarbonyl group" include a methoxycarbonyl group, an ethoxycarbonyl group, a propoxycarbonyl group, a butoxycarbonyl group, a pentyloxycarbonyl group, and a tert-butoxycarbonyl group.

The notation of "Ca to Cb alicyclic hydrocarbon group" in the present specification represents a cyclic nonaromatic hydrocarbon group having the number of carbon atoms of a to b.

Examples of the "C3 to C6 alicyclic hydrocarbon group" include a cyclopropyl group, a cyclobutyl group, a cyclopentyl group, a cyclohexyl group, a 1-cyclohexenyl group, a 2-cyclohexenyl group, and a 3-cyclohexenyl group.

The notation of "Ca to Cb cycloalkyl group" in the present specification represents a cyclic alkyl group having the number of carbon atoms of a to b.

The "C3 to C6 cycloalkyl group" includes a cyclopropyl group, a cyclobutyl group, a cyclopentyl group, and a cyclohexyl group.

The notation of "Ca to Cb alkylamino group" in the present specification represents a straight or branched group represented by alkyl-NH— having the number of carbon atoms of a to b.

Examples of the "C1 to C6 alkylamino group" include a methylamino group, an ethylamino group, a propylamino group, an isopropylamino group, and a butylamino group.

The notation of "Ca to Cb dialkylamino group" in the present specification represents a straight or branched dialkylamino group having a total number of carbon atoms of each alkyl group of a to b, in which the total number of each alkyl group may be the same or different.

Examples of the "C2 to C8 dialkylamino group" include a dimethylamino group, a diethylamino group, and a dipropylamino group.

In the notation of "optionally having one or more atoms or groups selected from group X" in the present specification, when having two or more atoms or groups selected from group X, the atoms or groups selected from group X may be the same or different each other.

In the notation of "optionally having one or more atoms or groups selected from group Y" in the present specification, when having two or more atoms or groups selected from group Y, the atoms or groups selected from group Y may be the same or different each other.

In the notation of "optionally having one or more atoms or groups selected from group Z" in the present specification, when having two or more atoms or groups selected from group Z, the atoms or groups selected from group Z may be the same or different each other.

In the notation of "optionally having one or more halogen atoms" in the present specification, when having two or more halogen atoms, those halogen atoms may be the same or different each other.

The notation of "5-membered heterocyclic group" in the present specification represents a 5-membered heterocyclic compound residue containing one or more atoms selected from the group consisting of a nitrogen atom, an oxygen atom and a sulfur atom, other than a carbon atom, and examples include a 5-membered aromatic heterocyclic group, a 5-membered nonaromatic heterocyclic group, and the like.

Examples of the "5-membered aromatic heterocyclic group" include a pyrrolyl group, a furyl group, a pyrazolyl group, a thienyl group, an imidazolyl group, a triazolyl group, a tetrazolyl group, and an isoxazolyl group.

Examples of the "5-membered nonaromatic heterocyclic group" include a pyrrolidinyl group, a pyrazolidinyl group, and a tetrahydrofuryl group.

The notation of "6-membered heterocyclic group" in the present specification represents a 6-membered heterocyclic compound residue containing one or more atoms selected from the group consisting of a nitrogen atom, an oxygen atom and a sulfur atom, other than a carbon atom, in the cyclic structure, and examples include a 6-membered aromatic heterocyclic group and a 6-membered nonaromatic heterocyclic group.

Examples of the "6-membered aromatic heterocyclic group" include a pyrazinyl group, a pyrimidinyl group, and a pyridyl group.

Examples of the "6-membered nonaromatic heterocyclic group" include a piperidyl group, a morpholinyl group, a piperazinyl group, and a thiomorpholinyl group.

The "5- or 6-membered heterocyclic group" in the present specification represents a 5-membered heterocyclic group or 6-membered heterocyclic group, and specifically includes a 5- or 6-membered aromatic heterocyclic group and a 5- or 6-membered nonaromatic heterocyclic group.

The "halogen atom" in the present specification refers to a fluorine atom, a chlorine atom, a bromine atom, and an iodine atom.

In the summary notation of the chemical formula of the compound of the present invention, "sec-" refers to secondary and "tert-" refers to tertiary.

In the compound of the present invention, examples of the "C1 to C6 alkyl group optionally having one or more atoms or groups selected from group X" include a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group, a pentafluoroethyl group, a heptafluoroisopropyl group, a cyanomethyl group, a cyanoethyl group, a methoxymethyl group, an ethoxymethyl group, a 1-methoxyethyl group, a methylthiomethyl group, a methylthioethyl group, a methylsulfinylethyl group, a methylsulfonylethyl group, a methoxycarbonylmethyl group, a methoxycarbonylethyl group, a cyclopropylmethyl group, a (2,2-dichlorocyclopropyl)methyl group, a cyclobutylmethyl group, and a cyclohexylmethyl group.

In the compound of the present invention, examples of the "C1 to C6 alkenyl group optionally having one or more atoms or groups selected from group X" include a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, a pentafluoroallyl group, and a 1,1-dichloroallyl group.

In the compound of the present invention, examples of the "C1 to C6 alkynyl group optionally having one or more atoms or groups selected from group X" include an ethynyl group, a propargyl group, a 2-butynyl group, a 3-butynyl group, a 1-pentynyl group, a 1-hexynyl group, and a 4,4,4-trifluoro-2-butynyl group.

In the compound of the present invention, examples of the "C3 to C6 alicyclic hydrocarbon group optionally having one or more atoms or groups selected from group Y" include a cyclopropyl group, a 1-methylcyclopropyl group, a cyclobutyl group, a cyclopentyl group, a cyclohexyl group, a 1-cyclohexenyl group, a 2-cyclohexenyl group, a 3-cyclohexenyl group, a 1-methylcyclohexyl group, a 2-methylcyclohexyl group, a 3-methylcyclohexyl group, a 4-methylcyclohexyl group, a 2-methoxylcyclohexyl group, a 3-methoxylcyclohexyl group, a 4-methoxylcyclohexyl group, a 1-fluorocyclohexyl group, a 2-fluorocyclohexyl group, a 3-fluorocyclohexyl group, and a 4-fluorocyclohexyl group.

In the compound of the present invention, examples of the "C1 to C6 chain hydrocarbon group optionally having one or more atoms or groups selected from group X" include a methyl group, an ethyl group, a propyl group, an isopropyl group, a butyl group, an isobutyl group, a sec-butyl group, a tert-butyl group, a pentyl group, a neopentyl group, a hexyl group, a methoxymethyl group, an ethoxymethyl group, a propoxymethyl group, an isopropoxymethyl group, a butoxymethyl group, a sec-butoxymethyl group, a tert-butoxymethyl group, a 2-methoxyethyl group, a 2-ethoxyethyl group, a 2-propoxyethyl group, a 2-isopropoxyethyl group, a 2-butoxyethyl group, a 2-sec-butoxyethyl group, a 2-tert-butoxyethyl group, a trifluoromethyl group, a trichloromethyl group, a 2-fluoroethyl group, a 2,2-difluoroethyl group, a 2,2,2-trifluoroethyl group, a pentafluoroethyl group, a heptafluoropropyl group, heptafluoroisopropyl, a methylthioethyl group, an ethylthioethyl group, a methylsulfinylethyl group, a methylsulfonylethyl group, a 2-hydroxyethyl group, a cyclopropylmethyl group, a 2,2-difluorocyclopropylmethyl group, a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, a pentafluoroallyl group, an ethynyl group, a propargyl group, a 2-butynyl group, a 3-butynyl group, a 1-pentynyl group, a 1-hexynyl group, and a 4,4,4-trifluoro-2-butynyl group.

In the compound of the present invention, examples of the "phenyl group optionally having one or more atoms or groups selected from group Z" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, a 4-pentafluoroethylphenyl group, a 4-heptafluoroisopropylphenyl group, a 2-trifluoromethoxyphenyl group, a 3-trifluoromethoxyphenyl group, a 4-trifluoromethoxyphenyl group, a 2-trifluoromethylthiophenyl group, a 3-trifluoromethylsulthiophenyl group, a 4-trifluoromethylthiophenyl group, a 4-trifluoromethylsulfonylphenyl group, a 4-nitrophenyl group, a 4-cyanophenyl group, a 4-methylaminophenyl group, a 4-dimethylaminophenyl group, a 4-methylsulfinylphenyl group, a 4-methylsulfonylphenyl group, a 4-trifluoroacetylphenyl group, a 4-acetylphenyl group, a 4-$F_5S$ phenyl group, and a 4-methoxycarbonylphenyl group.

In the compound of the present invention, examples of the "5-membered heterocyclic group optionally having one or more atoms or groups selected from group Z" include a pyrrolidin-1-yl group, a 2,5-dimethylpyrrolidin-1-yl group, a 3,3,4,4-tetrafluoropyrrolidin-1-yl group, a tetrahydrofuran-2-yl group, a 2-pyrrolyl group, a 2-furyl group, a 3-furyl group, a 4-trifluoromethyl-2-furyl group, a 5-pyrazolyl group, a 4-pyrazolyl group, a 1-pyrrolyl group, a 2-methyl-1-pyrrolyl group, a 2-methylthio-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 4-trifluoromethyl-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, and a 4-trifluoromethylpyrazol-1-yl group.

In the compound of the present invention, examples of the "6-membered heterocyclic group optionally having one or more atoms or groups selected from group Z" include a piperidyl group, a morpholinyl group, a thiomorpholinyl group, a pyrazinyl group, a 4-pyrimidinyl group, a 5-trifluoromethyl-pyrimidin-2-yl group, a 5-pentafluoroethyl-pyrimidin-2-yl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group, and a 5-pentafluoroethylpyridin-2-yl group.

In the compound of the present invention, examples of the "C1 to C6 chain hydrocarbon group having one phenyl group (wherein the phenyl group may have one or more atoms or groups selected from group Z)" include a phenylmethyl group, a 4-chlorophenylmethyl group, and a 4-trifluoromethylphenylmethyl group.

In the compound of the present invention, examples of the "C1 to C6 chain hydrocarbon group having one 5- or 6-membered heterocyclic group (wherein the 5- or 6-membered heterocyclic group may have one or more atoms or groups selected from group Z)" include a tetrahydrofuran-2-ylmethyl group, a thiozol-5-ylmethyl group, a 2-chlorothiozol-5-ylmethyl group, a tetrahydropyran-2-ylmethyl group, a tetrahydropyran-3-ylmethyl group, a pyridin-3-ylmethyl group, a 6-chloropyridin-3-ylmethyl group, and a 6-trifluoromethylpyridin-3-ylmethyl group.

In the compound of the present invention, examples of the "C1 to C6 chain hydrocarbon group optionally having one or more halogen atoms" include a methyl group, an ethyl group, a propyl group, an isopropyl group, a butyl group, an isobutyl group, a sec-butyl group, a tert-butyl group, a pentyl group, a neopentyl group, a hexyl group, a trifluoromethyl group, a trichloromethyl group, a 2-fluoroethyl group, a 2,2-difluoroethyl group, a 2,2,2-trifluoroethyl group and a pentafluoroethyl group, a heptafluoroisopropyl group, a vinyl group, a 1-propenyl group, a 2-propenyl group, a 1-methylvinyl group, a 2-methyl-1-propenyl group, a 1-butenyl group, a 2-butenyl group, a 3-butenyl group, a 1-pentenyl group, a 1-hexenyl group, a 1,1-difluoroallyl group, a pentafluoroallyl group, an ethynyl group, a propargyl group, a 2-butynyl group, a 3-butynyl group, a 1-pentynyl group, a 1-hexynyl group, and a 4,4,4-trifluoro-2-butynyl group.

In the compound of the present invention, examples of the "C1 to C6 alkoxy groups optionally having one or more halogen atoms" include a methoxy group, a trifluoromethoxy group, an ethoxy group, a 2,2,2-trifluoroethoxy group, a propoxy group, an isopropoxy group, a butoxy group, an isobutoxy group, a sec-butoxy group, a tert-butoxy group, a pentyloxy group, and a hexyloxy group.

In the compound of the present invention, examples of the "C2 to C6 alkenyloxy groups optionally having one or more halogen atoms" include a 2-propenyloxy group, a 2-methyl-2-propenyloxy group, a 2-butenyloxy group, a 3-butenyloxy group, a 2-pentenyloxy group, a 2-hexenyloxy group, a 3,3-difluoroallyloxy group, and a 3,3-dichloroallyloxy group.

In the compound of the present invention, examples of the "C2 to C6 alkynyloxy groups optionally having one or more halogen atoms" include a propargyloxy group, a 2-butynyloxy group, a 3-butynyloxy group, a 2-pentynyloxy group, a 2-hexynyloxy group, and a 4,4,4-trifluoro-2-butynyloxy group.

In the compound of the present invention, examples of the "C1 to C6 alkylthio groups optionally having one or more halogen atoms" include a methylthio group, an ethylthio group, a propylthio group, an isopropylsulthio group, a butylthio group, a pentylthio group, a hexylthio group, a trifluoromethylthio group, a 2,2,2-trifluoroethylthio group, and a pentafluoroethylthio group.

In the compound of the present invention, examples of the "C1 to C6 alkylsulfinyl groups optionally having one or more halogen atoms" include a methylsulfinyl group, an ethylsulfinyl group, a propylsulfinyl group, an isopropylsulfinyl group, a butylsulfinyl group, a pentylsulfinyl group, a hexylsulfinyl group, a trifluoromethylsulfinyl group, a 2,2,2-trifluoroethylsulfinyl group, and a pentafluoroethylsulfinyl group.

In the compound of the present invention, examples of the "C1 to C6 alkylsulfonyl groups optionally having one or more halogen atoms" include a methylsulfonyl group, an ethylsulfonyl group, a propylsulfonyl group, an isopropylsulfonyl group, a butylsulfonyl group, a pentylsulfonyl group, a hexylsulfonyl group, a trifluoromethylsulfonyl group, a 2,2,2-trifluoroethylsulfonyl group, and a pentafluoroethylsulfonyl group.

In the compound of the present invention, examples of the "C2 to C6 alkylcarbonyl groups optionally having one or more halogen atoms" include an acetyl group, a propionyl group, a butyryl group, a pentanoyl group, a hexanoyl group, and a trifluoroacetyl group.

In the compound of the present invention, examples of the "C2 to C6 alkoxycarbonyl groups optionally having one or more halogen atoms" include a methoxycarbonyl group, an ethoxycarbonyl group, a propoxycarbonyl group, a butoxycarbonyl group, a pentyloxycarbonyl group, a tert-butoxycarbonyl group, and a 2,2,2-trifluoroethoxycarbonyl group.

In the compound of the present invention, examples of the "$C_3$ to $C_6$ cycloalkyl groups optionally having one or more halogen atoms or one or more C1 to C3 alkyl groups" include a cyclopropyl group, a 2,2-difluorocyclopropyl group, a 2,2-dichlorocyclopropyl group, a 2,2-dibromocyclopropyl group, a cyclobutyl group, a cyclopentyl group, and a cyclohexyl group.

In the compound of the present invention, examples of the "C1 to C6 alkylamino groups optionally having one or more halogen atoms" include a methylamino group, an ethylamino group, a 2,2,2-trifluoroethylamino group, a propylamino group, an isopropylamino group, and a butylamino group.

In the compound of the present invention, examples of the "C2 to C8 dialkylamino groups optionally having one or more halogen atoms" include a dimethylamino group, a diethylamino group, a bis(2,2,2-trifluoroethyl)amino group, and a dipropylamino group.

In the compound of the present invention, examples of the "C2 to C6 alkyl group optionally having one or more atoms or groups selected from the group consisting of halogen atoms and a cyclopropyl group (wherein the cyclolpropyl group may have one or more halogen atoms or one or more C1 to C3 alkyl groups)" in the compound of the present invention include an ethyl group, a propyl group, an isopropyl group, a butyl group, an isobutyl group, a sec-butyl group, a tert-butyl group, a pentyl group, a neopentyl group, a hexyl group, a 2-fluoroethyl group, a 2,2-difluoroethyl group, a 2,2,2-trifluoroethyl group, a pentafluoroethyl group, a heptafluoroisopropyl group, a cyclopropylethyl group, a 2-cyclopropylethyl group, a 1-cyclopropylethyl group, and a 1-methylcyclopropylethyl group.

In the compound of the present invention, examples of the "C1 to C6 alkyl group optionally having one or more halogen atoms" include a methyl group, a trifluoromethyl group, an ethyl group, a 2,2,2-trifluoroethyl group, a pentafluoroethyl group, a propyl group, an isopropyl group, a heptafluoropropyl group, a butyl group, an isobutyl group, a sec-butyl group, a tert-butyl group, a pentyl group, and a hexyl group.

In the compound of the present invention, examples of the "phenyl group (wherein the phenyl group optionally has one or more atoms or groups selected from the group consisting of C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms, and $SF_5$" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, 4-pentafluoroethylphenyl group, 4-heptafluoroisopropylphenyl group, a 2-trifluoromethoxyphenyl group, a 3-trifluoromethoxyphenyl group, a 4-trifluoromethoxyphenyl group, a 2-trifluoromethylthiophenyl group, a 3-trifluoromethylsulthiophenyl group, a 4-trifluoromethylthiophenyl group, a 4-trifluoromethylsulfonylphenyl group, a 4-methylsulfinylphenyl group, a 4-methylsulfonylphenyl group, and a 4-$F_5$S phenyl group.

In the compound of the present invention, examples of the "phenyl group (wherein the phenyl group optionally has one or more atoms or groups selected from the group consisting of halogen atoms, C1 to C3 alkyl groups optionally having one or more halogen atoms, $OR^7$, $S(O)_mR^7$, and $SF_5$" include a phenyl group, a 2-fluorophenyl group, a 3-fluorophenyl group, a 4-fluorophenyl group, a 2,3-difluorophenyl group, a 2,4-difluorophenyl group, a 2,5-difluorophenyl group, a 2,6-difluorophenyl group, a 3,4-difluorophenyl group, a 3,5-difluorophenyl group, a 2,3,4,5,6-pentafluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2-trifluoromethylphenyl group, a 3-trifluoromethylphenyl group, a 4-trifluoromethylphenyl group, 4-pentafluoroethylphenyl group, 4-heptafluoroisopropylphenyl group, a 2-trifluoromethoxyphenyl group, a 3-trifluoromethoxyphenyl group, a 4-trifluoromethoxyphenyl group, a 2-trifluoromethylthiophenyl group, a 3-trifluoromethylsulthiophenyl group, a 4-trifluoromethylthiophenyl group, a 4-trifluoromethylsulfonylphenyl group, a 4-methylsulfinylphenyl group, a 4-methylsulfonylphenyl group, and a 4-$F_5S$ phenyl group.

Examples of the "5- or 6-membered heterocyclic group (wherein the 5- or 6-membered heterocyclic group may have one or more atoms or groups selected from the group consisting of C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms, and $SF_5$)" in the compound of the present invention include a pyrrolidin-1-yl group, a 2,5-dimethylpyrrolidin-1-yl group, a 3,3,4,4-tetrafluoropyrrolidin-1-yl group, a tetrahydrofuran-2-yl group, a 2-pyrrolyl group, a 2-furyl group, a 3-furyl group, a 4-trifluoromethyl-2-furyl group, a 5-trifluoromethyl-2-furyl group, a 5-$SF_5$-2-furyl group, a 5-pyrazolyl group, a 4-pyrazolyl group, a 1-pyrrolyl group, a 2-methyl-1-pyrrolyl group, a 2-methylthio-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 4-trifluoromethyl-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 5-trifluoromethyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a piperidyl group, a morpholinyl group, a thiomorpholinyl group, a pyrazinyl group, a 4-pyrimidinyl group, a 5-trifluoromethyl-pyrimidin-2-yl group, a 5-pentafluoroethyl-pyrimidin-2-yl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 5-$SF_5$-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group, and a 5-pentafluoroethylpyridin-2-yl group.

Examples of the "5- or 6-membered heterocyclic group (wherein the 5- or 6-membered heterocyclic group may have one or more atoms or groups selected from the group consisting of halogen atoms, C1 to C3 alkyl groups optionally having one or more halogen atoms, $OR^7$, $S(O)_mR^7$, and $SF_5$)" in the compound of the present invention include a pyrrolidin-1-yl group, a 2,5-dimethylpyrrolidin-1-yl group, a 3,3,4,4-tetrafluoropyrrolidin-1-yl group, a tetrahydrofuran-2-yl group, a 2-pyrrolyl group, a 2-furyl group, a 3-furyl group, a 4-trifluoromethyl-2-furyl group, a 5-pyrazolyl group, a 4-pyrazolyl group, a 1-pyrrolyl group, a 2-methyl-1-pyrrolyl group, a 2-methylthio-1-pyrrolyl group, a 2-methylsulfinyl-1-pyrrolyl group, a 2-methylsulfonyl-1-pyrrolyl group, a 2-methylamino-1-pyrrolyl group, a 2-dimethylamino-1-pyrrolyl group, a 4-trifluoromethyl-1-pyrrolyl group, a 5-bromo-2-furyl group, a 5-nitro-2-furyl group, a 5-cyano-2-furyl group, a 5-methoxy-2-furyl group, a 5-acetyl-2-furyl group, a 5-methoxycarbonyl-2-furyl group, a 2-methyl-3-furyl group, a 2,5-dimethyl-3-furyl group, a 2,4-dimethyl-3-furyl group, a 5-methyl-2-thienyl group, a 3-methyl-2-thienyl group, a 1-methyl-3-trifluoromethyl-5-pyrazolyl group, a 5-chloro-1,3-dimethyl-4-pyrazolyl group, a pyrazol-1-yl group, a 3-chloro-pyrazol-1-yl group, a 3-bromopyrazol-1-yl group, a 4-chloropyrazol-1-yl group, a 4-bromopyrazol-1-yl group, an imidazol-1-yl group, a 1,2,4-triazol-1-yl group, a 3-chloro-1,2,4-triazol-1-yl group, a 1,2,3,4-tetrazol-1-yl group, a 1,2,3,5-tetrazol-1-yl group, a 2-thienyl group, a 3-thienyl group, a 3-trifluoromethyl-1,2,4-triazol-1-yl group, a 4-trifluoromethylpyrazol-1-yl group, a piperidyl group, a morpholinyl group, a thiomorpholinyl group, a pyrazinyl group, a 4-pyrimidinyl group, a 5-trifluoromethyl-pyrimidin-2-yl group, a 5-pentafluoroethyl-pyrimidin-2-yl group, a 5-pyrimidinyl group, a 2-pyridyl group, a 3-pyridyl group, a 4-pyridyl group, a 3-fluoro-2-pyridyl group, a 4-fluoro-2-pyridyl group, a 5-fluoro-2-pyridyl group, a 6-fluoro-2-pyridyl group, a 2-pyrimidinyl group, a 3-chloro-5-trifluoromethylpyridin-2-yl group, a 5-trifluoromethylpyridin-2-yl group, and a 5-pentafluoroethylpyridin-2-yl group.

Examples of the "C1 to C3 alkyl groups optionally having one or more halogen atoms" in the compound of the present invention include a methyl group, a trifluoromethyl group, an ethyl group, a 2,2,2-trifluoroethyl group, a pentafluoroethyl group, a propyl group, an isopropyl group, and a heptafluoroisopropyl group.

In the compound of the present invention, specific examples of the 5-membered aromatic heterocyclic group represented by H1 are shown below. Hereinbelow, the mark "•" in the left part of the structural formula represents a location bonded to a fused heterocyclic group.

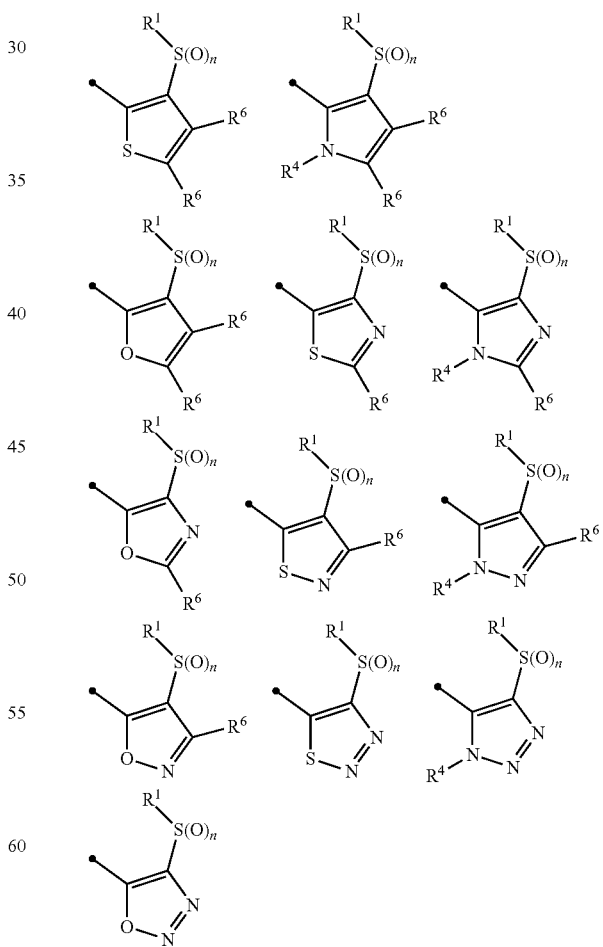

wherein $R^1$, $R^4$, $R^6$ and n represent the same meaning as described above.

In the compound of the present invention, specific examples of the 5-membered aromatic heterocyclic group represented by H2 are shown below. Hereinbelow, the mark "•" in the left part of the structural formula represents a location bonded to a fused heterocyclic group.

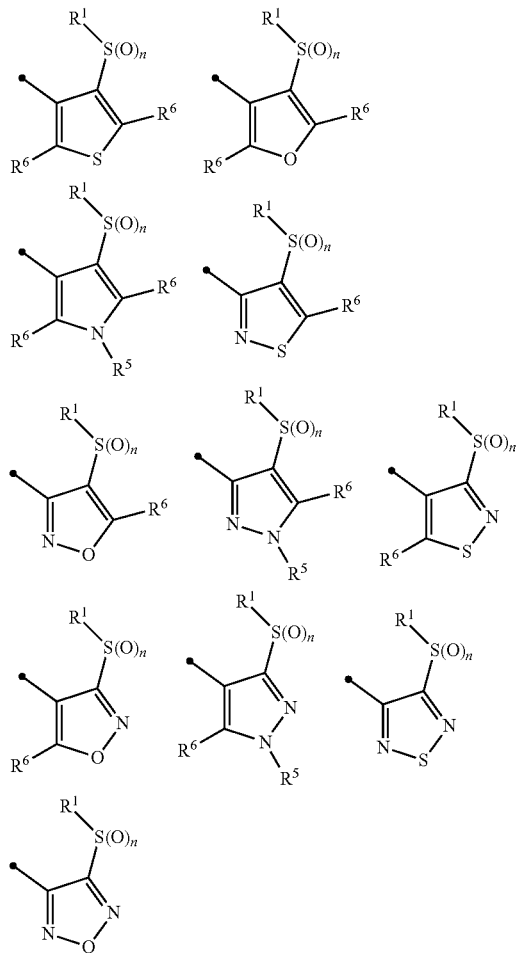

wherein $R^1$, $R^5$, $R^6$ and n represent the same meaning as described above.

In the compound of the present invention, specific examples of the 5-membered aromatic heterocyclic group represented by H3 are shown below. Hereinbelow, the mark "•" in the left part of the structural formula represents a location bonded to a fused heterocyclic group.

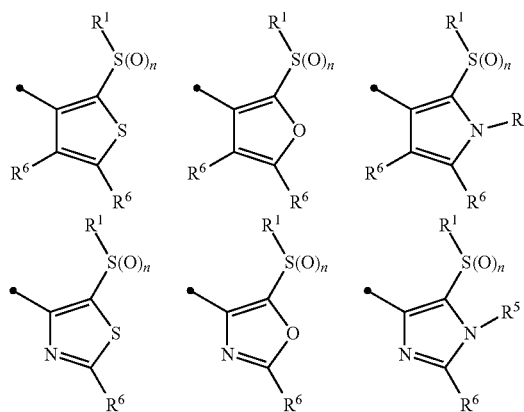

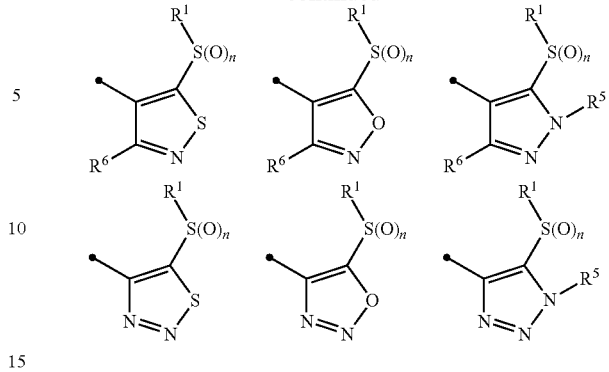

-continued wherein $R^1$, $R^5$, $R^6$ and n represent the same meaning as described above.

In the compound of the present invention, specific examples of the 5-membered aromatic heterocyclic group represented by H4 are shown below. Hereinbelow, the mark "•" in the left part of the structural formula represents a location bonded to a fused heterocyclic group.

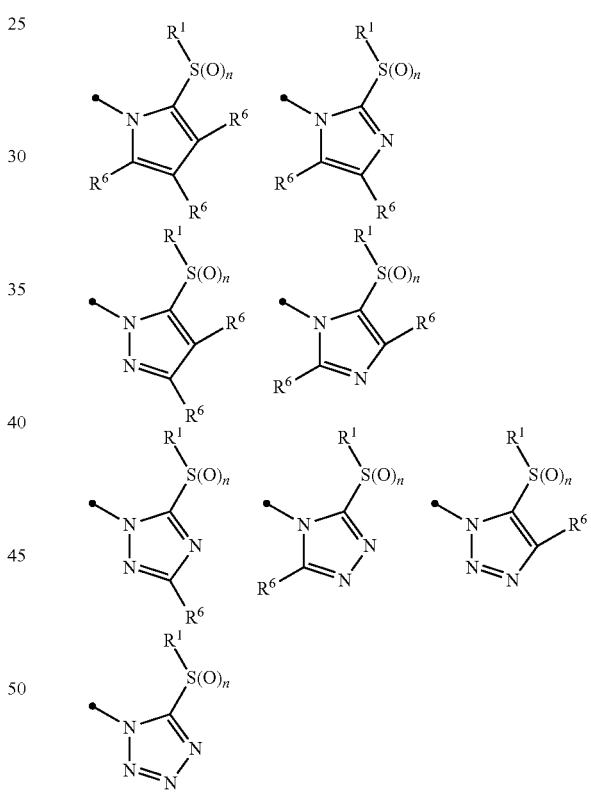

wherein $R^1$, $R^6$ and n represent the same meaning as described above.

Examples of the compound of the present invention include the following compounds.

Embodiment 1

In the general formula (1), compounds wherein Het is H1.

Embodiment 2

In the general formula (1), compounds wherein Het is H2.

Embodiment 3

In the general formula (1), compounds wherein Het is H3.

Embodiment 4

In the general formula (1), compounds wherein Het is H4.

Embodiment 5

In the general formula (1), compounds wherein Het is H1, $Y^1$ is an oxygen atom, a sulfur atom or $NR^4$, $G^1$ and $G^2$ are the same or different and are $CR^6$.

Embodiment 6

In the general formula (1), compounds wherein Het is H1, $Y^1$ is an oxygen atom, a sulfur atom or $NR^4$, $G^1$ is a nitrogen atom, and $G^2$ is $CR^6$.

Embodiment 7

In the general formula (1), compounds wherein Het is H1, $Y^1$ is an oxygen atom, a sulfur atom or NR, $G^2$ is a nitrogen atom, and $G^1$ is $CR^6$.

Embodiment 8

In the general formula (1), compounds wherein Het is H2, $Y^2$ is an oxygen atom or a sulfur atom, $G^1$ and $G^2$ are the same or different and are $CR^6$.

Embodiment 9

In the general formula (1), compounds wherein Het is H2, $Y^2$ is an oxygen atom or a sulfur atom, $G^1$ is a nitrogen atom, and $G^2$ is $CR^6$.

Embodiment 10

In the general formula (1), compounds wherein Het is H2, $Y^2$ is an oxygen atom or a sulfur atom, $G^2$ is a nitrogen atom, and $G^1$ is $CR^6$.

Embodiment 11

In the general formula (1), compounds wherein Het is H3, $Y^2$ is an oxygen atom or a sulfur atom, G and $G^2$ are the same or different and are $CR^6$.

Embodiment 12

In the general formula (1), compounds wherein Het is H3, $Y^2$ is an oxygen atom or a sulfur atom, $G^1$ is a nitrogen atom, and $G^2$ is $CR^6$.

Embodiment 13

In the general formula (1), compounds wherein Het is H3, $Y^2$ is an oxygen atom or a sulfur atom, $G^2$ is a nitrogen atom, and $G^1$ is $CR^6$.

Embodiment 14

In the general formula (1), compounds wherein Het is H4, $G^1$, $G^2$ and $G^3$ are the same or different and are $CR^6$.

Embodiment 15

In the general formula (1), compounds wherein Het is H4, $G^1$ is a nitrogen atom, and $G^2$ and $G^3$ are the same or different and are $CR^6$.

Embodiment 16

In the general formula (1), compounds wherein Het is H4, $G^2$ is a nitrogen atom, and $G^1$ and $G^3$ are the same or different and are $CR^6$.

Embodiment 17

In the general formula (1), compounds wherein $R^1$ is a C1 to C6 alkyl group optionally having one or more atoms or groups selected from group X or a C3 to C6 alicyclic hydrocarbon group optionally having one or more atoms or groups selected from group Y.

Embodiment 18

In the general formula (1), compounds wherein $R^1$ is a C2 to C6 alkyl group optionally having one or more atoms or groups selected from halogen atoms and a cyclopropyl group (wherein the cyclopropyl group optionally has one or more halogen atoms or one or more C1 to C3 alkyl groups).

Embodiment 19

In the general formula (1), compounds wherein $R^1$ is a C2 to C6 alkyl group optionally having one or more atoms or groups selected from halogen atoms and a cyclopropyl group (wherein the cyclopropyl group optionally has one or more halogen atoms or one or more C1 to C3 alkyl groups), and $R^4$ and $R^6$ are the same or different and are a phenyl group (wherein the phenyl group optionally has one or more halogen atoms, C1 to C3 alkyl groups optionally having one or more halogen atoms, $OR^7$, $S(O)_m R^7$, and $SF_5$), a 5- or 6-membered heterocyclic group (wherein the 5- or 6-membered heterocyclic group optionally has one or more atoms or groups selected from halogen atoms, C1 to C3 alkyl groups optionally having one or more halogen atoms, $OR^7$, $S(O)_m R^7$ and $SF_5$), or a C1 to C6 alkyl group optionally having one or more halogen atoms, $OR^7$, $S(O)_m R^7$, $SF_5$, a cyano group, a halogen atom, or a hydrogen atom.

Embodiment 20

In the general formula (1), compounds wherein $R^1$ is a C2 to C6 alkyl group optionally having one or more atoms or groups selected from halogen atoms and a cyclopropyl group (wherein the cyclopropyl group optionally has one or more halogen atoms or one or more C1 to C3 alkyl groups), and $R^4$ and $R^6$ are the same or different and are a phenyl group (wherein the phenyl group optionally has one or more atoms or groups selected from halogen atoms, C1 to C3 alkyls group optionally having one or more halogen atoms, $OR^7$, $S(O)_m R^7$, and $SF_5$), a 5- or 6-membered heterocyclic group (wherein the 5- or 6-membered heterocyclic group optionally has one or more atoms or groups selected from halogen atoms, C1 to C3 alkyl groups optionally having one or more halogen atoms, $OR^7$, $S(O)_m R^7$ and $SF_5$), or a C1 to C6 alkyl group optionally having one or more halogen atoms, $OR^7$, $S(O)_m R^7$, $SF_5$, a cyano group, a halogen atom, or a hydrogen atom, $R^5$ is a 5- or 6-membered heterocyclic group (wherein the 5- or 6-membered heterocyclic group optionally has one or more atoms or groups selected from halogen atoms, C1 to C3 alkyl groups optionally having one or more halogen atoms, $OR^{12}$, $S(O)_pR^{12}$ and $SF_5$), or a C1 to C6 alkyl group optionally having one or more halogen atoms, $OR^{12}$, $S(O)_pR^{12}$, $SF_5$, a cyano group, a halogen atom, or a hydrogen atom, and $R^7$ and $R^{12}$ are the same or different and are a C1 to C6 alkyl group optionally having one or more halogen atoms.

Embodiment 21

In the general formula (1), compounds wherein $R^1$ is an ethyl group, a propyl group, a cyclopropyl group, a cyclopropylmethyl group, a trifluoroethyl group, or a trifluoromethyl group.

Embodiment 22

In the general formula (1), compounds wherein $R^1$ is an ethyl group, a propyl group, a cyclopropyl group, a cyclopropylmethyl group or a trifluoromethyl group, $Y^2$ is an oxygen atom or a sulfur atom, $R^4$ is a pyrimidin-2-yl group, a pyridin-2-yl group or a 5-trifluoromethylpyridin-2-yl group, $R^6$ is a hydrogen atom, a trifluoromethyl group, a difluoromethyl group, a pentafluoroethyl group, a heptafluoroisopropyl group, a trifluoromethoxy group, a trifluoromethylthio group, a trifluoromethylsulfinyl group, a trifluoromethylsulfonyl group, a pyrimidin-2-yl group, a pyridin-2-yl group or a 5-trifluoromethylpyridin-2-yl group.

Embodiment 23

In the general formula (1), compounds wherein Het is represented by the following formulae B1 to B3.

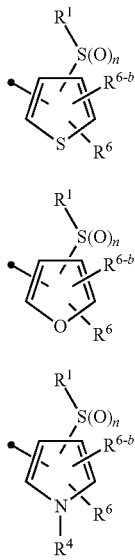

B1

B2

B3 wherein the mark "•" in the left part of the structural formula represents a location bonded to a fused heterocyclic group, and the bond between the fused heterocyclic group and Het and the bond between $S(O)_nR^1$ and Het are in a mutually adjacent positional relationship (ortho position), and $R^{6-b}$ represents a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^7$, $S(O)_mR^7$, $SF_5$, a cyano group, a halogen atom or a hydrogen atom, and $R^1$, $R^4$, $R^6$, $R^7$, m and n represent the same meaning as described above.

Embodiment 24

In the general formula (1), compounds wherein Het is represented by the following formulae B4 to B8.

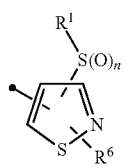

B4

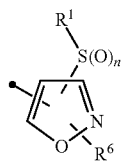

B5

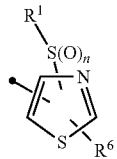

B6

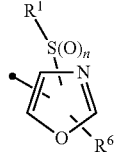

B7

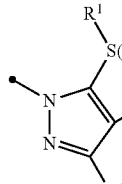

B8 wherein the mark "•" in the left part of the structural formula represents a location bonded to a fused heterocyclic group, and the bond between the fused heterocyclic group and Het and the bond between $S(O)_nR^1$ and Het are in a mutually adjacent (ortho position) positional relationship, and $R^{6-b}$ represents a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^7$, $S(O)_mR^7$, $SF_5$, a cyano group, a halogen atom or a hydrogen atom, and $R^1$, $R^6$, $R^7$, m and n represent the same meaning as described above.

In addition, examples of the compound of the present invention include the following compounds.

Embodiment A1

In the general formula (1), compounds wherein $A^1$ is an oxygen atom.

Embodiment A2

In the general formula (1), compounds wherein $A^1$ is a sulfur atom.

Embodiment A3

In the general formula (1), compounds wherein $A^1$ is $NR^9$.

Embodiment A4

In the general formula (1), compounds wherein $A^2$ is a nitrogen atom.

Embodiment A5

In the general formula (1), compounds wherein $A^2$ is $CR^{10}$.

Embodiment A6

In the general formula (1), compounds wherein $A^3$ is a nitrogen atom.

Embodiment A7

In the general formula (1), compounds wherein $A^3$ is $CR^{11}$.

Embodiment A8

In the general formula (1), compounds wherein $A^1$ is an oxygen atom, and $A^2$ is a nitrogen atom.

Embodiment A9

In the general formula (1), compounds wherein $A^1$ is an oxygen atom, and $A^2$ is $CR^{10}$.

Embodiment A10

In the general formula (1), compounds wherein $A^1$ is an oxygen atom, and $A^3$ is a nitrogen atom.

Embodiment A11

In the general formula (1), compounds wherein $A^1$ is an oxygen atom, and $A^3$ is $CR^{11}$.

Embodiment A12

In the general formula (1), compounds wherein $A^1$ is a sulfur atom, and $A^3$ is $CR^{11}$.

Embodiment A13

In the general formula (1), compounds wherein $A^1$ is a sulfur atom, and $A^2$ is $CR^{10}$.

Embodiment A14

In the general formula (1), compounds wherein $A^1$ is a sulfur atom, and $A^3$ is a nitrogen atom.

Embodiment A15

In the general formula (1), compounds wherein $A^1$ is a sulfur atom, and $A^3$ is $CR^{11}$.

Embodiment A16

In the general formula (1), compounds wherein $A^1$ is $NR^9$, and $A^3$ is $CR^{11}$.

Embodiment A17

In the general formula (1), compounds wherein $A^1$ is $NR^9$, and $A^2$ is $CR^{10}$.

Embodiment A18

In the general formula (1), compounds wherein $A^1$ is $NR^9$, and $A^3$ is a nitrogen atom.

Embodiment A19

In the general formula (1), compounds wherein $A^1$ is $NR^9$, and $A^3$ is $CR^{11}$.

Embodiment A20

In the general formula (1), compounds wherein $A^1$ is an oxygen atom, $A^2$ is $CR^{10}$, and $A^3$ is a nitrogen atom.

Embodiment A21

In the general formula (1), compounds wherein $A^1$ is a sulfur atom, $A^2$ is $CR^{10}$, and $A^3$ is a nitrogen atom.

Embodiment A22

In the general formula (1), compounds wherein $A^1$ is $NR^9$, $A^2$ is $CR^{10}$, and $A^3$ is a nitrogen atom.

Embodiment A23

In the general formula (1), compounds wherein $A^1$ is an oxygen atom, $A^2$ is $CR^{10}$, and $A^3$ is $CR^{11}$.

Embodiment A24

In the general formula (1), compounds wherein $A^1$ is a sulfur atom, $A^2$ is $CR^{10}$, and $A^3$ is $CR^{11}$.

Embodiment A25

In the general formula (1), compounds wherein $A^1$ is $NR^9$, $A^2$ is $CR^{10}$, and $A^3$ is $CR^{11}$.

Embodiment A26

In the general formula (1), compounds wherein $A^2$ is $CR^{10}$, or $A^3$ is $CR^{11}$, and $R^{10}$ and $R^{11}$ are the same or different and are a C1 to C6 chain hydrocarbon group optionally having one or more halogen atoms, $OR^{17}$, $S(O)_rR^{17}$, a halogen atom or a hydrogen atom.

Embodiment A27

In the general formula (1), compounds wherein $R^2$ and $R^3$ are the same or different and are a C1 to C6 chain hydrocarbon group optionally having one or more halogen atoms, $OR^{14}$, $S(O)_qR^{14}$, a halogen atom or a hydrogen atom.

Embodiment A28

In the general formula (1), compounds wherein $A^1$ is an oxygen atom, $A^2$ is $CR^{10}$, and $R^{10}$ is a C1 to C6 chain hydrocarbon group optionally having one or more halogen atoms, $OR^{17}$, $S(O)_r R^{17}$, a halogen atom or a hydrogen atom.

Embodiment A29

In the general formula (1), compounds wherein $A^1$ is a sulfur atom, $A^2$ is $CR^{10}$, and $R^{10}$ is a C1 to C6 chain hydrocarbon group optionally having one or more halogen atoms, $OR^{17}$, $S(O)_r R^{17}$, a halogen atom or a hydrogen atom.

Embodiment A30

In the general formula (1), compounds wherein $A^1$ is $NR^9$, $A^2$ is $CR^{10}$, and $R^{10}$ is a C1 to C6 chain hydrocarbon group optionally having one or more halogen atoms, $OR^{17}$, $S(O)_r R^{17}$, a halogen atom or a hydrogen atom.

Embodiment A31

In the general formula (1), compounds wherein $A^1$ is $NR^9$, $R^9$ is a C1 to C6 alkyl group optionally having one or more halogen atoms, $A^2$ is $CR^{10}$, $R^{10}$ is a hydrogen atom, $A^3$ is $CR^{11}$, and $R^{11}$ is a C1 to C6 chain hydrocarbon group optionally having one or more halogen atoms, $OR^{17}$, $S(O)_r R^{17}$, a halogen atom or a hydrogen atom.

Embodiment A32

In the general formula (1), compounds wherein $A^1$ is $NR^9$, $R^9$ is a C1 to C3 alkyl group, $A^2$ is $CR^{10}$, $R^{10}$ is a hydrogen atom, $A^3$ is a nitrogen atom, and $R^3$ is a hydrogen atom.

Embodiment A33

In the general formula (1), compounds wherein $A^1$ is $NR^9$, $R^9$ is a C1 to C3 alkyl group, $A^2$ is $CR^{10}$, $R^{10}$ is a hydrogen atom, $A^3$ is a nitrogen atom, $R^2$ is a C1 to C3 alkyl group optionally having one or more halogen atoms, $OR^{14}$ or $S(O)_q R^{14}$, $R^{14}$ is a C1 to C3 alkyl group optionally having one or more halogen atoms, and $R^3$ is a hydrogen atom.

Examples of the compound of the present invention also include the following compounds.

Compounds as defined in any of [Embodiment A1] to [Embodiment A33], wherein the Het is [Embodiment 1] to [Embodiment 23].

Furthermore, examples of the compound of the present invention also include the following compounds.

Embodiment B1

In the general formula (1), compounds
wherein Het to which $R^1$—$S(O)_n$ is bonded is formula H1, H2, H3 or H4,
$Y^1$ is an oxygen atom, a sulfur atom or $NR^4$, $R^4$ is a C1 to C3 alkyl group optionally having one or more halogen atoms (particularly, a fluorine atom) or a hydrogen atom,
$Y^2$ is an oxygen atom, a sulfur atom or $NR^5$, $R^5$ is a C1 to C3 alkyl group optionally having one or more halogen atoms (particularly, a fluorine atom) or a hydrogen atom,
$G^1$, $G^2$ and $G^3$ are the same or different and are $CR^6$ or a nitrogen atom, $R^6$ is a C1 to C3 alkyl group optionally having one or more halogen atoms (particularly, a fluorine atom) or a hydrogen atom,
$R^1$ is a C1 to C6 alkyl group optionally having one or more atoms or groups selected from halogen atoms (particularly, a fluorine atom) and a cyclopropyl group, a C2 to C6 alkenyl group (particularly, a vinyl group), a C2 to C6 alkynyl group (particularly, an ethynyl group) or a C3 to C6 alicyclic hydrocarbon group (particularly, a cyclopropyl group),
$R^2$ is a C1 to C6 alkyl group optionally having one or more halogen atoms, $OR^{14}$ or $S(O)_q R^{14}$, $R^{14}$ is a C1 to C6 alkyl group optionally having one or more halogen atoms,
$R^3$ is a hydrogen atom,
$A^1$ is an oxygen atom, a sulfur atom or $NR^9$, $R^9$ is a C1 to C6 chain hydrocarbon group (particularly, a C1 to C3 alkyl group),
$A^2$ is CH,
$A^3$ is a nitrogen atom or $CR^{11}$, and $R^{11}$ is a halogen atom or a hydrogen atom.

Embodiment B2

Among the [Embodiment B1] described above, in the general formula (1), compounds wherein $R^1$ is a C1 to C6 alkyl group (particularly, an ethyl group).

Embodiment B3

Among the [Embodiment B1] described above, in the general formula (1), compounds wherein $A^3$ is a nitrogen atom.

Embodiment B4

Among the [Embodiment B1] described above, in the general formula (1), compounds wherein $R^2$ is a C1 to C6 haloalkyl group, $OR^{14}$ or $S(O)_q R^{14}$, and $R^{14}$ is a C1 to C6 haloalkyl group.

Embodiment B5

In the general formula (1), compounds
wherein Het to which $R^1$—$S(O)_n$ is bonded is formula H1, H2, H3 or H4,
$Y^1$ is an oxygen atom, a sulfur atom or $NR^4$, $R^4$ is a methyl group, a trifluoromethyl group or a hydrogen atom,
$Y^2$ is an oxygen atom, a sulfur atom or $NR^5$, $R^5$ is a methyl group, a trifluoromethyl group or a hydrogen atom,
$G^1$, $G^2$ and $G^3$ are the same or different and are $CR^6$ or a nitrogen atom, $R^6$ is a methyl group, a trifluoromethyl group or a hydrogen atom,
$R^1$ is a C1 to C3 alkyl group (particularly, an ethyl group),
$R^2$ is a trifluoromethyl group, a 2,2,2-trifluoroethyl group, a trifluoromethoxy group, a trifluoromethylthio group, a trifluoromethylsulfinyl group or a trifluoromethylsulfonyl group,
$R^3$ is a hydrogen atom,
$A^1$ is an oxygen atom, a sulfur atom or $NR^9$, $R^9$ is a C1 to C3 alkyl group (particularly, a methyl group),
$A^2$ is CH, and
$A^3$ is N.

Next, the method for producing the compound of the present invention will be described.

The compound of the present invention can be produced, for example, according to the following (Production Method 1) to (Production Method 17).

(Production Method 1)

A method for producing, among the compounds of the present invention, a compound of the present invention represented by the general formula (1-2) or a compound of the present invention represented by the general formula (1-3).

As the following scheme, the compound of the present invention represented by the general formula (1-3) can be produced through step (1-a) and step (1-b), or through step (1-c).

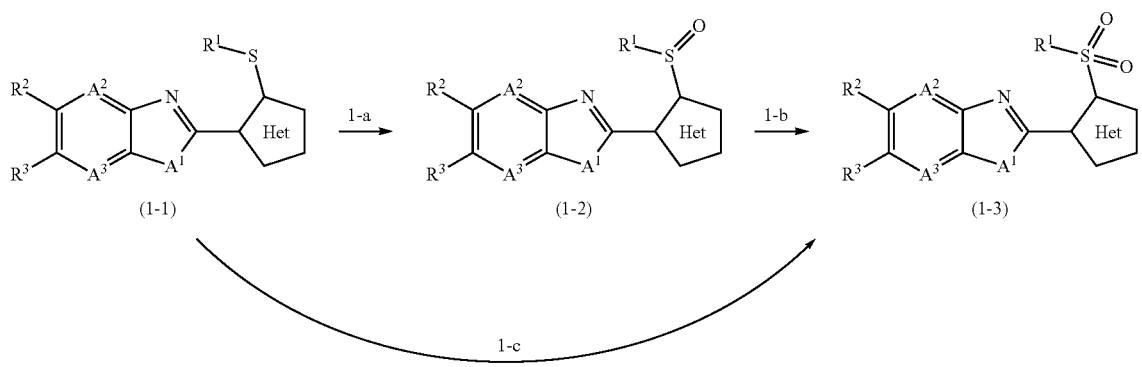

(1-1)   (1-2)   (1-3)

wherein $R^1$, $R^2$, $R^3$, $A^1$, $A^2$, $A^3$ and Het represent the same meaning as described above.

Step (1-a)

The compound of the present invention represented by the general formula (1-2) can be produced by subjecting a compound of the present invention represented by the general formula (1-1) to an oxidation reaction.

The oxidation reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include sodium periodate and m-chloroperbenzoic acid.

In the reaction, the oxidizing agent is usually used in a ratio of 1 to 3 mol, based on 1 mol of the compound of the present invention represented by the general formula (1-1). Preferably, the oxidizing agent is used in a ratio of 1 to 1.2 mol, based on the compound of the present invention represented by the general formula (1-1).

The reaction temperature is usually within the range of −20 to 80° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and is subjected to post-treatment operations such as drying and concentration, whereby the compound of the present invention represented by the general formula (1-2) can be isolated. The isolated compound of the present invention represented by the general formula (1-2) also can be further purified by chromatography, recrystallization, or the like.

Step (1-b)

The compound of the present invention represented by the general formula (1-3) can be produced by reacting the compound of the present invention represented by the general formula (1-2) with an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 1 to 4 mol, based on 1 mol of the compound of the present invention represented by the general formula (1-2). Preferably, the oxidizing agent is used in a ratio of 1 to 2 mol, based on 1 mol of the compound of the present invention represented by the general formula (1-2).

The reaction temperature is usually within the range of −20 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and is subjected to post-treatment operations such as drying and concentration, whereby the compound of the present invention represented by the general formula (1-3) can be isolated. The compound of the present invention represented by the general formula (1-3) also can be further purified by chromatography, recrystallization, or the like.

Step (1-c)

The compound of the present invention represented by the general formula (1-3) can be produced by reacting the compound of the present invention represented by the general formula (1-1) with an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

In the reaction, the oxidizing agent is usually used in a ratio of 2 to 6 mol, based on 1 mol of the compound of the present invention represented by the general formula (1-1). Preferably, the oxidizing agent is used in a ratio of 2 to 3 mol, based on 1 mol of the compound of the present invention represented by the general formula (1-1).

The reaction temperature is usually within the range of −20 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and is subjected to post-treatment operations such as drying and concentration, whereby the compound of the present invention represented by the general formula (1-3) can be isolated. The compound of the present invention represented by the general formula (1-3) also can be further purified by chromatography, recrystallization, or the like.

(Production Method 2)

The compound of the present invention represented by the general formula (1) can be produced by inducing a compound represented by the general formula (2-2) through step (2-a) or step (2-b), then undergoing step (2-c), or undergoing step (2-d) or step (2-d), as the following scheme.

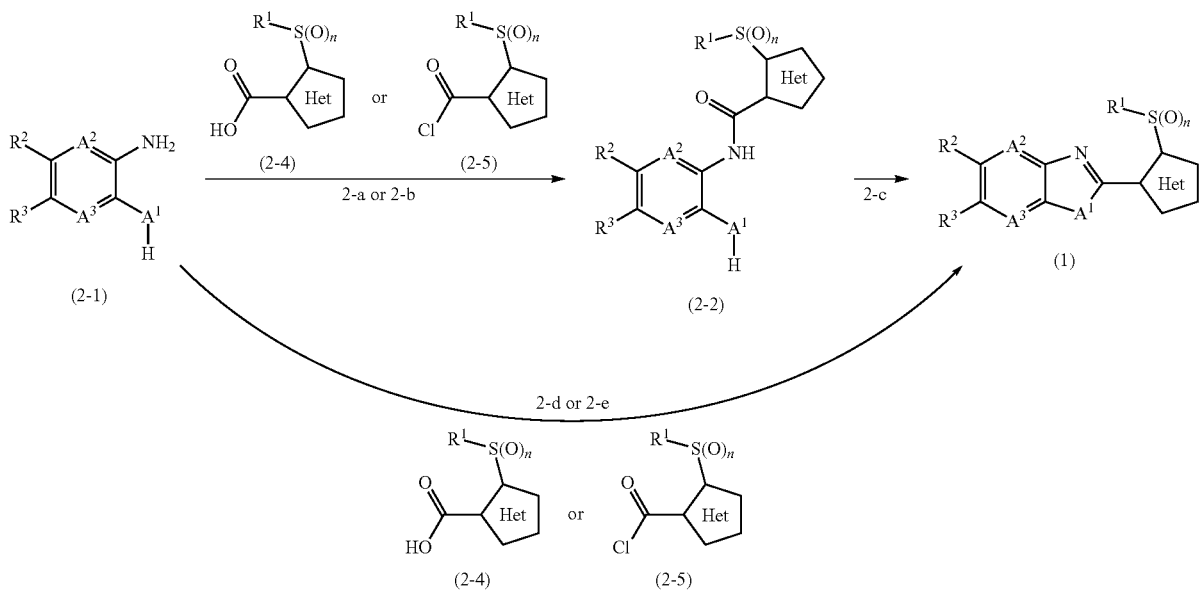

wherein $R^1$, $R^2$, $R^3$, $A^1$, $A^2$, $A^3$, n and Het represent the same meaning as described above.

Step (2-a)

The compound represented by the general formula (2-2) can be produced by reacting a compound represented by the general formula (2-1) with the general formula (2-4) in the presence of a condensing agent.

The reaction is usually carried out in the presence of a solvent. Examples of the solvent include ethers such as 1,4-dioxane, diethyl ether, tetrahydrofuran (hereinafter, referred to as THF) and tert-butyl methyl ether, halogenated hydrocarbons such as dichloromethane, chloroform, carbon tetrachloride, 1,2-dichloroethane and chlorobenzene, hydrocarbons such as toluene, benzene and xylene, esters such as ethyl acetate and butyl acetate, nitriles such as acetonitrile, aprotic polar solvents such as N,N-dimethylformamide (hereinafter, referred to as DMF), N-methylpyrrolidone (hereinafter, referred to as NMP), 1,3-dimethyl-2-imidazolidinone and dimethyl sulfoxide (hereinafter, referred to as DMSO), nitrogen-containing aromatic compounds such as pyridine and quinolone, and mixtures thereof.

Examples of the condensing agent include carbodiimides such as 1-ethyl-3-(3-dimethylaminopropyl)carbodiimide hydrochloride (hereinafter, referred to as EDCI hydrochloride) and 1,3-dicyclohexylcarbodiimide.

The reaction can be also carried out by adding a catalyst, as necessary. Examples of the catalyst include 1-hydroxybenzotriazole (hereinafter, referred to as HOBt).

In the reaction, the general formula (2-4) is usually used in a ratio of 0.5 to 2 mol, the condensing agent is usually used in a ratio of 1 to 5 mol, and the catalyst is usually used in a ratio of 0.01 to 1 mol, based on 1 mol of the compound represented by the general formula (2-1).

The reaction temperature is usually within the range of 0 to 120° C. The reaction time is usually within the range of 0.1 to 24 hours.

After completion of the reaction, the compound represented by the general formula (2-2) can be isolated by pouring the reaction mixture into water, then extracting the mixture with an organic solvent, and concentrating the organic layer; collecting a solid generated by pouring the reaction mixture into water by filtration; or collecting a solid generated in the reaction mixture by filtration. The isolated compound represented by the general formula (2-2) can be also further purified by recrystallization, chromatography, or the like.

Step (2-b)

The compound represented by the general formula (2-2) can be also produced by reacting the compound represented by the general formula (2-1) with a compound represented by the general formula (2-5).

The reaction is usually carried out in the presence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, acid amides such as DMF and NMP, sulfoxides such as DMSO, and mixtures thereof.

The reaction can be also carried out by adding a base, as necessary. Examples of the base include alkali metal carbonates such as sodium carbonate and potassium carbonate, tertiary amines such as triethylamine and diisopropylethylamine, and nitrogen-containing aromatic compounds such as pyridine and 4-dimethylaminopyridine.

In the reaction, the compound represented by the general formula (2-5) is usually used in a ratio of 1 to 3 mol, and the base is usually used in a ratio of 1 to 10 mol, based on 1 mol of the compound represented by the general formula (2-1).

The reaction temperature is usually within the range of −20 to 100° C. The reaction time is usually within the range of 0.1 to 24 hours.

After completion of the reaction, the compound represented by the general formula (2-2) can be isolated by pouring water to the reaction mixture, then extracting the mixture with an organic solvent, and subjecting the organic layer to post-treatment operations such as drying and concentration. The isolated compound represented by the general formula (2-2) can be also further purified by chromatography, recrystallization, or the like.

Step (2-c)

The compound of the present invention represented by the general formula (1) can be produced by intramolecular condensation of the compound represented by the general formula (2-2).

The reaction is usually carried out in the presence of a solvent. Examples of the solvent include ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, hydrocarbons such as toluene, benzene and xylene, esters such as ethyl acetate and butyl acetate, nitriles such as acetonitrile, aprotic polar solvents such as DMF, NMP, 1,3-dimethyl-2-imidazolidinone and dimethyl sulfoxide, nitrogen-containing aromatic compounds such as pyridine and quinoline, and mixtures thereof.

The reaction can use a condensing agent, an acid, a base or a chlorinating agent, as necessary.

Examples of the condensing agent include a mixture of phosphorus oxychloride, acetic anhydride, trifluoroacetic anhydride, EDCI hydrochloride, a mixture of triphenylphosphine, a base and carbon tetrachloride or carbon tetrabromide, and a mixture of triphenylphosphine and azodiesters such as diethyl azodicarboxylate.

Examples of the acid include sulfonic acids such as p-toluenesolufonic acid, carboxylic acids such as acetic acid, and polyphosphoric acid.

Examples of the base include nitrogen-containing heterocyclic compounds such as pyridine, picoline, 2,6-lutidine, 1,8-diazabicyclo[5.4.0]-7-undecene (hereinafter referred to as DBU) and 1,5-diazabicyclo[4.3.0]-5-nonene, tertiary amines such as triethylamine and N-ethyldiisopropylamine, and inorganic bases such as tripotassium phosphate, potassium carbonate and sodium hydride.

Examples of the chlorinating agent include phosphorus oxychloride.

In the reaction, when a condensing agent is used, the condensing agent is usually used in a ratio of 1 to 5 mol, when an acid is used, the acid is usually used in a ratio of 0.1 to 5 mol, when a base is used, the base is usually used in a ratio of 1 to 5 mol, and when a chlorinating agent is used, the chlorinating agent is usually used in a ratio of 1 to 5 mol, based on 1 mol of the compound represented by the general formula (2-2).

The reaction temperature is usually within the range of 0 to 200° C. The reaction time is usually within the range of 0.1 to 24 hours.

After completion of the reaction, the compound of the present invention represented by the general formula (1) can be isolated by pouring the reaction mixture to water, then extracting the mixture with an organic solvent, and concentrating the organic layer; collecting a solid generated by pouring the reaction mixture to water by filtration; or collecting a solid generated in the reaction mixture by filtration. The isolated compound of the present invention represented by the general formula (1) can be also further purified by recrystallization, chromatography, or the like.

Step (2-d)

The compound of the present invention represented by the general formula (1) can be produced by reacting the compound represented by the general formula (2-1) with a compound represented by the general formula (2-4) in the presence of a condensing agent.

The reaction is usually carried out in the presence of a solvent. Examples of the solvent include ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, hydrocarbons such as toluene, benzene and xylene, esters such as ethyl acetate and butyl acetate, nitriles such as acetonitrile, aprotic polar solvents such as DMF, NMP, 1,3-dimethyl-2-imidazolidinone and dimethyl sulfoxide, nitrogen-containing aromatic compounds such as pyridine and quinolone, and mixtures thereof.

Examples of the condensing agent include carbodiimides such as EDCI hydrochloride and 1,3-dicyclohexylcarbodiimide.

The reaction can be also carried out by adding a catalyst, as necessary. Examples of the catalyst include 1-hydroxybenzotriazole.

In the reaction, the compound represented by the general formula (2-4) is usually used in a ratio of 0.5 to 2 mol, the condensing agent is usually used in a ratio of 1 to 5 mol, and the catalyst is usually used in a ratio of 0.01 to 1 mol, based on 1 mol of the compound represented by the general formula (2-1).

The reaction temperature is usually within the range of 0 to 200° C. The reaction time is usually within the range of 0.1 to 24 hours.

After completion of the reaction, the compound of the present invention represented by the general formula (1) can be isolated by pouring the reaction mixture to water, then extracting the mixture with an organic solvent, and concentrating the organic layer; collecting a solid generated by pouring the reaction mixture to water by filtration; or collecting a solid generated in the reaction mixture by filtration. The isolated compound of the present invention represented by the general formula (1) can be also further purified by recrystallization, chromatography, or the like.

Step (2-e)

The compound of the present invention represented by the general formula (1) can be produced by reacting the compound represented by the general formula (2-1) with the compound represented by the general formula (2-5).

The reaction is usually carried out in the presence or absence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, acid amides such as DMF and NMP, sulfoxides such as DMSO, and mixtures thereof.

The reaction can be also carried out by adding a base, as necessary. Examples of the base include alkali metal carbonates such as sodium carbonate and potassium carbonate, tertiary amines such as triethylamine and diisopropylethylamine, and nitrogen-containing aromatic compounds such as pyridine and 4-dimethylaminopyridine.

In the reaction, the compound represented by the general formula (2-5) is usually used in a ratio of 1 to 3 mol, and the base is usually used in a ratio of 1 to 10 mol, based on 1 mol of the compound represented by the general formula (2-1).

The reaction temperature is usually within the range of 20 to 200° C. The reaction time is usually within the range of 0.1 to 24 hours.

After completion of the reaction, the compound of the present invention represented by the general formula (1) can be isolated by pouring water to the reaction mixture, then extracting the mixture with an organic solvent, and subjecting the organic layer to post-treatment operations such as drying and concentration. The compound of the present invention represented by the general formula (1) can be also further purified by chromatography, recrystallization, or the like.
(Production Method 3)

A method for producing, among the compounds of the present invention, a compound of the present invention wherein $A^1$ is a sulfur atom, and $A^3$ is a nitrogen atom.

A compound of the present invention represented by the general formula (3-3) can be produced by inducing a compound represented by the general formula (3-2) through step (3-a) or step (3-b), then undergoing step (3-c), as the following scheme.

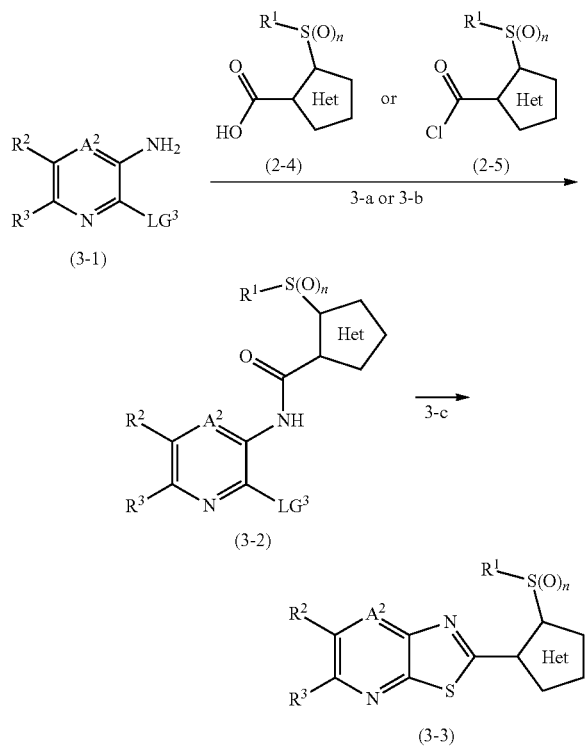

wherein $R^1$, $R^2$, $R^3$, $A^2$, n and Het represent the same meaning as described above, $LG^3$ represents a leaving group such as a fluorine atom, a chlorine atom, a bromine atom, an iodine atom, a methanesulfonyloxy group, a p-toluenesulfonyloxy atom, or a trifluoromethanesulfonyloxy group.)

Step (3-a)

The compound represented by the general formula (3-2) can be produced by reacting a compound represented by the general formula (3-1) with the compound represented by the general formula (2-4) in the presence of a dehydration condensing agent.

The reaction is usually carried out in the presence or absence of a solvent. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, acid amides such as DMF and NMP, sulfoxides such as DMSO, nitrogen-containing aromatic compounds such as pyridine and quinoline, and mixtures thereof.

Examples of the dehydration condensing agent include carbodiimides such as EDCI hydrochloride and 1,3-dicyclohexylcarbodiimide, and BOP reagent.

In the reaction, the compound represented by the general formula (2-4) is usually used in a ratio of 1 to 3 mol, and the dehydration condensing agent is usually used in a ratio of 1 to 5 mol, based on 1 mol of the compound represented by the general formula (3-1).

The reaction temperature is usually within the range of 0 to 200° C. The reaction time is usually within the range of 0.1 to 24 hours.

After completion of the reaction, the compound represented by the general formula (3-2) can be isolated by pouring water to the reaction mixture, then extracting the mixture with an organic solvent, and subjecting the organic layer to post-treatment operations such as drying and concentration. The isolated compound represented by the general formula (3-2) can be also further purified by chromatography, recrystallization, or the like.

Step (3-b)

The compound represented by the general formula (3-2) can be produced by reacting a compound represented by the general formula (3-1) with the compound represented by the general formula (2-5).

The reaction is usually carried out in the presence or absence of a solvent. The reaction can be also carried out by adding a base as necessary. Examples of the solvent include ethers such as THF, ethylene glycol dimethyl ether, tert-butyl methyl ether and 1,4-dioxane, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile, acid amides such as DMF and NMP, sulfoxides such as DMSO, nitrogen-containing aromatic compounds such as pyridine and quinoline, and mixtures thereof.

Examples of the base include alkali metal carbonates such as sodium carbonate and potassium carbonate, tertiary amines such as triethylamine and diisopropylethylamine, and nitrogen-containing aromatic compounds such as pyridine and 4-dimethylaminopyridine.

In the reaction, the compound represented by the general formula (2-5) is usually used in a ratio of 1 to 3 mol, and the base is usually used in a ratio of 1 to 5 mol, based on 1 mol of the compound represented by the general formula (3-1).

The reaction temperature is usually within the range of 0 to 200° C. The reaction time is usually within the range of 0.1 to 24 hours.

After completion of the reaction, the compound represented by the general formula (3-2) can be isolated by pouring water to the reaction mixture, then extracting the mixture with an organic solvent, and subjecting the organic layer to post-treatment operations such as drying and concentration. The isolated compound represented by the general formula (3-2) can be also further purified by chromatography, recrystallization, or the like.

Step (3-c)

The compound of the present invention represented by the general formula (3-3) can be produced by reacting the compound represented by the general formula (3-2) with a sulfurizing agent.

The reaction is usually carried out in the presence or absence of a solvent. Examples of the solvent include ethers such as 1,4-dioxane, diethyl ether, tetrahydrofuran, tert-butyl methyl ether and diglyme, halogenated hydrocarbons such as dichloromethane, chloroform, carbon tetrachloride, 1,2-dichloroethane and chlorobenzene, hydrocarbons such as toluene, benzene and xylene, nitriles such as acetonitrile, pyridines such as pyridine, picoline and lutidine, and mixtures thereof.

Examples of the sulfurizing agent include diphosphorus pentasulfide and Lawesson's reagent (2,4-bis-(4-methoxyphenyl)-1,3-dithia-2,4-diphosphetane-2,4-disulfide).

In the reaction, the sulfurizing agent is usually used in a ratio of 1 to 3 mol, based on 1 mol of the compound represented by the general formula (3-2).

The reaction temperature is usually within the range of 0 to 200° C. The reaction time is usually within the range of 1 to 24 hours.

After completion of the reaction, the compound of the present invention represented by the general formula (3-3) can be isolated by pouring the reaction mixture to water, then extracting the mixture with an organic solvent, and concentrating the organic layer; collecting a solid generated by pouring the reaction mixture to water by filtration; or collecting a solid generated in the reaction mixture by filtration. The isolated compound of the present invention represented by the general formula (3-3) can be also further purified by recrystallization, chromatography, or the like.

(Production Method 4)

The compound of the present invention represented by the general formula (1) can be produced by reacting a compound represented by the general formula (4-1) with a compound represented by the general formula (4-2), in the presence of an oxidizing agent.

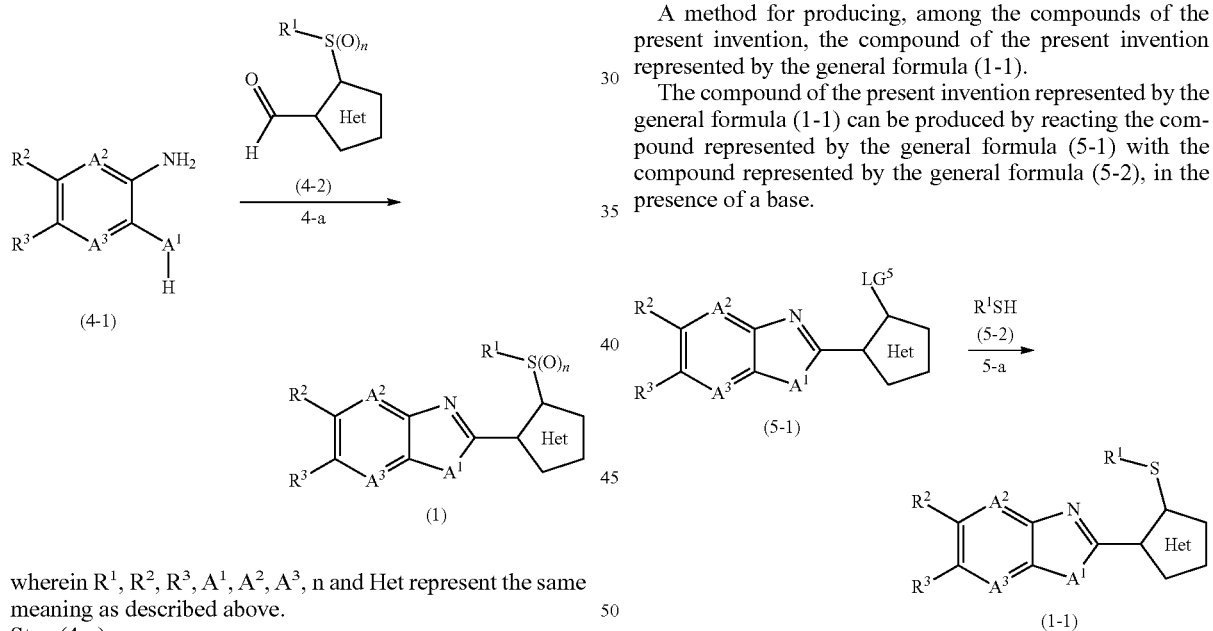

wherein $R^1$, $R^2$, $R^3$, $A^1$, $A^2$, $A^3$, n and Het represent the same meaning as described above.

Step (4-a)

The reaction is usually carried out in the presence of a solvent. Examples of the solvent include alcohols such as methanol and ethanol, ethers such as 1,4-dioxane, diethyl ether, THF and tert-butyl methyl ether, halogenated hydrocarbons such as dichloromethane, chloroform, carbon tetrachloride, 1,2-dichloroethane and chlorobenzene, hydrocarbons such as toluene, benzene and xylene, esters such as ethyl acetate and butyl acetate, nitriles such as acetonitrile, aprotic polar solvents such as DMF, NMP, 1,3-dimethyl-2-imidazolidinone and dimethyl sulfoxide, nitrogen-containing aromatic compounds such as pyridine and quinoline, and mixtures thereof.

The reaction can be also carried out by adding an acid, as necessary. Examples of the acid include sulfonic acids such as p-toluenesolufonic acid, carboxylic acids such as acetic acid, and polyphosphoric acid.

The reaction can be also carried out by adding a sulfite, as necessary. Examples of the sulfite include sulfites such as sodium bisulfite and sodium disulfite.

Examples of the oxidizing agent include oxygen, copper (II) chloride, and DDQ.

In the reaction, the compound represented by the general formula (4-2) is usually used in a ratio of 1 to 2 mol, when an acid is used, the acid is usually used in a ratio of 0.1 to 2 mol, when a sulfite is used, the sulfite is usually used in a ratio of 1 to 5 mol, and the oxidizing agent is usually used in a ratio of 1 to 5 mol, based on 1 mol of the compound represented by the general formula (4-1).

The reaction temperature is usually within the range of 0 to 200° C. The reaction time is usually within the range of 0.1 to 24 hours.

After completion of the reaction, the compound of the present invention represented by the general formula (1) can be isolated by pouring the reaction mixture to water, then extracting the mixture with an organic solvent, and concentrating the organic layer; collecting a solid generated by pouring the reaction mixture into water by filtration; or collecting a solid generated in the reaction mixture by filtration. The isolated compound of the present invention represented by the general formula (1) can be also further purified by recrystallization, chromatography, or the like.

(Production Method 5)

A method for producing, among the compounds of the present invention, the compound of the present invention represented by the general formula (1-1).

The compound of the present invention represented by the general formula (1-1) can be produced by reacting the compound represented by the general formula (5-1) with the compound represented by the general formula (5-2), in the presence of a base.

wherein $R^1$, $R^2$, $R^3$, $A^1$, $A^2$, $A^3$ and Het represent the same meaning as described above, $LG^5$ represents a leaving group such as a fluorine atom, a chlorine atom, a bromine atom, an iodine atom, a methanesulfonyloxy group, a p-toluenesulfonyloxy atom, or a trifluoromethanesulfonyloxy group.

Step (5-a)

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

Examples of the base include alkali metal carbonates such as sodium carbonate and potassium carbonate and alkali metal hydrides such as sodium hydride.

In the reaction, the compound represented by the general formula (5-2) is usually used in a ratio of 1 to 10 mol, and the base is usually used in a ratio of 1 to 10 mol, based on 1 mol of the compound represented by the general formula (5-1).

The reaction temperature is usually within the range of 0 to 150° C. The reaction time is usually within the range of 0.5 to 24 hours.

After completion of the reaction, the compound of the present invention represented by the general formula (1-1) can be isolated by extracting the reaction mixture with an organic solvent and subjecting the organic layer to post-treatment operations such as drying and concentration. The isolated compound of the present invention represented by the general formula (1-1) can be also further purified by chromatography, recrystallization, or the like.

(Production Method 6)

A method for producing, among the compounds of the present invention, the compound of the present invention represented by the general formula (1-1).

As the following scheme, the compound of the present invention represented by the general formula (1-1) can be produced through step (6-a) and step (6-b), or through step (6-c).

Step (6-c)

The compound of the present invention represented by the general formula (1-1) can be produced, using the compound represented by the general formula (6-1) in place of the compound represented by the general formula (5-1), in accordance with the method of Production Method 5.

(Production Method 7)

A method for producing, among the compounds of the present invention, the compound of the present invention represented by the general formula (1-1).

The compound of the present invention represented by the general formula (1-1) can be produced by reacting a compound represented by the general formula (7-1) or a compound represented by the general formula (7-2) with a compound represented by the general formula (7-3), in the presence of a base.

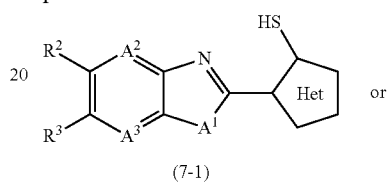

(7-1)

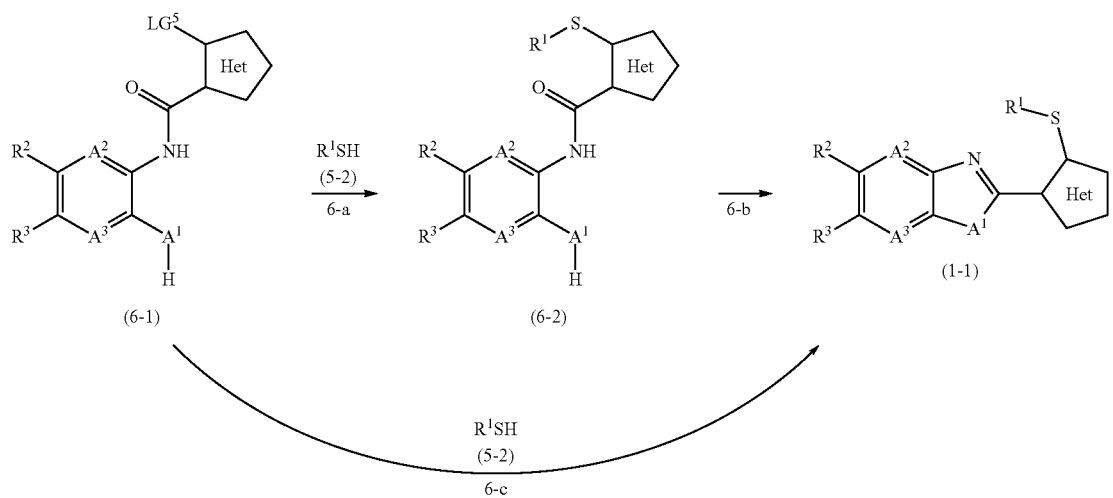

wherein $R^1$, $R^2$, $R^3$, $A^1$, $A^2$, $A^3$, $LG^5$ and Het represent the same meaning as described above.

Step (6-a)

A compound represented by the general formula (6-2) can be produced, using a compound represented by the general formula (6-1) in place of the compound represented by the general formula (5-1), in accordance with the method of Production Method 5.

Step (6-b)

The compound of the present invention represented by the general formula (1-1) can be produced, using the compound represented by the general formula (6-2) in place of the compound represented by the general formula (2-2), in accordance with step (2-c) of the method of Production Method 2.

-continued

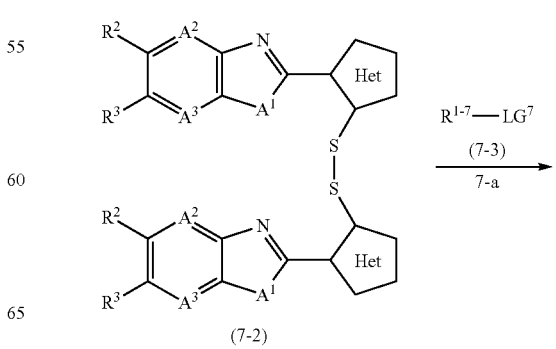

(7-2)

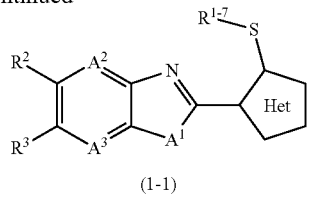

(1-1)

wherein $R^2$, $R^3$, $A^1$, $A^2$, $A^3$ and Het represent the same meaning as described above, $R^{1-7}$ represents a group other than hydrogen atom of $R^1$ in the general formula (1), $LG^7$ represents a leaving group such as a chlorine atom, a bromine atom, an iodine atom, a methanesulfonyloxy group, a p-toluenesulfonyloxy atom, or a trifluoromethanesulfonyloxy group.)

Step (7-a)

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

Examples of the base include hydrides of alkali metals or alkaline earth metals such as sodium hydride, potassium hydride and calcium hydride, inorganic bases such as sodium carbonate and potassium carbonate, acetates such as sodium acetate, and organic bases such as triethylamine.

When the compound represented by the general formula (7-2) that is a disulfide body is used, the reaction is usually carried out in the presence of a reducing agent. Examples of the reducing agent include sodium hydroxymethanesulfinate.

In the reaction, the compound represented by the general formula (7-3) is usually used in a ratio of 1 to 10 mol, and the base is usually used in a ratio of 1 to 10 mol, based on 1 mol of the compound represented by the general formula (7-1). Also, when the compound represented by the general formula (7-2) that is a disulfide body is used, the compound represented by the general formula (7-3) is usually used in a ratio of 0.5 to 5 mol, the base is usually used in a ratio of 0.5 to 5 mol, and the reducing agent is usually used in a ratio of 0.5 to 5 mol, based on 1 mol of the compound represented by the general formula (7-2).

The reaction temperature is usually within the range of 0 to 100° C. The reaction time is usually within the range of 0.1 to 24 hours.

After completion of the reaction, the compound of the present invention represented by the general formula (1-1) can be isolated by extracting the reaction mixture with an organic solvent and subjecting the organic layer to post-treatment operations such as drying and concentration. The isolated compound of the present invention represented by the general formula (1-1) can be also further purified by chromatography, recrystallization, or the like.

(Production Method 8)

A method for producing, among the compounds of the present invention, the compound of the present invention represented by the general formula (1-1).

The compound of the present invention represented by the general formula (1-1) can be produced by reacting the compound represented by the general formula (7-2) with a Grignard reagent represented by the general formula (8-2) or an organic lithium reagent represented by the general formula (8-2).

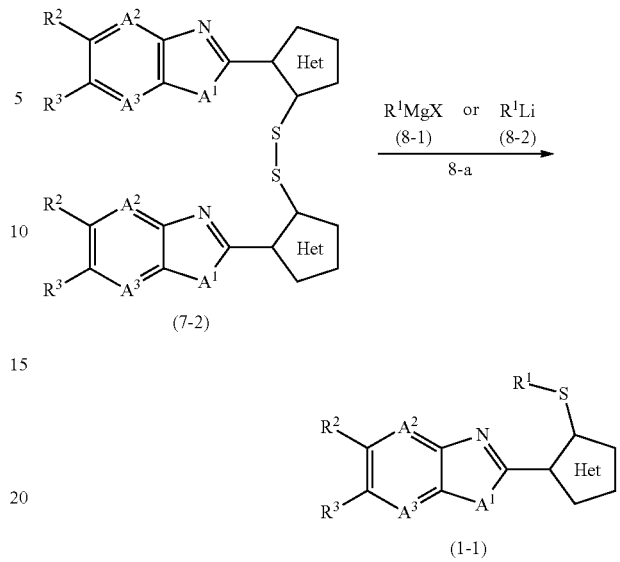

wherein $R^1$, $R^2$, $R^3$, $A^1$, $A^2$, $A^3$ and Het represent the same meaning as described above, and X represents a chlorine atom, a bromine atom or an iodide atom.

Step (8-a)

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

In the reaction, a compound represented by the general formula (8-1) is usually used in a ratio of 0.5 to 2 mol, based on 1 mol of the compound represented by the general formula (7-2). Also, when the compound represented by the general formula (8-2) is used, the compound represented by the general formula (8-2) is usually used in a ratio of 0.5 to 2 mol, based on 1 mol of the compound represented by the general formula (7-2).

The reaction temperature is usually within the range of −80 to 100° C. The reaction time is usually within the range of 0.1 to 24 hours.

After completion of the reaction, the compound of the present invention represented by the general formula (1-1) can be isolated by extracting the reaction mixture with an organic solvent and subjecting the organic layer to post-treatment operations such as drying and concentration. The isolated compound of the present invention represented by the general formula (1-1) can be also further purified by chromatography, recrystallization, or the like.

(Production Method 9)

A method for producing, among the compounds of the present invention, the compound of the present invention wherein $A^1$ is $NR^9$.

A compound of the present invention represented by the general formula (9-3) can be produced by reacting a compound of the present invention represented by the general formula (9-1) with a compound represented by the general formula (9-2), in the presence of a base.

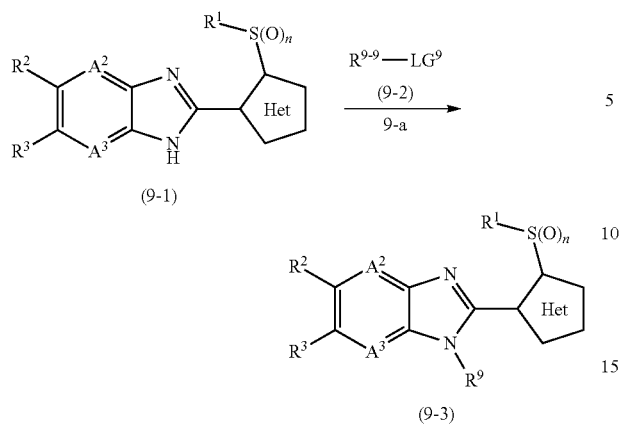

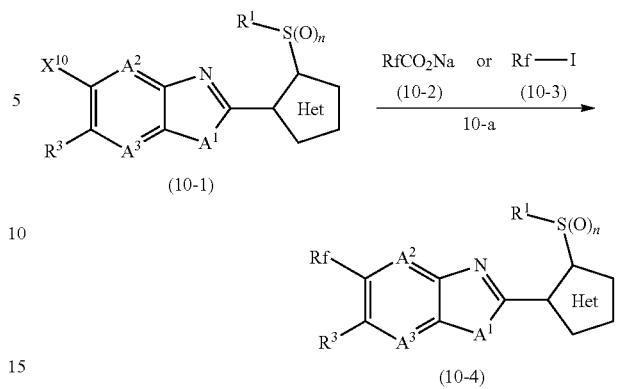

wherein $R^1$, $R^2$, $R^3$, $A^1$, $A^2$, $A^3$, n and Het represent the same meaning as described above, $LG^9$ represents a leaving group such as a chlorine atom, a bromine atom, an iodine atom, a methanesulfonyloxy group, a p-toluenesulfonyloxy atom, or a trifluoromethanesulfonyloxy group, and $R^{9-9}$ represents any group other than hydrogen atom of $R^9$ in the general formula (1).

Step (9-a)

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

Examples of the base include hydrides of alkali metals or alkaline earth metals such as sodium hydride, potassium hydride and calcium hydride, inorganic bases such as sodium carbonate and potassium carbonate, and organic bases such as triethylamine.

In the reaction, the compound represented by the general formula (9-2) is usually used in a ratio of 1 to 5 mol, and the base is usually used in a ratio of 1 to 3 mol, based on 1 mol of the compound of the present invention represented by the general formula (9-1).

The reaction temperature is usually within the range of 0 to 100° C. The reaction time is usually within the range of 0.1 to 24 hours.

After completion of the reaction, the compound of the present invention represented by the general formula (9-3) can be isolated by extracting the reaction mixture with an organic solvent and subjecting the organic layer to post-treatment operations such as drying and concentration. The isolated compound of the present invention represented by the general formula (9-3) can be also further purified by chromatography, recrystallization, or the like.

(Production Method 10)

A method for producing, among the compounds of the present invention, the compound of the present invention wherein $R^2$ is a C1 to C6 perfluoroalkyl group.

A compound of the present invention represented by the general formula (10-4) can be produced by reacting a compound of the present invention represented by the general formula (10-1) with a compound represented by the general formula (10-2) or a compound represented by the general formula (10-3), in the presence of copper or a copper compound.

wherein $R^1$, $R^3$, $A^1$, $A^2$, $A^3$, n and Het represent the same meaning as described above, $X^{10}$ represents a bromine atom or an iodine atom, and Rf represents a C1 to C6 perfluoroalkyl group.

Step (10-a)

The reaction is usually carried out in the presence of a solvent. Examples of the solvent include aromatic hydrocarbons such as toluene and xylene, acid amides such as DMF and NMP, and mixtures thereof.

Examples of the copper compound include copper(I) iodide.

In the reaction, when the compound represented by the general formula (10-2) is used, the compound represented by the general formula (10-2) is usually used in a ratio of 1 to 10 mol, and copper or the copper compound is usually used in a ratio of 0.5 to 10 mol, based on 1 mol of the compound of the present invention represented by the general formula (10-1). The reaction temperature is usually within the range of 100 to 200° C. The reaction time is usually within the range of 0.5 to 48 hours.

In the reaction, when the compound represented by the general formula (10-3) is used, potassium fluoride may be added. The compound represented by the general formula (10-3) is usually used in a ratio of 1 to 10 mol, copper or the copper compound is usually used in a ratio of 0.1 to 10 mol, and potassium fluoride is usually used in a ratio of 0.1 to 5 mol, based on 1 mol of the compound of the present invention represented by the general formula (10-1). The reaction temperature is usually within the range of 0 to 150° C. The reaction time is usually within the range of 0.5 to 48 hours.

After completion of the reaction, the compound of the present invention represented by the general formula (10-4) can be isolated by extracting the reaction mixture with an organic solvent and subjecting the organic layer to post-treatment operations such as drying and concentration. The isolated compound of the present invention represented by the general formula (10-4) can be also further purified by chromatography, recrystallization, or the like.

(Production Method 11)

A method for producing, among the compounds of the present invention, the compound of the present invention wherein $R^2$ is SH.

A compound of the present invention represented by the general formula (11-2) can be produced through steps (11-a) and step (11-b), as the following scheme.

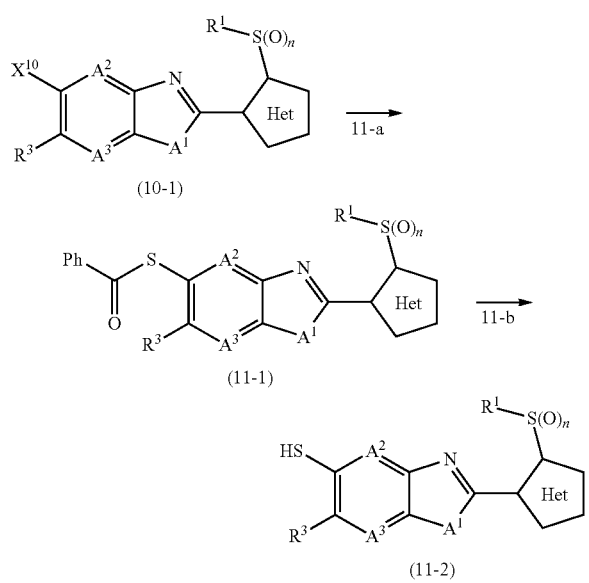

wherein $R^1$, $R^3$, $A^1$, $A^2$, $A^3$, n and Het represent the same meaning as described above, and $X^{10}$ represents a bromine atom or an iodine atom.

Step (11-a)

A compound represented by the general formula (11-1) can be produced by reacting the compound of the present invention represented by the general formula (10-1) with a thioesterifying agent, in the presence of a catalyst.

The reaction is usually carried out in the presence of a solvent. Examples of the solvent include aromatic hydrocarbons such as toluene and xylene, acid amides such as DMF and NMP, sulfoxides such as DMSO, and mixtures thereof.

Examples of the thioesterifying agent include thiobenzoic acid and the like. Examples of the catalyst include copper(I) chloride, copper(I) bromide, and copper(I) iodide. The reaction can be also carried out by adding a ligand as necessary. Examples of the ligand include acetylacetone, salen, and phenanthroline.

The reaction can be also carried out in the presence of a base, as necessary. Examples of the base include potassium carbonate, cesium carbonate, tripotassium phosphate, and triethylamine.

In the reaction, the thioesterifying agent is usually used in a ratio of 1 to 10 mol, the catalyst usually used in a ratio of 0.1 to 5 mol, the ligand is usually used in a ratio of 0.1 to 5 mol, and the base is usually used in a ratio of 1 to 2 mol, based on 1 mol of the compound of the present invention represented by the general formula (10-1).

The reaction temperature is usually within the range of 50 to 200° C. The reaction time is usually within the range of 0.5 to 24 hours.

After completion of the reaction, the compound represented by the general formula (11-1) can be isolated by extracting the reaction mixture with an organic solvent and subjecting the organic layer to post-treatment operations such as drying and concentration. The isolated compound represented by the general formula (11-1) can be also further purified by chromatography, recrystallization, or the like.

Step (11-b)

The compound of the present invention represented by the general formula (11-2) can be produced by hydrolyzing the compound represented by the general formula (11-1).

When hydrolyzed by an acid, the reaction is usually carried out using an aqueous solution of an acid as a solvent.

Examples of the acid include mineral acids such as hydrochloric acid, nitric acid, phosphoric acid and sulfuric acid, carboxylic acids such as acetic acid and trifluoroacetic acid.

The reaction temperature of acid hydrolysis is usually within the range of 0 to 100° C. The reaction time is usually within the range of 0.1 to 24 hours.

After completion of the reaction, the compound of the present invention represented by the general formula (11-2) can be isolated by extracting the reaction mixture with an organic solvent and subjecting the organic layer to post-treatment operations such as drying and concentration. The isolated compound of the present invention represented by the general formula (11-2) can be also further purified by chromatography, recrystallization, or the like.

When hydrolyzed by a base, the reaction is usually carried out in the presence of a solvent. Examples of the solvent include ethers such as THF, ethylene glycol dimethyl ether, tert-butyl methyl ether and 1,4-dioxane, alcohols such as methanol and ethanol, water, and mixtures thereof.

Examples of the base include alkali metal hydroxides such as sodium hydroxide and potassium hydroxide.

In the reaction, the base is usually used in a ratio of 1 to 10 mol, based on 1 mol of the compound represented by the general formula (11-1).

The reaction temperature is usually within the range of 0 to 120° C. The reaction time is usually within the range of 0.1 to 24 hours.

After completion of the reaction, the compound of the present invention represented by the general formula (11-2) can be isolated by acidifying the reaction solution, then extracting the reaction mixture with an organic solvent, and subjecting the organic layer to post-treatment operations such as drying and concentration. The isolated compound of the present invention represented by the general formula (11-2) can be also further purified by chromatography, recrystallization, or the like.

(Production Method 12)

A method for producing, among the compounds of the present invention, the compound of the present invention wherein $R^2$ is $S(O)_q R^{14-12}$.

A compound represented by the general formula (12-2) can be produced by reacting the compound of the present invention represented by the general formula (11-2) or a compound represented by the general formula (12-1) that is a disulfide body thereof with a compound represented by the general formula (12-4). Also, a compound of the present invention (12-3) can be produced by oxidizing the compound represented by the general formula (12-2).

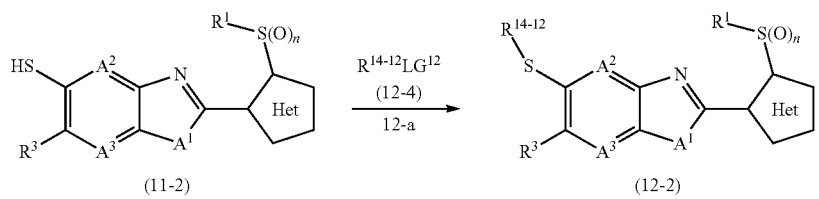

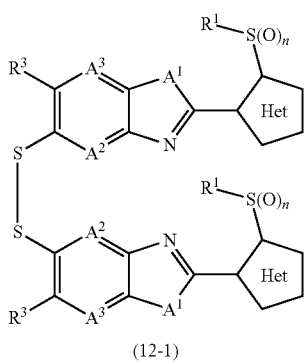
(12-1)

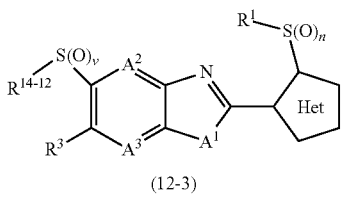
(12-3)

wherein $R^1$, $R^3$, $A^1$, $A^2$, $A^3$, n and Het represent the same meaning as described above, $R^{14\text{-}12}$ represents any group other than hydrogen atom of $R^{14}$ in the general formula (1), $LG^{12}$ represents a leaving group such as a chlorine atom, a bromine atom, an iodine atom, a methanesulfonyloxy group, a p-toluenesulfonyloxy atom, or a trifluoromethanesulfonyloxy group, and V is 1 or 2.

Step (12-a)

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

Examples of the base include hydrides of alkali metals or alkaline earth metals such as sodium hydride, potassium hydride and calcium hydride, inorganic bases such as sodium carbonate and potassium carbonate, and organic bases such as triethylamine.

When the compound represented by the general formula (12-1) that is a disulfide body is used, the reaction is usually carried out in the presence of a reducing agent. Examples of the reducing agent include sodium hydroxymethanesulfinate.

In the reaction, the compound represented by the general formula (12-4) is usually used in a ratio of 1 to 10 mol, and the base is usually used in a ratio of 1 to 10 mol, based on 1 mol of the compound of the present invention represented by the general formula (11-2).

Also, when the compound represented by the general formula (12-1) that is a disulfide body is used, the compound represented by the general formula (12-4) is usually used in a ratio of 0.5 to 5 mol, the base is usually used in a ratio of 0.5 to 5 mol, and the reducing agent is usually used in a ratio of 0.5 to 5 mol, based on 1 mol of the compound represented by the general formula (12-1).

The reaction temperature is usually within the range of 0 to 100° C. The reaction time is usually within the range of 0.1 to 24 hours.

After completion of the reaction, the compound of the present invention represented by the general formula (12-2) can be isolated by extracting the reaction mixture with an organic solvent and subjecting the organic layer to post-treatment operations such as drying and concentration. The isolated compound of the present invention represented by the general formula (12-2) can be also further purified by chromatography, recrystallization, or the like.

Step (12-b)

The compound of the present invention represented by the general formula (12-3) can be produced by reacting the compound of the present invention represented by the general formula (12-2) with an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

The reaction can be also carried out, in the presence of a catalyst, as necessary. Examples of the catalyst include sodium tungstate.

In the reaction, the oxidizing agent is usually used in a ratio of 1 to 5 mol, and the catalyst is usually used in a ratio of 0.01 to 0.5 mol, based on 1 mol of the compound of the present invention represented by the general formula (12-2).

In the compound of the present invention represented by the general formula (12-3) in which V is 1, the oxidizing agent is usually used in a ratio of 0.8 to 1.2 mol, based on 1 mol of the compound of the present invention represented by the general formula (12-2), and in the compound of the present invention represented by the general formula (12-3) in which V is 2, the oxidizing agent is usually used in a ratio of 1.8 to 5 mol, based on 1 mol of the compound of the present invention represented by the general formula (12-2).

The reaction temperature is usually within the range of −20 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and is subjected to post-treatment operations such as drying and concentration, whereby the compound of the present invention represented by the general formula (12-3) can be isolated. The isolated compound of the present invention represented by the general formula (12-3) also can be further purified by chromatography, recrystallization, or the like.

(Production Method 13)

A method for producing, among the compounds of the present invention, a compound of the present invention represented by the general formula (13-2) wherein $R^2$ is $-OR^{14}$.

The compound of the present invention represented by the general formula (13-2) can be produced by reacting a compound of the present invention represented by the general formula (13-1) with a compound represented by the general formula (13-3), in the presence of a base.

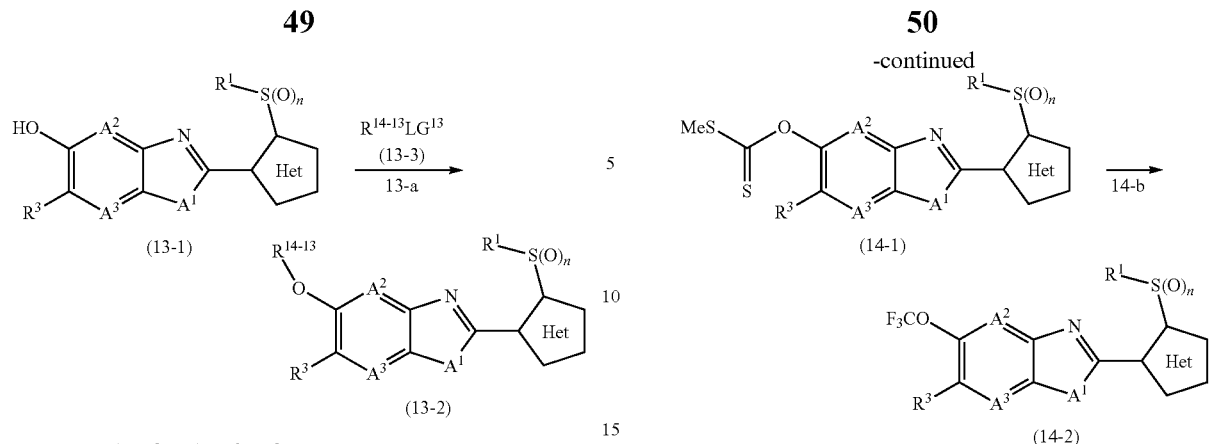

wherein $R^1$, $R^3$, $A^1$, $A^2$, $A^3$, n and Het represent the same meaning as described above, $R^{14-13}$ represents any group other than hydrogen atom of $R^{14}$ in the general formula (1), and $LG^{13}$ represents a leaving group such as a chlorine atom, a bromine atom, an iodine atom, a methanesulfonyloxy group, a p-toluenesulfonyloxy atom, or a trifluoromethanesulfonyloxy group.

Step (13-a)

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

Examples of the base include hydrides of alkali metals or alkaline earth metals such as sodium hydride, potassium hydride and calcium hydride, inorganic bases such as sodium carbonate and potassium carbonate, and organic bases such as triethylamine.

In the reaction, the compound represented by the general formula (13-3) is usually used in a ratio of 1 to 10 mol, and the base is usually used in a ratio of 1 to 10 mol, based on 1 mol of the compound of the present invention represented by the general formula (13-1).

The reaction temperature is usually within the range of 0 to 100° C. The reaction time is usually within the range of 0.1 to 24 hours.

After completion of the reaction, the compound of the present invention represented by the general formula (13-2) can be isolated by extracting the reaction mixture with an organic solvent and subjecting the organic layer to post-treatment operations such as drying and concentration. The isolated compound of the present invention represented by the general formula (13-2) can be also further purified by chromatography, recrystallization, or the like.

(Production Method 14)

A method for producing, among the compounds of the present invention, the compound of the present invention wherein $R^2$ is a trifluoromethoxy group.

The compound of the present invention represented by the general formula (14-2) can be produced through steps (14-a) and step (14-b), as the following scheme.

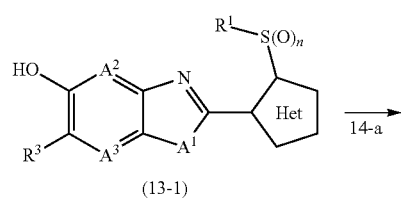

wherein $R^1$, $R^3$, $A^1$, $A^2$, $A^3$, n and Het represent the same meaning as described above.

Step (14-a)

A compound represented by the general formula (14-1) can be produced by reacting the compound of the present invention represented by the general formula (13-1) with a base, carbon disulfide and a methylating agent.

The reaction is carried out in the presence of a solvent. Examples of the solvent include acid amides such as DMF and NMP and sulfoxides such as DMSO.

Examples of the base include alkali metal hydrides such as sodium hydride.

Examples of the methylating agent include methyl iodide.

In the reaction, the base is usually used in a ratio of 1 to 2 mol, carbon disulfide is usually used in a ratio of 1 to 10 mol, and the methylating agent is usually used in a ratio of 1 to 10 mol, based on 1 mol of the compound of the present invention represented by the general formula (13-1).

The reaction temperature is usually within the range of 0 to 100° C. The reaction time is usually within the range of 0.5 to 24 hours.

After completion of the reaction, the compound represented by the general formula (14-1) can be isolated by extracting the reaction mixture with an organic solvent and subjecting the organic layer to post-treatment operations such as drying and concentration. The isolated compound represented by the general formula (14-1) can be also further purified by chromatography, recrystallization, or the like.

Step (14-b)

The compound of the present invention represented by the general formula (14-2) can be produced by reacting the compound represented by the general formula (14-1) with a fluorinating agent, in the presence of a base.

The reaction is carried out in the presence of a solvent. Examples of the solvent include halogenated hydrocarbons such as dichloromethane, chloroform, carbon tetrachloride, and 1,2-dichloroethane.

Examples of the base include 1,3-dibromo-5,5-dimethylhydantoin.

Examples of the fluorinating agent include tetra-n-butylammonium fluoride and a hydrogen fluoride pyridine complex.

In the reaction, the base is usually used in a ratio of 1 to 10 mol, and the fluorinating agent is usually used in a ratio of 1 to 10 mol, based on 1 mol of the compound represented by the general formula (14-1).

The reaction temperature is usually within the range of −80 to 50° C. The reaction time is usually within the range of 0.5 to 24 hours.

After completion of the reaction, the compound of the present invention represented by the general formula (14-2) can be isolated by extracting the reaction mixture with an organic solvent and subjecting the organic layer to post-treatment operations such as drying and concentration. The isolated compound of the present invention represented by the general formula (14-2) can be also further purified by chromatography, recrystallization, or the like.
(Production Method 15)

A method for producing, among the compounds of the present invention, an N-oxide wherein A³ is a nitrogen atom, and the nitrogen atom is oxidized.

The N-oxide can be produced according to a known method (for example, Organic Syntheses, Coll. Vol. 4, p. 828).
(Production Method 16)

A method for producing, among the compounds of the present invention, the compound of the present invention wherein Het is H4.

A compound of the present invention represented by the general formula (16-3) can be produced through steps (16-a) and (16-b) or by reacting a compound represented by the general formula (16-1) with a compound represented by the general formula (16-5), in the presence of a base, as the following scheme.

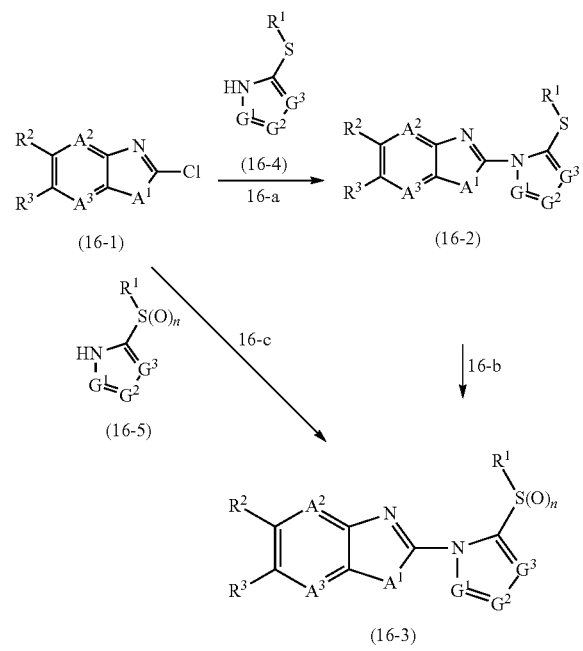

wherein R¹, R², R³, A¹, A², A³, G¹, G², G³ and n represent the same meaning as described above.
Step (16-a)

A compound of the present invention represented by the general formula (16-2) can be produced by reacting the compound represented by the general formula (16-1) with a compound represented by the general formula (16-4), in the presence of a base.

The reaction is carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

Examples of the base include hydrides of alkali metals or alkaline earth metals such as sodium hydride, potassium hydride and calcium hydride, inorganic bases such as sodium carbonate and potassium carbonate, acetates such as sodium acetate, and organic bases such as triethylamine.

In the reaction, the compound represented by the general formula (16-4) is usually used in a ratio of 1 to 2 mol, and the base is usually used in a ratio of 1 to 10 mol, based on 1 mol of the compound of the present invention represented by the general formula (16-1).

The reaction temperature is usually within the range of 0 to 100° C. The reaction time is usually within the range of 0.1 to 24 hours.

After completion of the reaction, the compound of the present invention represented by the general formula (16-2) can be isolated by extracting the reaction mixture with an organic solvent and subjecting the organic layer to post-treatment operations such as drying and concentration. The isolated compound of the present invention represented by the general formula (16-2) can be also further purified by chromatography, recrystallization, or the like.
Step (16-b)

The compound of the present invention represented by the general formula (16-3) can be produced by reacting the compound of the present invention represented by the general formula (16-2) with an oxidizing agent.

The reaction is usually carried out in the presence of a solvent. Examples of the solvent include aliphatic halogenated hydrocarbons such as dichloromethane and chloroform, alcohols such as methanol and ethanol, acetic acid, water, and mixtures thereof.

Examples of the oxidizing agent include m-chloroperbenzoic acid and aqueous hydrogen peroxide.

The reaction can be also carried out, in the presence of a catalyst, as necessary. Examples of the catalyst include sodium tungstate.

In the reaction, the oxidizing agent is usually used in a ratio of 1 to 5 mol, and the catalyst is usually used in a ratio of 0.01 to 0.5 mol, based on 1 mol of the compound of the present invention represented by the general formula (16-2).

In the compound of the present invention represented by the general formula (16-3) in which n is 1, the oxidizing agent is usually used in a ratio of 0.8 to 1.2 mol, based on 1 mol of the compound of the present invention represented by the general formula (16-2), and in the compound of the present invention represented by the general formula (16-3) in which n is 2, the oxidizing agent is usually used in a ratio of 1.8 to 5 mol, based on 1 mol of the compound of the present invention represented by the general formula (16-2).

The reaction temperature is usually within the range of −20 to 120° C. The reaction time is usually within the range of 0.1 to 12 hours.

After completion of the reaction, the reaction mixture is extracted with an organic solvent, and the organic layer is washed with an aqueous solution of a reducing agent (for example, sodium sulfite, sodium thiosulfate) and an aqueous solution of a base (for example, sodium bicarbonate) as necessary, and is subjected to post-treatment operations such as drying and concentration, whereby the compound of the present invention represented by the general formula (16-3) can be isolated. The isolated compound of the present invention represented by the general formula (16-3) also can be further purified by chromatography, recrystallization, or the like.
Step (16-c)

The reaction is carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

Examples of the base include hydrides of alkali metals or alkaline earth metals such as sodium hydride, potassium hydride and calcium hydride, inorganic bases such as sodium carbonate and potassium carbonate, acetates such as sodium acetate, and organic bases such as triethylamine.

In the reaction, the compound represented by the general formula (16-5) is usually used in a ratio of 1 to 2 mol, and the base is usually used in a ratio of 1 to 10 mol, based on 1 mol of the compound of the present invention represented by the general formula (16-1).

The reaction temperature is usually within the range of 0 to 100° C. The reaction time is usually within the range of 0.1 to 24 hours.

After completion of the reaction, the compound of the present invention represented by the general formula (16-3) can be isolated by extracting the reaction mixture with an organic solvent and subjecting the organic layer to post-treatment operations such as drying and concentration. The isolated compound of the present invention represented by the general formula (16-3) can be also further purified by chromatography, recrystallization, or the like.

(Production Method 17)

A method for producing a compound of the present invention represented by the general formula (17-3) in which $R^2$ is an OH group.

The compound of the present invention represented by the general formula (17-3) can be produced through Step (17-a) and Step (17-b), as the following scheme.

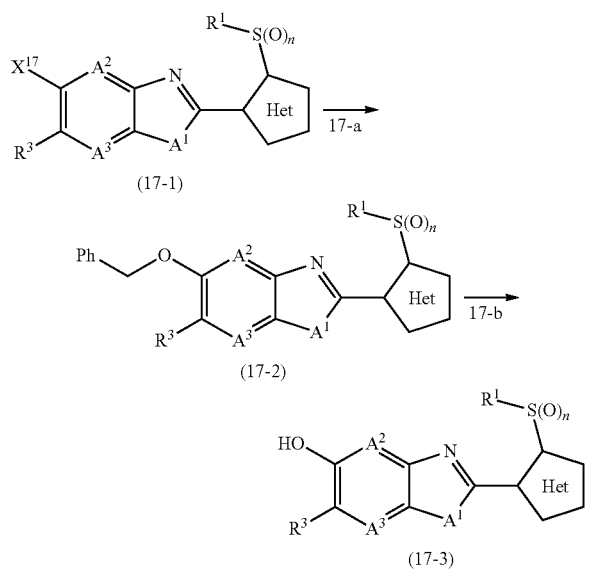

wherein $R^1$, $R^3$, $A^1$, $A^2$, $A^3$, Het and n represent the same meaning as described above, and $X^{17}$ represents a halogen atom.

Step (17-a)

A compound represented by the general formula (17-2) can be produced by reacting the compound of the present invention represented by the general formula (17-2) with benzyl alcohol, in the presence of a base.

The reaction is usually carried out in the presence of a solvent or using benzyl alcohol as a solvent. Examples of the solvent include aromatic hydrocarbons such as toluene and xylene, acid amides such as DMF and NMP, sulfoxides such as DMSO, and mixtures thereof.

The reaction can be also carried out by adding a catalyst, as necessary. Examples of the catalyst include copper(I) chloride, copper(I) bromide, and copper(I) iodide.

The reaction can be also carried out by adding a ligand as necessary. Examples of the ligand include acetylacetone, salen, and phenanthroline.

The reaction is usually carried out in the presence of a base. Examples of the base include potassium carbonate, cesium carbonate, and tripotassium phosphate.

In the reaction, benzyl alcohol is usually used in a ratio of 1 to 10 mol, the catalyst is usually used in a ratio of 0.1 to 5 mol, the ligand is usually used in a ratio of 0.1 to 5 mol, and the base is usually used in a ratio of 1 to 2 mol, based on 1 mol of the compound of the present invention represented by the general formula (17-3).

The reaction temperature is usually within the range of 50 to 200° C. The reaction time is usually within the range of 0.5 to 24 hours.

After completion of the reaction, the compound represented by the general formula (17-2) can be isolated by extracting the reaction mixture with an organic solvent and subjecting the organic layer to post-treatment operations such as drying and concentration. The isolated compound represented by the general formula (17-2) can be also further purified by chromatography, recrystallization, or the like.

Step (17-b)

The compound of the present invention represented by the general formula (17-3) can be produced by reacting the compound represented by the general formula (17-2) with hydrogen, in the presence of a hydrogenation catalyst.

The reaction is usually carried out in the presence of a solvent, usually in a hydrogen atmosphere of 1 to 100 atmospheric pressure. Examples of the solvent include ethers such as THF, ethylene glycol dimethyl ether, tert-butyl methyl ether and 1,4-dioxane, esters such as ethyl acetate and butyl acetate, alcohols such as methanol and ethanol, water, and mixtures thereof.

Examples of the hydrogenation catalyst include transition metal compounds such as palladium carbon, palladium hydroxide, Raney nickel, and platinum oxide.

In the reaction, hydrogen is usually used in a ratio of 3 mol, and the hydrogenation catalyst is usually used in a ratio of 0.001 to 0.5 mol, based on 1 mol of the compound represented by the general formula (17-2).

The reaction can be also carried out by adding an acid, a base or the like, as necessary.

Examples of the acid include acetic acid and hydrochloric acid, and examples of the base include tertiary amines such as triethylamine, and magnesium oxide.

The reaction temperature is usually within the range of −20 to 100° C. The reaction time is usually within the range of 0.1 to 24 hours.

After completion of the reaction, the compound of the present invention represented by the general formula (17-3) can be isolated by filtering the reaction mixture, extracting the reaction mixture with an organic solvent as necessary, and subjecting the organic layer to post-treatment operations such as drying and concentration. The isolated compound of the present invention represented by the general formula (17-3) can be also further purified by chromatography, recrystallization, or the like.

Next, a method for producing a production intermediate of the compound of the present invention will be described. A part of the intermediates used for the production of the present active compound is commercialized, or is a compound disclosed in a known document, etc. The intermediate of the present invention can be produced, for example, by the following method.

Reference Production Method A

A method for producing the compound represented by the general formula (A-4).

The compound represented by the general formula (A-4) can be produced through step (A-a) and step (A-c) or through step (A-b) and step (A-c), as the following scheme.

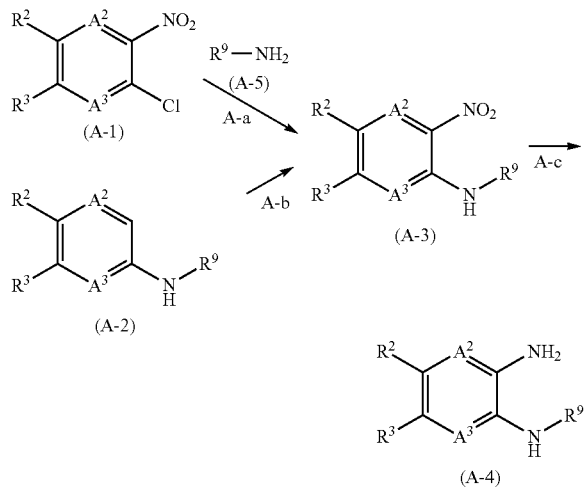

wherein $R^2$, $R^3$, $R^9$, $A^2$ and $A^3$ represent the same meaning as described above.

Step (A-a)

A compound represented by the general formula (A-3) can be produced by reacting a compound represented by the general formula (A-1) with a compound represented by the general formula (A-5).

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

The reaction can be also carried out by adding a base, as necessary. Examples of the base include alkali metal hydrides such as sodium hydride, alkali metal carbonates such as sodium carbonate and potassium carbonate, tertiary amines such as triethylamine and diisopropylethylamine, and nitrogen-containing aromatic compounds such as pyridine and 4-dimethylaminopyridine.

In the reaction, the compound represented by the general formula (A-5) is usually used in a ratio of 1 to 10 mol, and the base is usually used in a ratio of 1 to 10 mol, based on 1 mol of the compound represented by the general formula (A-1).

The reaction temperature is usually within the range of 0 to 150° C. The reaction time is usually within the range of 0.5 to 24 hours.

After completion of the reaction, the compound represented by the general formula (A-3) can be isolated by extracting the reaction mixture with an organic solvent and subjecting the organic layer to post-treatment operations such as drying and concentration. The isolated compound represented by the general formula (A-3) can be also further purified by chromatography, recrystallization, or the like.

Step (A-b)

The compound represented by the general formula (A-3) can be produced by reacting a compound represented by the general formula (A-2) with a nitrating agent.

The reaction is usually carried out in the presence of a solvent. Examples of the solvent include aliphatic halogenated hydrocarbons such as dichloromethane and chloroform, acetic acid, concentrated sulfuric acid, concentrated nitric acid, water, and mixtures thereof.

Examples of the nitrating agent include concentrated nitric acid and the like.

In the reaction, the nitrating agent is usually used in a ratio of 1 to 3 mol, based on 1 mol of the compound represented by the general formula (A-2).

The reaction temperature is usually within the range of −10 to 100° C. The reaction time is usually within the range of 0.1 to 24 hours.

After completion of the reaction, the compound represented by the general formula (A-3) can be isolated by pouring water to the reaction mixture and extracting the mixture with an organic solvent and subjecting the organic layer to post-treatment operations such as drying and concentration. The isolated compound represented by the general formula (A-3) can be also further purified by chromatography, recrystallization, or the like.

In addition, when $R^9$ is a hydrogen atom in the compound represented by the general formula (A-3), the compound in which $R^9$ is other than a hydrogen atom in the compound represented by the general formula (A-3) can be produced, using the compound represented by the general formula (A-3) in which $R^9$ is a hydrogen atom in place of the compound of the present invention represented by the general formula (9-1), in accordance with the method of Production Method 9.

Step (A-c)

The compound represented by the general formula (A-4) can be produced by reacting the compound represented by the general formula (A-3) with hydrogen, in the presence of a hydrogenation catalyst.

The reaction is usually carried out in the presence of a solvent, usually in a hydrogen atmosphere of 1 to 100 atmospheric pressure. Examples of the solvent include ethers such as THF, ethylene glycol dimethyl ether, tert-butyl methyl ether and 1,4-dioxane, esters such as ethyl acetate and butyl acetate, alcohols such as methanol and ethanol, water, and mixtures thereof.

Examples of the hydrogenation catalyst include transition metal compounds such as palladium carbon, palladium hydroxide, Raney nickel, and platinum oxide.

In the reaction, hydrogen is usually used in a ratio of 3 mol, and the hydrogenation catalyst is usually used in a ratio of 0.001 to 0.5 mol, based on 1 mol of the compound represented by the general formula (A-3).

The reaction can be also carried out by adding an acid, a base or the like, as necessary.

Examples of the acid include acetic acid, hydrochloric acid, and the like, and examples of the base include tertiary amines such as triethylamine, magnesium oxide, and the like.

The reaction temperature is usually within the range of −20 to 100° C. The reaction time is usually within the range of 0.1 to 24 hours.

After completion of the reaction, the compound represented by the general formula (A-4) can be isolated by filtering the reaction mixture, extracting the reaction mixture with an organic solvent as necessary, and subjecting the organic layer to post-treatment operations such as drying and concentration. The isolated compound represented by the general formula (A-4) can be also further purified by chromatography, recrystallization, or the like.

Reference Production Method B

A method for producing the compound represented by the general formula (A-3).

The compound represented by the general formula (A-3) can be produced through step (B-a), step (B-b) and step (B-c), as the following scheme.

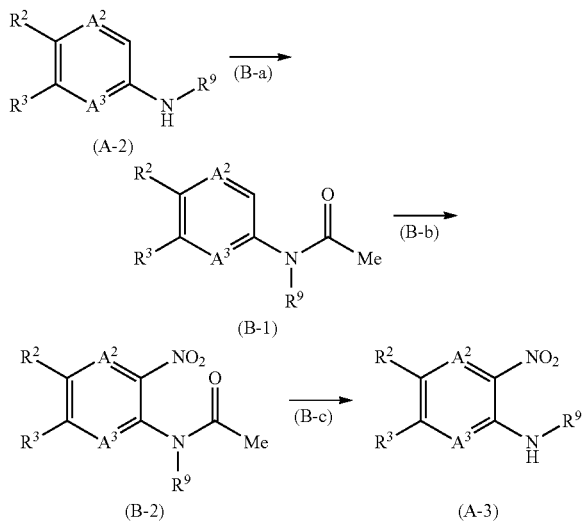

wherein $R^2$, $R^3$, $R^9$, $A^2$ and $A^3$ represent the same meaning as described above.

Step (B-a)

A compound represented by the general formula (B-1) can be produced by reacting the compound represented by the general formula (A-2) with an acylating agent.

The reaction is usually carried out in the presence of a solvent or using an acylating agent as a solvent. Examples of the solvent include aliphatic halogenated hydrocarbons such as dichloromethane and chloroform, ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, acetic anhydride, and mixtures thereof.

Examples of the acylating agent include acetic anhydride and p-acetoxynitrobenzene.

The reaction can be also carried out by adding a base, as necessary. Examples of the base include tertiary amines such as triethylamine and diisopropylethylamine and nitrogen-containing aromatic compounds such as pyridine and 4-dimethylaminopyridine.

In the reaction, the acetylating agent is usually used in a ratio of 1 mol or more, and the base is usually used in a ratio of 0 to 10 mol, based on 1 mol of the compound represented by the general formula (A-2).

The reaction temperature is usually within the range of 0 to 150° C. The reaction time is usually within the range of 0.5 to 24 hours.

After completion of the reaction, the compound represented by the general formula (B-1) can be isolated by extracting the reaction mixture with an organic solvent and subjecting the organic layer to post-treatment operations such as drying and concentration. The isolated compound represented by the general formula (B-1) can be also further purified by chromatography, recrystallization, or the like.

Step (B-b)

A compound represented by the general formula (B-2) can be produced, using the compound represented by the general formula (B-1) in place of the compound represented by the general formula (A-2), in accordance with step (A-b) of Reference Production Example A.

Step (B-c)

The compound represented by the general formula (A-3) can be produced by hydrolyzing the compound represented by the general formula (B-2), in the presence of an acid or a base.

When hydrolyzed by an acid, the reaction is usually carried out using an aqueous solution of an acid as a solvent. Examples of the acid include mineral acids such as hydrochloric acid and sulfuric acid, carboxylic acids such as acetic acid and trifluoroacetic acid.

The reaction temperature is usually within the range of 0 to 100° C. The reaction time is usually within the range of 0.1 to 24 hours.

After completion of the reaction, the compound represented by the general formula (A-3) can be isolated by extracting the reaction mixture with an organic solvent and subjecting the organic layer to post-treatment operations such as drying and concentration. The isolated compound represented by the general formula (A-3) can be also further purified by chromatography, recrystallization, or the like.

When hydrolyzed by a base, the reaction is usually carried out in the presence of a solvent. Examples of the solvent include ethers such as THF, ethylene glycol dimethyl ether, tert-butyl methyl ether and 1,4-dioxane, alcohols such as methanol and ethanol, water, and mixtures thereof.

Examples of the base include alkali metal hydroxides such as sodium hydroxide and potassium hydroxide and hydrazine.

In the reaction, the base is usually used in a ratio of 1 to 10 mol, based on 1 mol of the compound represented by the general formula (B-2).

The reaction temperature is usually within the range of 0 to 120° C. The reaction time is usually within the range of 0.1 to 24 hours.

After completion of the reaction, the compound represented by the general formula (A-3) can be isolated by acidifying the reaction solution, then extracting the reaction mixture with an organic solvent and subjecting the organic layer to post-treatment operations such as drying and concentration. The isolated compound represented by the general formula (A-3) can be also further purified by chromatography, recrystallization, or the like.

Reference Production Method C

A method for producing the compound represented by the general formula (A-4).

The compound represented by the general formula (A-4) can be produced through step (C-a) and step (C-b), as the following scheme.

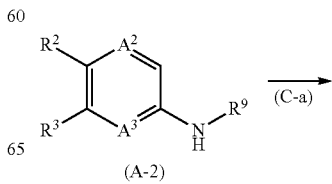

wherein $R^2$, $R^3$, $R^9$, $A^2$ and $A^3$ represent the same meaning as described above.

Step (C-a)

A compound represented by the general formula (C-1) can be produced by reacting the compound represented by the general formula (A-2) with a brominating agent.

The reaction is usually carried out in the presence of a solvent. Examples of the solvent include water, acetic acid, ethers such as 1,4-dioxane, diethyl ether and THF, esters such as ethyl acetate and butyl acetate, halogenated hydrocarbons such as dichloromethane, chloroform, carbon tetrachloride and 1,2-dichloroethane, nitriles such as acetonitrile, aprotic polar solvents such as DMF and NMP, and mixtures thereof.

Examples of the brominating agent include N-bromosuccinimide and bromine.

The brominating agent is usually used in a ratio of 1 to 3 mol, based on 1 mol of the compound represented by the general formula (A-2).

The reaction temperature is usually within the range of −10 to 100° C. The reaction time is usually within the range of 0.1 to 24 hours.

After completion of the reaction, the compound represented by the general formula (C-1) can be isolated by pouring the reaction mixture into water, then extracting the mixture with an organic solvent, and concentrating the organic layer; collecting a solid generated by pouring the reaction mixture into water by filtration; or collecting a solid generated in the reaction mixture by filtration. The isolated compound represented by the general formula (C-1) can be also further purified by recrystallization, chromatography, or the like.

Step (C-b)

The compound represented by the general formula (A-4) can be produced by reacting the compound represented by the general formula (C-1) with an aminating agent, in the presence of copper or a copper compound.

The reaction is usually carried out in the presence of a solvent. Examples of the solvent include water, alcohols such as methanol and ethanol, ethers such as 1,4-dioxane, diethyl ether and THF, esters such as ethyl acetate and butyl acetate, halogenated hydrocarbons such as dichloromethane, chloroform, carbon tetrachloride and 1,2-dichloroethane, nitriles such as acetonitrile, aprotic polar solvents such as DMF, NMP and dimethyl sulfoxide, nitrogen-containing aromatic compounds such as pyridine and quinolone, and mixtures thereof.

Examples of the aminating agent include ammonia, aqueous ammonia, and lithium amide.

Examples of the copper compound include copper(I) iodide, copper(I) oxide, copper(II) oxide, acetylacetone copper(II), copper(II) acetate, and copper(II) sulfate.

The reaction can be also carried out by adding a ligand as necessary. Examples of the ligand include acetylacetone, salen, and phenanthroline.

The reaction can be also carried out by adding a base as necessary. Examples of the base include nitrogen-containing heterocyclic compounds such as pyridine, picoline, 2,6-lutidine, DBU and 1,5-diazabicyclo[4.3.0]-5-nonene, tertiary amines such as triethylamine and N-ethyldiisopropylamine, and inorganic bases such as tripotassium phosphate, potassium carbonate, cesium carbonate and sodium hydroxide.

The aminating agent is usually used in a ratio of 1 to 5 mol, copper or the copper compound is usually used in a ratio of 0.02 to 0.5 mol, the ligand is usually used in a ratio of 0.02 to 2 mol as necessary, and the base is usually used in a ratio of 1 to 5 mol as necessary, based on 1 mol of the compound represented by the general formula (C-1).

The reaction temperature is usually within the range of 30 to 200° C. The reaction time is usually within the range of 0.1 to 24 hours.

After completion of the reaction, the compound represented by the general formula (A-4) can be isolated by pouring water into the reaction mixture, then extracting the mixture with an organic solvent, and concentrating the organic layer; collecting a solid generated by pouring the reaction mixture into water by filtration; or collecting a solid generated in the reaction mixture by filtration. The isolated compound represented by the general formula (A-4) can be also further purified by recrystallization, chromatography, or the like.

Reference Production Method D

A method for producing a compound represented by the general formula (D-3).

The compound represented by the general formula (D-3) can be produced through step (D-a) and step (D-b), as the following scheme, wherein $R^2$, $R^3$, $A^2$ and $A^3$ represent the same meaning as described above.

Step (D-a)

A compound represented by the general formula (D-2) can be produced, using a compound represented by the general formula (D-1) in place of the compound represented by the general formula (A-2), in accordance with step (A-b) of General Production Example A.

Step (D-b)

The compound represented by the general formula (D-3) can be produced, using the compound represented by the general formula (D-2) in place of the compound represented by the general formula (A-3), in accordance with step (A-c) of General Production Example A.

Reference Production Method E

A method for producing the compound represented by the general formula (E-3).

The compound represented by the general formula (E-3) can be produced through step (E-a) and step (E-b), as the following scheme.

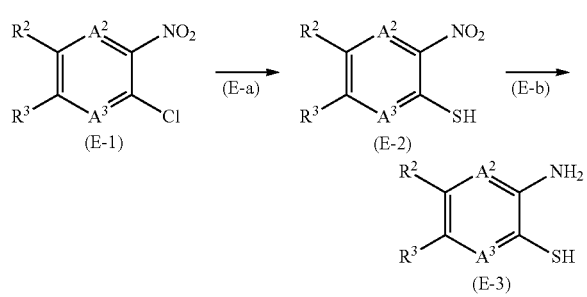

wherein $R^2$, $R^3$, $A^2$ and $A^3$ represent the same meaning as described above.

Step (E-a)

A compound represented by the general formula (E-2) can be produced by reacting a compound represented by the general formula (E-1) with thiourea, in the presence of a base.

The reaction is usually carried out in the presence of a solvent. Examples of the solvent include alcohols such as methanol and ethanol, water, and mixtures thereof.

Examples of the base include alkali metal hydroxides such as sodium hydroxide and potassium hydroxide.

In the reaction, thiourea is usually used in a ratio of 0.5 to 3 mol, and the base is usually used in a ratio of 1 to 10 mol, based on 1 mol of the compound represented by the general formula (E-1).

The reaction temperature is usually within the range of 0 to 100° C. The reaction time is usually within the range of 0.1 to 24 hours.

After completion of the reaction, the compound represented by the general formula (E-2) can be isolated by adding an acid to the reaction mixture, then extracting the mixture with an organic solvent and subjecting the organic layer to post-treatment operations such as drying and concentration. The isolated compound represented by the general formula (E-2) can be also further purified by chromatography, recrystallization, or the like.

Step (E-b)

The compound represented by the general formula (E-3) can be produced by reacting the compound represented by the general formula (E-2) with a reducing agent.

The reduction reaction can be carried out, for example, in the presence of a reducing agent; an acid such as hydrochloric acid and acetic acid; and water.

The reaction is usually carried out in the presence of a solvent. Examples of the solvent include ethers such as THF, ethylene glycol dimethyl ether, tert-butyl methyl ether and 1,4-dioxane, esters such as ethyl acetate and butyl acetate, alcohols such as methanol and ethanol, acid amides such as DMF and NMP, and mixtures thereof.

The reducing agent includes metal powder such as iron powder and zinc powder and tin dichloride.

In the reaction, the metal powder or tin dichloride is usually used in a ratio of 3 to 10 mol, based on 1 mol of the compound represented by the general formula (E-2).

The reaction temperature is usually within the range of 0 to 100° C. The reaction time is usually within the range of 0.1 to 24 hours.

After completion of the reaction, the compound represented by the general formula (E-3) can be isolated by adding water to the reaction mixture, then extracting the mixture with an organic solvent and subjecting the organic layer to post-treatment operations such as drying and concentration. The isolated compound represented by the general formula (E-3) can be also further purified by chromatography, recrystallization, or the like.

Reference Production Method F

A method for producing the compound represented by the general formula (12-1).

The compound represented by the general formula (12-1) can be produced through step (F-a) and step (F-b), as the following scheme.

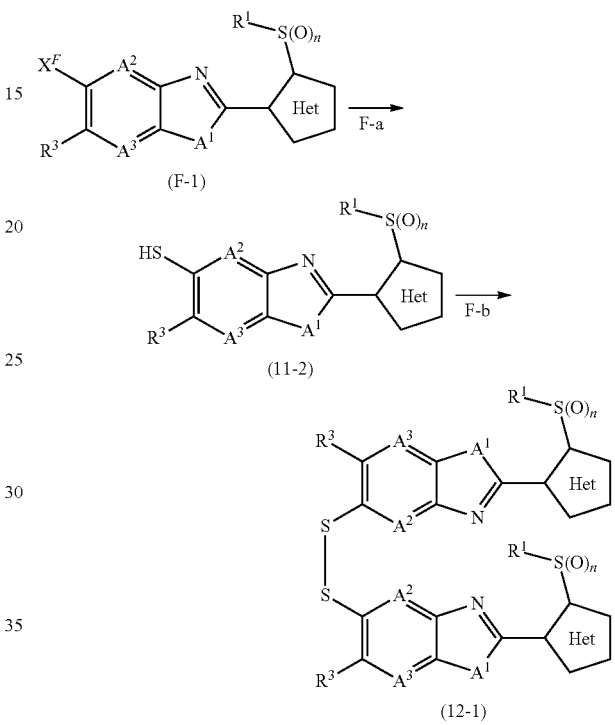

wherein $R^1$, $R^3$, $A^1$, $A^2$, $A^3$, n and Het represent the same meaning as described above, and $X^F$ represents a halogen atom.

Step (F-a)

The compound of the present invention represented by the general formula (11-2) can be produced by reacting a compound of the present invention represented by the general formula (F-1) with a thiolating agent, in the presence of a catalyst.

The reaction is usually carried out in the presence of a solvent. Examples of the solvent include aromatic hydrocarbons such as toluene and xylene, acid amides such as DMF and NMP, sulfoxides such as DMSO, and mixtures thereof.

Examples of the thiolating agent include sodium sulfide, sodium sulfide nonahydrate, and thiourea.

Examples of the catalyst include copper(I) chloride, copper(I) bromide, and copper(I) iodide.

The reaction can be also carried out by adding a ligand as necessary. Examples of the ligand include acetylacetone, salen, and phenanthroline.

The reaction can be also carried out by adding a base, as necessary. Examples of the base include potassium carbonate, cesium carbonate, tripotassium phosphate, and triethylamine.

The thiolating agent is usually used in a ratio of 1 to 10 mol, the catalyst is usually used in a ratio of 0.1 to 5 mol, the ligand is usually used in a ratio of 0.1 to 5 mol, and the base is usually used in a ratio of 1 to 2 mol, based on 1 mol of the compound of the present invention represented by the general formula (F-1).

The reaction temperature is usually within the range of 50 to 200° C. The reaction time is usually within the range of 0.5 to 24 hours.

After completion of the reaction, the compound of the present invention represented by the general formula (11-2) can be isolated by extracting the reaction mixture with an organic solvent and subjecting the organic layer to post-treatment operations such as drying and concentration. The isolated compound of the present invention represented by the general formula (11-2) can be also further purified by chromatography, recrystallization, or the like. Here, the reaction from the compound of the present invention represented by the general formula (11-2) to the compound represented by the general formula (12-1) is likely to occur, and the compound represented by the general formula (12-1) is sometimes produced during synthesis of the compound of the present invention represented by the general formula (11-2).

Step (F-b)

The compound represented by the general formula (12-1) can be produced by reacting the compound of the present invention represented by the general formula (11-2) with an oxidizing agent.

The reaction is usually carried out in the presence of a solvent. Examples of the solvent include water, alcohols such as methanol and ethanol, ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, carboxylic acids such as acetic acid, and mixtures thereof.

Examples of the oxidizing agent include oxygen, iodine, aqueous hydrogen peroxide, and potassium ferricyanide.

In the reaction, the oxidizing agent is usually used in a ratio of 0.5 to 10 mol, based on 1 mol of the compound of the present invention represented by the general formula (11-2).

The reaction temperature is usually within the range of 0 to 100° C. The reaction time is usually within the range of 0.1 to 24 hours.

After completion of the reaction, the compound represented by the general formula (12-1) can be isolated by extracting the reaction mixture with an organic solvent and subjecting the organic layer to post-treatment operations such as drying and concentration. The isolated compound represented by the general formula (12-1) can be also further purified by chromatography, recrystallization, or the like.

Reference Production Method G

A method for producing the compound represented by the general formula (5-1).

The compound represented by the general formula (5-1) can be produced by inducing a compound represented by the general formula (6-1) through step (G-a) or step (G-b), then undergoing step (G-c), or undergoing step (G-d) or step (G-e), as the following scheme.

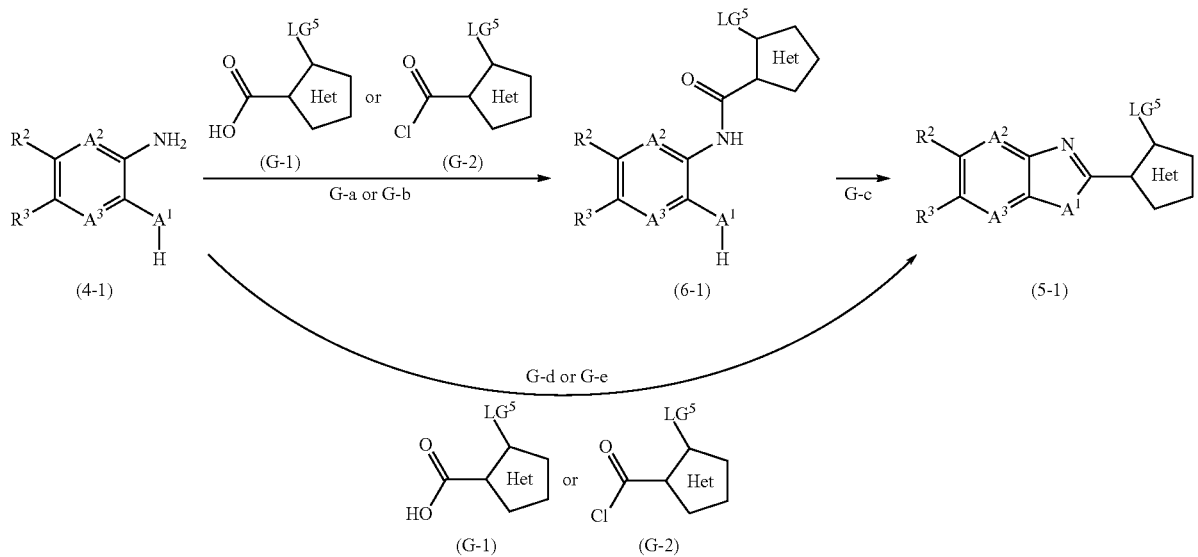

wherein $R^2$, $R^3$, $A^1$, $A^2$, $A^3$, $LG^5$ and Het represent the same meaning as described above.

Step (G-a)

A compound represented by the general formula (6-1) can be produced, using a compound represented by the general formula (G-1), in place of the compound represented by the general formula (2-4), in accordance with the method of step (2-a) of Production Method 2.

Step (G-b)

A compound represented by the general formula (6-1) can be produced, using a compound represented by the general formula (G-2), in place of the compound represented by the general formula (2-5), in accordance with the method of step (2-b) of Production Method 2.

Step (G-c)

A compound represented by the general formula (5-1) can be produced, using a compound represented by the general formula (6-1), in place of the compound represented by the general formula (2-2), in accordance with the method of step (2-c) of Production Method 2.

Step (G-d)

A compound represented by the general formula (5-1) can be produced, using the compound represented by the general formula (G-1), in place of the compound represented by the general formula (2-4), in accordance with the method of step (2-d) of Production Method 2.

Step (G-e)

A compound represented by the general formula (5-1) can be produced, using the compound represented by the general formula (G-2), in place of the compound represented by the general formula (2-5), in accordance with the method of step (2-a) of Production Method 2.

Reference Production Method H

A method for producing the compound represented by the general formula (7-2).

The compound represented by the general formula (7-2) can be produced through step (H-a) and step (H-b), as the following scheme.

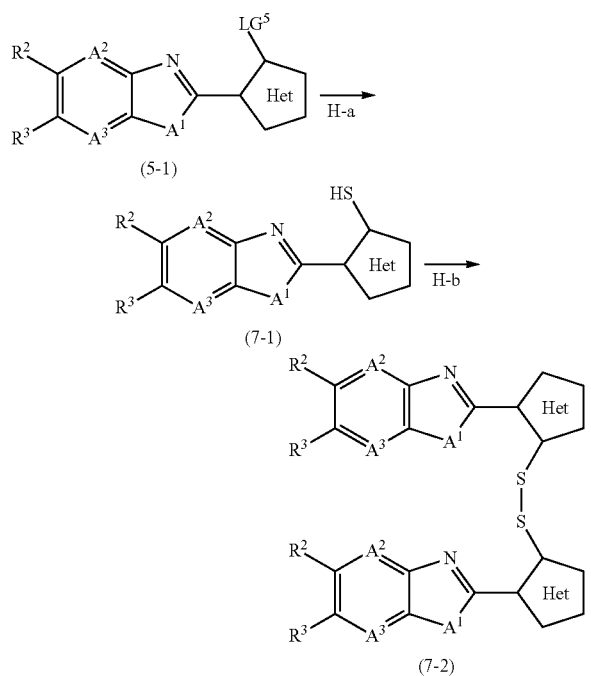

wherein $R^2$, $R^3$, $A^1$, $A^2$, $A^3$, $LG^5$ and Het represent the same meaning as described above.

Step (H-a)

The compound represented by the general formula (7-1) can be produced, using sodium sulfide, sodium hydrogen sulfide, hydrogen sulfide or the like, in place of the compound represented by the general formula (5-2), in accordance with the method of step (5-a) of Production Method 5.

Here, the reaction from the compound represented by the general formula (7-1) to the compound represented by the general formula (7-2) is likely to occur, and the compound represented by the general formula (7-2) is sometimes produced during synthesis of the compound represented by the general formula (7-1).

Step (H-b)

The compound represented by the general formula (7-2) can be produced by reacting the compound represented by the general formula (7-1) with an oxidizing agent.

The reaction is usually carried out in the presence of a solvent. Examples of the solvent include water, alcohols such as methanol and ethanol, ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, carboxylic acids such as acetic acid, and mixtures thereof.

Examples of the oxidizing agent include oxygen, iodine, aqueous hydrogen peroxide, and potassium ferricyanide.

In the reaction, the oxidizing agent is usually used in a ratio of 0.5 to 10 mol, based on 1 mol of the compound represented by the general formula (7-1).

The reaction temperature is usually within the range of 0 to 100° C. The reaction time is usually within the range of 0.1 to 24 hours.

After completion of the reaction, the compound represented by the general formula (7-2) can be isolated by extracting the reaction mixture with an organic solvent and subjecting the organic layer to post-treatment operations such as drying and concentration. The isolated compound represented by the general formula (7-2) can be also further purified by chromatography, recrystallization, or the like.

Reference Production Method I

A method for producing the compound represented by the general formula (2-5).

The compound represented by the general formula (2-5) can be produced by reacting the compound represented by the general formula (2-4) with a chlorinating agent.

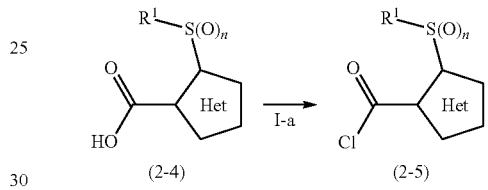

wherein $R^1$, n and Het represent the same meaning as described above.

Step (I-a)

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, aliphatic halogenated hydrocarbons such as dichloromethane and chloroform, and mixtures thereof.

Examples of the chlorinating agent include thionyl chloride, oxalyl dichloride and phosphorus oxychloride.

In the reaction, the chlorinating agent is usually used in a ratio of 1 to 5 mol, based on 1 mol of the compound represented by the general formula (2-4).

The reaction temperature is usually within the range of 0 to 100° C. The reaction time is usually within the range of 0.1 to 24 hours.

After completion of the reaction, the compound represented by the general formula (2-5) can be isolated by distilling the solvent.

Reference Production Method J

A method for producing the compound represented by the general formula (2-4).

The compound represented by the general formula (2-4) can be produced through step (J-a) and step (J-b), as the following scheme.

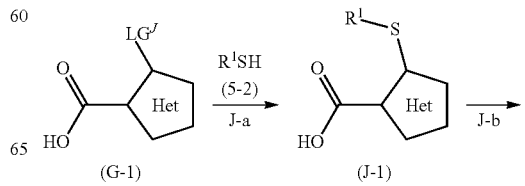

-continued (2-4)

wherein R¹, n and Het represent the same meaning as described above, and LG$^J$ represents a leaving group such as a chlorine atom, a bromine atom, an iodine atom, a methanesulfonyloxy group, a p-toluenesulfonyloxy group, or a trifluoromethanesulfonyloxy group.

Step (J-a)

A compound represented by the general formula (J-1) can be produced, using the compound represented by the general formula (G-1), in place of the compound represented by the general formula (5-1), in accordance with the method of step (5-a) of Production Method 5.

Step (J-b)

A compound represented by the general formula (2-4) wherein n is 1 can be produced, using the compound represented by the general formula (J-1), in place of the compound represented by the general formula (1-1), in accordance with the method of step (1-a) of Production Method 1. In addition, a compound represented by the general formula (2-4) wherein n is 2 can be produced, using the compound represented by the general formula (J-1), in place of the compound represented by the general formula (1-1), in accordance with the method of step (1-c) of Production Method 1.

Reference Production Method K

A method for producing the compound represented by the general formula (4-2).

The compound represented by the general formula (4-2) can be produced through step (K-a) and step (K-b), as the following scheme.

(K-1) → (K-2) → (4-2)

wherein R¹, n and Het represent the same meaning as described above, and LG$^K$ represents a leaving group such as a chlorine atom, a bromine atom, an iodine atom, a methanesulfonyloxy group, a p-toluenesulfonyloxy group, or a trifluoromethanesulfonyloxy group.

Step (K-a)

A compound represented by the general formula (K-2) can be produced, using a compound represented by the general formula (K-1), in place of the compound represented by the general formula (5-1), in accordance with the method of step (5-a) of Production Method 5.

Step (K-b)

A compound represented by the general formula (4-2) in which n is 1 can be produced, using the compound represented by the general formula (K-2), in place of the compound represented by the general formula (1-1), in accordance with the method of step (1-a) of Production Method 1.

In addition, a compound represented by the general formula (4-2) in which n is 2 can be produced, using the compound represented by the general formula (K-2), in place of the compound represented by the general formula (1-1), in accordance with the method of step (1-c) of Production Method 1.

Reference Production Method L

A method for producing the compound represented by the general formula (16-5).

The compound represented by the general formula (16-5) can be produced through step (L-a) and step (L-b), as the following scheme.

(L-1) → (16-4) → (16-5)

wherein $R^{1-7}$, $LG^7$, $G^1$, $G^2$, $G^3$ and n represent the same meaning as described above.

Step (L-a)

The compound represented by the general formula (16-4) can be produced, using a compound represented by the general formula (L-1), in place of the compound represented by the general formula (7-1), in accordance with the method of step (7-a) of Production Method 7.

Step (L-b)

A compound represented by the general formula (16-5) in which n is 1 can be produced, using a compound represented by the general formula (16-4), in place of the compound represented by the general formula (1-1), in accordance with the method of step (1-a) of Production Method 1. In addition, a compound represented by the general formula (16-5) in which n is 2 can be produced, using a compound represented by the general formula (16-4), in place of the compound represented by the general formula (1-1), in accordance with the method of step (1-c) of Production Method 1.

Reference Production Method M

A method for producing a compound represented by the general formula (M-6).

The compound represented by the general formula (M-6) can be produced through step (M-a) to step (M-d), as the following scheme.

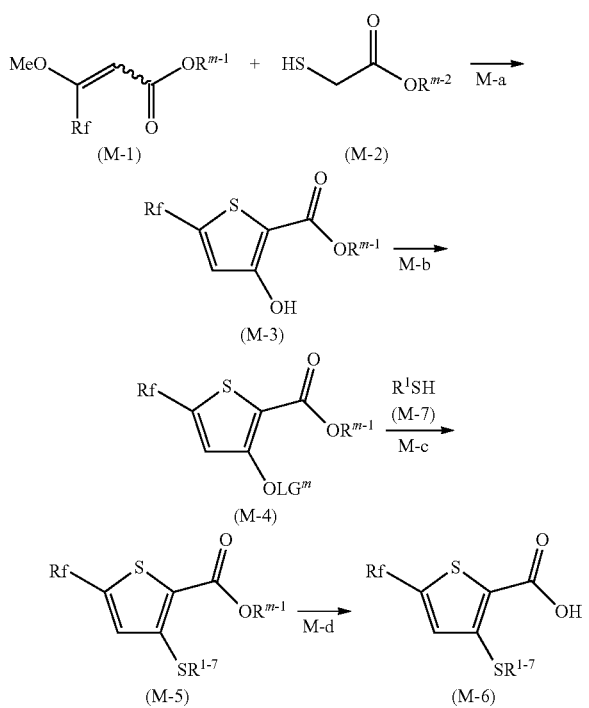

wherein $R^1$ and Rf represent the same meaning as described above, $R^{m-1}$ and $R^{m-2}$ are the same or different and represent a C1 to C7 alkyl group, and $LG^m$ represents a leaving group such as a methanesulfonyloxy group, a p-toluenesulfonyloxy group, or a trifluoromethanesulfonyloxy group.

Step (M-a)

A compound represented by the general formula (M-3) can be produced by reacting a compound represented by the general formula (M-1) with a compound represented by the general formula (M-2), in the presence of a base.

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, alcohols such as methanol and ethanol, and mixtures thereof. Examples of the base used in the reaction include alkali metal hydrides such as sodium hydride, alkali metal carbonates such as sodium carbonate and potassium carbonate, alkali metal hydroxides such as sodium hydroxide and potassium hydroxide, tertiary amines such as triethylamine and diisopropylethylamine, and nitrogen-containing aromatic compounds such as pyridine and 4-dimethylaminopyridine.

In the reaction, the compound represented by the general formula (M-2) is usually used in a ratio of 1 to 10 mol, and the base is usually used in a ratio of 1 to 10 mol, based on 1 mol of the compound represented by the general formula (M-1).

The reaction temperature is usually within the range of 0 to 150° C. The reaction time is usually within the range of 0.5 to 24 hours.

After completion of the reaction, the compound represented by the general formula (M-3) can be isolated by extracting the reaction mixture with an organic solvent and subjecting the organic layer to post-treatment operations such as drying and concentration. The isolated compound represented by the general formula (M-3) can be also further purified by chromatography, recrystallization, or the like.

Step (M-b)

A compound represented by the general formula (M-4) can be produced by reacting the compound represented by the general formula (M-3) with a sulfonylating agent in the presence of a base.

The reaction is usually carried out in the presence of a solvent. Examples of the solvent include ethers such as THF, ethylene glycol dimethyl ether, tert-butyl methyl ether and 1,4-dioxane, aromatic hydrocarbons such as toluene and xylene, nitriles such as acetonitrile, acid amides such as DMF and NMP, sulfoxides such as DMSO, and mixtures thereof.

Examples of the base include alkali metal hydrides such as sodium hydride, alkali metal carbonates such as sodium carbonate and potassium carbonate, alkali metal hydroxides such as sodium hydroxide and potassium hydroxide, tertiary amines such as triethylamine and diisopropylethylamine, and nitrogen-containing aromatic compounds such as pyridine and 4-dimethylaminopyridine. Examples of the sulfonylating agent include p-toluenesulfonyl chloride, methanesulfonyl chloride, trifluoromethanesulfonic anhydride, and N-phenyl-bis(trifluoromethanesulfonimide) (=N,N-bis(trifluoromethylsulfonyl)aniline).

In the reaction, the sulfonylating agent is usually used in a ratio of 1 to 10 mol, and the base is usually used in a ratio of 1 to 10 mol, based on 1 mol of the compound represented by the general formula (M-3).

The reaction temperature is usually within the range of 0 to 150° C. The reaction time is usually within the range of 0.5 to 24 hours.

After completion of the reaction, the compound represented by the general formula (M-4) can be isolated by extracting the reaction mixture with an organic solvent and subjecting the organic layer to post-treatment operations such as drying and concentration. The isolated compound represented by the general formula (M-4) can be also further purified by chromatography, recrystallization, or the like.

Step (M-c)

A compound represented by the general formula (M-5) can be produced, using the compound represented by the general formula (M-4), in place of the compound represented by the general formula (5-1), in accordance with the method of step (5-a) of Production Method 5.

Step (M-d)

The compound represented by the general formula (M-6) can be produced by hydrolyzing the compound represented by the general formula (M-5) by a base.

The reaction is usually carried out in the presence of a solvent. Examples of the solvent include ethers such as THF, ethylene glycol dimethyl ether, tert-butyl methyl ether and 1,4-dioxane, alcohols such as methanol and ethanol, water, and mixtures thereof.

Examples of the base used in hydrolysis include alkali metal hydroxides such as lithium hydroxide, sodium hydroxide and potassium hydroxide.

In the reaction, the base is usually used in a ratio of 1 to 10 mol, based on 1 mol of the compound represented by the general formula (M-5).

The reaction temperature is usually within the range of 0 to 120° C. The reaction time is usually within the range of 0.1 to 24 hours.

After completion of the reaction, the compound represented by the general formula (M-6) can be isolated by acidifying the reaction solution, then extracting the reaction mixture with an organic solvent, and subjecting the organic layer to post-treatment operations such as drying and concentration. The compound represented by the general formula (M-6) can be also further purified by chromatography, recrystallization, or the like.

Unless otherwise noted, the symbol of each substituent of the production intermediate represented by the general formula used in the production method and the reference production method represents the same meaning as the symbol of each substituent of the compound of the present invention represented by the general formula (1). Therefore, in the present specification, the production intermediate represented by the general formula corresponding to the compound of the present invention represented by the general formula (1) is disclosed.

Next, specific examples of the compound of the present invention are shown below.

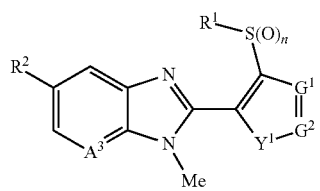

(X-1)

In the formula (X-1), compounds of the present invention wherein $Y^1$ is a sulfur atom, $G^1$ is CH, $G^2$ is CH, and $R^1$, $R^2$, $A^3$ and n are the combinations shown in [Table 1] to [Table 17].

TABLE 1

| $R^1$ | $R^2$ | $A^3$ | n |
|---|---|---|---|
| Et | $CF_3$ | N | 0 |
| CyPr | $CF_3$ | N | 0 |
| $CF_3$ | $CF_3$ | N | 0 |
| $CH_2CyPr$ | $CF_3$ | N | 0 |
| Et | $OCF_3$ | N | 0 |
| CyPr | $OCF_3$ | N | 0 |
| $CF_3$ | $OCF_3$ | N | 0 |
| $CH_2CyPr$ | $OCF_3$ | N | 0 |
| Et | $SCF_3$ | N | 0 |
| CyPr | $SCF_3$ | N | 0 |
| $CF_3$ | $SCF_3$ | N | 0 |
| $CH_2CyPr$ | $SCF_3$ | N | 0 |
| Et | $CF_2CF_3$ | N | 0 |
| CyPr | $CF_2CF_3$ | N | 0 |
| $CF_3$ | $CF_2CF_3$ | N | 0 |
| $CH_2CyPr$ | $CF_2CF_3$ | N | 0 |
| Et | $SOCF_3$ | N | 0 |
| CyPr | $SOCF_3$ | N | 0 |
| $CF_3$ | $SOCF_3$ | N | 0 |
| $CH_2CyPr$ | $SOCF_3$ | N | 0 |
| Et | $SO_2CF_3$ | N | 0 |
| CyPr | $SO_2CF_3$ | N | 0 |
| $CH_2CyPr$ | $SO_2CF_3$ | N | 0 |
| $CF_3$ | $SO_2CF_3$ | N | 0 |

TABLE 2

| $R^1$ | $R^2$ | $A^3$ | n |
|---|---|---|---|
| Et | $CF(CF_3)_2$ | N | 0 |
| CyPr | $CF(CF_3)_2$ | N | 0 |
| $CF_3$ | $CF(CF_3)_2$ | N | 0 |
| $CH_2CyPr$ | $CF(CF_3)_2$ | N | 0 |
| Et | $CF_3$ | CH | 0 |
| Pr | $CF_3$ | CH | 0 |
| CyPr | $CF_3$ | CH | 0 |
| $CF_3$ | $CF_3$ | CH | 0 |

TABLE 2-continued

| $R^1$ | $R^2$ | $A^3$ | n |
|---|---|---|---|
| $CH_2CyPr$ | $CF_3$ | CH | 0 |
| Et | $OCF_3$ | CH | 0 |
| CyPr | $OCF_3$ | CH | 0 |
| $CF_3$ | $OCF_3$ | CH | 0 |
| $CH_2CyPr$ | $OCF_3$ | CH | 0 |
| Et | $SCF_3$ | CH | 0 |
| CyPr | $SCF_3$ | CH | 0 |
| $CH_2CyPr$ | $SCF_3$ | CH | 0 |
| $CF_3$ | $SCF_3$ | CH | 0 |

TABLE 3

| $R^1$ | $R^2$ | $A^3$ | n |
|---|---|---|---|
| Et | $CF_2CF_3$ | CH | 0 |
| CyPr | $CF_2CF_3$ | CH | 0 |
| $CH_2CyPr$ | $CF_2CF_3$ | CH | 0 |
| $CF_3$ | $CF_2CF_3$ | CH | 0 |
| Et | $SOCF_3$ | CH | 0 |
| CyPr | $SOCF_3$ | CH | 0 |
| $CH_2CyPr$ | $SOCF_3$ | CH | 0 |
| $CF_3$ | $SOCF_3$ | CH | 0 |
| Et | $SO_2CF_3$ | CH | 0 |
| CyPr | $SO_2CF_3$ | CH | 0 |
| $CH_2CyPr$ | $SO_2CF_3$ | CH | 0 |
| $CF_3$ | $SO_2CF_3$ | CH | 0 |
| Et | $CF(CF_3)_2$ | CH | 0 |
| CyPr | $CF(CF_3)_2$ | CH | 0 |
| $CH_2CyPr$ | $CF(CF_3)_2$ | CH | 0 |
| $CF_3$ | $CF(CF_3)_2$ | CH | 0 |
| Et | $CF_3$ | CF | 0 |
| CyPr | $CF_3$ | CF | 0 |
| $CH_2CyPr$ | $CF_3$ | CF | 0 |
| $CF_3$ | $CF_3$ | CF | 0 |
| Et | $OCF_3$ | CF | 0 |
| CyPr | $OCF_3$ | CF | 0 |
| $CH_2CyPr$ | $OCF_3$ | CF | 0 |
| $CF_3$ | $OCF_3$ | CF | 0 |
| Et | $SCF_3$ | CF | 0 |
| CyPr | $SCF_3$ | CF | 0 |
| $CH_2CyPr$ | $SCF_3$ | CF | 0 |
| $CF_3$ | $SCF_3$ | CF | 0 |

TABLE 4

| $R^1$ | $R^2$ | $A^3$ | n |
|---|---|---|---|
| Et | $CF_2CF_3$ | CF | 0 |
| CyPr | $CF_2CF_3$ | CF | 0 |
| $CH_2CyPr$ | $CF_2CF_3$ | CF | 0 |
| $CF_3$ | $CF_2CF_3$ | CF | 0 |
| Et | $SOCF_3$ | CF | 0 |
| CyPr | $SOCF_3$ | CF | 0 |
| $CH_2CyPr$ | $SOCF_3$ | CF | 0 |
| $CF_3$ | $SOCF_3$ | CF | 0 |
| Et | $SO_2CF_3$ | CF | 0 |
| CyPr | $SO_2CF_3$ | CF | 0 |
| $CH_2CyPr$ | $SO_2CF_3$ | CF | 0 |
| $CF_3$ | $SO_2CF_3$ | CF | 0 |
| Et | $CF(CF_3)_2$ | CF | 0 |
| CyPr | $CF(CF_3)_2$ | CF | 0 |
| $CH_2CyPr$ | $CF(CF_3)_2$ | CF | 0 |
| $CF_3$ | $CF(CF_3)_2$ | CF | 0 |

TABLE 5

| $R^1$ | $R^2$ | $A^3$ | n |
|---|---|---|---|
| Et | $CF_3$ | CBr | 0 |
| CyPr | $CF_3$ | CBr | 0 |
| $CH_2CyPr$ | $CF_3$ | CBr | 0 |

TABLE 5-continued

| R¹ | R² | A³ | n |
|---|---|---|---|
| CF₃ | CF₃ | CBr | 0 |
| CH=CH₂ | CF₃ | CBr | 0 |
| Et | OCF₃ | CBr | 0 |
| CyPr | OCF₃ | CBr | 0 |
| CH₂CyPr | OCF₃ | CBr | 0 |
| CF₃ | OCF₃ | CBr | 0 |
| Et | SCF₃ | CBr | 0 |
| CyPr | SCF₃ | CBr | 0 |
| CH₂CyPr | SCF₃ | CBr | 0 |
| CF₃ | SCF₃ | CBr | 0 |
| Et | CF₂CF₃ | CBr | 0 |
| CyPr | CF₂CF₃ | CBr | 0 |
| CH₂CyPr | CF₂CF₃ | CBr | 0 |
| CF₃ | CF₂CF₃ | CBr | 0 |
| Et | SOCF₃ | CBr | 0 |
| CyPr | SOCF₃ | CBr | 0 |
| CH₂CyPr | SOCF₃ | CBr | 0 |
| CF₃ | SOCF₃ | CBr | 0 |
| Et | SO₂CF₃ | CBr | 0 |
| CyPr | SO₂CF₃ | CBr | 0 |
| CH₂CyPr | SO₂CF₃ | CBr | 0 |
| CF₃ | SO₂CF₃ | CBr | 0 |
| Et | CF(CF₃)₂ | CBr | 0 |
| CyPr | CF(CF₃)₂ | CBr | 0 |
| CH₂CyPr | CF(CF₃)₂ | CBr | 0 |
| CF₃ | CF(CF₃)₂ | CBr | 0 |

TABLE 6

| R¹ | R² | A³ | n |
|---|---|---|---|
| Et | CF₃ | N | 1 |
| CyPr | CF₃ | N | 1 |
| CH₂CyPr | CF₃ | N | 1 |
| CF₃ | CF₃ | N | 1 |
| Et | OCF₃ | N | 1 |
| CyPr | OCF₃ | N | 1 |
| CH₂CyPr | OCF₃ | N | 1 |
| CF₃ | OCF₃ | N | 1 |
| Et | SCF₃ | N | 1 |
| CyPr | SCF₃ | N | 1 |
| CH₂CyPr | SCF₃ | N | 1 |
| CF₃ | SCF₃ | N | 1 |
| Et | CF₂CF₃ | N | 1 |
| CyPr | CF₂CF₃ | N | 1 |
| CH₂CyPr | CF₂CF₃ | N | 1 |
| CF₃ | CF₂CF₃ | N | 1 |
| Et | SOCF₃ | N | 1 |
| CyPr | SOCF₃ | N | 1 |
| CH₂CyPr | SOCF₃ | N | 1 |
| CF₃ | SOCF₃ | N | 1 |
| Et | SO₂CF₃ | N | 1 |
| CyPr | SO₂CF₃ | N | 1 |
| CH₂CyPr | SO₂CF₃ | N | 1 |
| CF₃ | SO₂CF₃ | N | 1 |

TABLE 7

| R¹ | R² | A³ | n |
|---|---|---|---|
| Et | CF(CF₃)₂ | N | 1 |
| CyPr | CF(CF₃)₂ | N | 1 |
| CH₂CyPr | CF(CF₃)₂ | N | 1 |
| CF₃ | CF(CF₃)₂ | N | 1 |
| Et | CF₃ | CH | 1 |
| Pr | CF₃ | CH | 1 |
| CyPr | CF₃ | CH | 1 |
| CH₂CyPr | CF₃ | CH | 1 |
| CF₃ | CF₃ | CH | 1 |
| Et | OCF₃ | CH | 1 |
| CyPr | OCF₃ | CH | 1 |
| CH₂CyPr | OCF₃ | CH | 1 |
| CF₃ | OCF₃ | CH | 1 |

TABLE 7-continued

| R¹ | R² | A³ | n |
|---|---|---|---|
| Et | SCF₃ | CH | 1 |
| CyPr | SCF₃ | CH | 1 |
| CH₂CyPr | SCF₃ | CH | 1 |
| CF₃ | SCF₃ | CH | 1 |

TABLE 8

| R¹ | R² | A³ | n |
|---|---|---|---|
| Et | CF₂CF₃ | CH | 1 |
| CyPr | CF₂CF₃ | CH | 1 |
| CH₂CyPr | CF₂CF₃ | CH | 1 |
| CF₃ | CF₂CF₃ | CH | 1 |
| Et | SOCF₃ | CH | 1 |
| CyPr | SOCF₃ | CH | 1 |
| CH₂CyPr | SOCF₃ | CH | 1 |
| CF₃ | SOCF₃ | CH | 1 |
| Et | SO₂CF₃ | CH | 1 |
| CyPr | SO₂CF₃ | CH | 1 |
| CH₂CyPr | SO₂CF₃ | CH | 1 |
| CF₃ | SO₂CF₃ | CH | 1 |
| Et | CF(CF₃)₂ | CH | 1 |
| CyPr | CF(CF₃)₂ | CH | 1 |
| CH₂CyPr | CF(CF₃)₂ | CH | 1 |
| CF₃ | CF(CF₃)₂ | CH | 1 |
| Et | CF₃ | CF | 1 |
| CyPr | CF₃ | CF | 1 |
| CH₂CyPr | CF₃ | CF | 1 |
| CF₃ | CF₃ | CF | 1 |
| Et | OCF₃ | CF | 1 |
| CyPr | OCF₃ | CF | 1 |
| CH₂CyPr | OCF₃ | CF | 1 |
| CF₃ | OCF₃ | CF | 1 |
| Et | SCF₃ | CF | 1 |
| CyPr | SCF₃ | CF | 1 |
| CH₂CyPr | SCF₃ | CF | 1 |
| CF₃ | SCF₃ | CF | 1 |

TABLE 9

| R¹ | R² | A³ | n |
|---|---|---|---|
| Et | CF₂CF₃ | CF | 1 |
| CyPr | CF₂CF₃ | CF | 1 |
| CH₂CyPr | CF₂CF₃ | CF | 1 |
| CF₃ | CF₂CF₃ | CF | 1 |
| Et | SOCF₃ | CF | 1 |
| CyPr | SOCF₃ | CF | 1 |
| CH₂CyPr | SOCF₃ | CF | 1 |
| CF₃ | SOCF₃ | CF | 1 |
| Et | SO₂CF₃ | CF | 1 |
| CyPr | SO₂CF₃ | CF | 1 |
| CH₂CyPr | SO₂CF₃ | CF | 1 |
| CF₃ | SO₂CF₃ | CF | 1 |
| Et | CF(CF₃)₂ | CF | 1 |
| CyPr | CF(CF₃)₂ | CF | 1 |
| CH₂CyPr | CF(CF₃)₂ | CF | 1 |
| CF₃ | CF(CF₃)₂ | CF | 1 |

TABLE 10

| R¹ | R² | A³ | n |
|---|---|---|---|
| Et | CF₃ | CBr | 1 |
| CyPr | CF₃ | CBr | 1 |
| CH₂CyPr | CF₃ | CBr | 1 |
| CF₃ | CF₃ | CBr | 1 |
| CH=CH₂ | CF₃ | CBr | 1 |
| Et | OCF₃ | CBr | 1 |
| CyPr | OCF₃ | CBr | 1 |
| CH₂CyPr | OCF₃ | CBr | 1 |

TABLE 10-continued

| R¹ | R² | A³ | n |
|---|---|---|---|
| CF₃ | OCF₃ | CBr | 1 |
| Et | SCF₃ | CBr | 1 |
| CyPr | SCF₃ | CBr | 1 |
| CH₂CyPr | SCF₃ | CBr | 1 |
| CF₃ | SCF₃ | CBr | 1 |
| Et | CF₂CF₃ | CBr | 1 |
| CyPr | CF₂CF₃ | CBr | 1 |
| CH₂CyPr | CF₂CF₃ | CBr | 1 |
| CF₃ | CF₂CF₃ | CBr | 1 |
| Et | SOCF₃ | CBr | 1 |
| CyPr | SOCF₃ | CBr | 1 |
| CH₂CyPr | SOCF₃ | CBr | 1 |
| CF₃ | SOCF₃ | CBr | 1 |
| Et | SO₂CF₃ | CBr | 1 |
| CyPr | SO₂CF₃ | CBr | 1 |
| CH₂CyPr | SO₂CF₃ | CBr | 1 |
| CF₃ | SO₂CF₃ | CBr | 1 |
| Et | CF(CF₃)₂ | CBr | 1 |
| CyPr | CF(CF₃)₂ | CBr | 1 |
| CH₂CyPr | CF(CF₃)₂ | CBr | 1 |
| CF₃ | CF(CF₃)₂ | CBr | 1 |

TABLE 11

| R¹ | R² | A³ | n |
|---|---|---|---|
| Me | CF₃ | N | 2 |
| Et | CF₃ | N | 2 |
| Pr | CF₃ | N | 2 |
| CyPr | CF₃ | N | 2 |
| CH₂CyPr | CF₃ | N | 2 |
| CF₃ | CF₃ | N | 2 |
| CH=CH₂ | CF₃ | N | 2 |
| CH₂CF₃ | CF₃ | N | 2 |
| C≡CH | CF₃ | N | 2 |
| Me | OCF₃ | N | 2 |
| Et | OCF₃ | N | 2 |
| Pr | OCF₃ | N | 2 |
| CyPr | OCF₃ | N | 2 |
| CH₂CyPr | OCF₃ | N | 2 |
| CF₃ | OCF₃ | N | 2 |
| CH=CH₂ | OCF₃ | N | 2 |
| CH₂CF₃ | OCF₃ | N | 2 |
| C≡CH | OCF₃ | N | 2 |
| Me | SCF₃ | N | 2 |
| Et | SCF₃ | N | 2 |
| Pr | SCF₃ | N | 2 |
| CyPr | SCF₃ | N | 2 |
| CH₂CyPr | SCF₃ | N | 2 |
| CF₃ | SCF₃ | N | 2 |
| CH=CH₂ | SCF₃ | N | 2 |
| CH₂CF₃ | SCF₃ | N | 2 |
| C≡CH | SCF₃ | N | 2 |

TABLE 12

| R¹ | R² | A³ | n |
|---|---|---|---|
| Me | CF₂CF₃ | N | 2 |
| Et | CF₂CF₃ | N | 2 |
| Pr | CF₂CF₃ | N | 2 |
| CyPr | CF₂CF₃ | N | 2 |
| CH₂CyPr | CF₂CF₃ | N | 2 |
| CF₃ | CF₂CF₃ | N | 2 |
| CH=CH₂ | CF₂CF₃ | N | 2 |
| CH₂CF₃ | CF₂CF₃ | N | 2 |
| C≡CH | CF₂CF₃ | N | 2 |
| Me | SOCF₃ | N | 2 |
| Et | SOCF₃ | N | 2 |
| Pr | SOCF₃ | N | 2 |
| CyPr | SOCF₃ | N | 2 |
| CH₂CyPr | SOCF₃ | N | 2 |
| CF₃ | SOCF₃ | N | 2 |

TABLE 12-continued

| R¹ | R² | A³ | n |
|---|---|---|---|
| CH=CH₂ | SOCF₃ | N | 2 |
| CH₂CF₃ | SOCF₃ | N | 2 |
| C≡CH | SOCF₃ | N | 2 |
| Me | SO₂CF₃ | N | 2 |
| Et | SO₂CF₃ | N | 2 |
| Pr | SO₂CF₃ | N | 2 |
| CyPr | SO₂CF₃ | N | 2 |
| CH₂CyPr | SO₂CF₃ | N | 2 |
| CF₃ | SO₂CF₃ | N | 2 |
| CH=CH₂ | SO₂CF₃ | N | 2 |
| CH₂CF₃ | SO₂CF₃ | N | 2 |
| C≡CH | SO₂CF₃ | N | 2 |

TABLE 13

| R¹ | R² | A³ | n |
|---|---|---|---|
| Me | CF(CF₃)₂ | N | 2 |
| Et | CF(CF₃)₂ | N | 2 |
| Pr | CF(CF₃)₂ | N | 2 |
| CyPr | CF(CF₃)₂ | N | 2 |
| CH₂CyPr | CF(CF₃)₂ | N | 2 |
| CF₃ | CF(CF₃)₂ | N | 2 |
| CH=CH₂ | CF(CF₃)₂ | N | 2 |
| CH₂CF₃ | CF(CF₃)₂ | N | 2 |
| C≡CH | CF(CF₃)₂ | N | 2 |
| Me | CF₃ | CH | 2 |
| Et | CF₃ | CH | 2 |
| Pr | CF₃ | CH | 2 |
| CyPr | CF₃ | CH | 2 |
| CH₂CyPr | CF₃ | CH | 2 |
| CF₃ | CF₃ | CH | 2 |
| CH=CH₂ | CF₃ | CH | 2 |
| CH₂CF₃ | CF₃ | CH | 2 |
| C≡CH | CF₃ | CH | 2 |
| Me | OCF₃ | CH | 2 |
| Et | OCF₃ | CH | 2 |
| Pr | OCF₃ | CH | 2 |
| CyPr | OCF₃ | CH | 2 |
| CH₂CyPr | OCF₃ | CH | 2 |
| CF₃ | OCF₃ | CH | 2 |
| CH=CH₂ | OCF₃ | CH | 2 |
| CH₂CF₃ | OCF₃ | CH | 2 |
| C≡CH | OCF₃ | CH | 2 |
| Me | SCF₃ | CH | 2 |
| Et | SCF₃ | CH | 2 |
| Pr | SCF₃ | CH | 2 |
| CyPr | SCF₃ | CH | 2 |
| CH₂CyPr | SCF₃ | CH | 2 |
| CF₃ | SCF₃ | CH | 2 |
| CH=CH₂ | SCF₃ | CH | 2 |
| CH₂CF₃ | SCF₃ | CH | 2 |
| C≡CH | SCF₃ | CH | 2 |

TABLE 14

| R¹ | R² | A³ | n |
|---|---|---|---|
| Me | CF₂CF₃ | CH | 2 |
| Et | CF₂CF₃ | CH | 2 |
| Pr | CF₂CF₃ | CH | 2 |
| CyPr | CF₂CF₃ | CH | 2 |
| CH₂CyPr | CF₂CF₃ | CH | 2 |
| CF₃ | CF₂CF₃ | CH | 2 |
| CH=CH₂ | CF₂CF₃ | CH | 2 |
| CH₂CF₃ | CF₂CF₃ | CH | 2 |
| C≡CH | CF₂CF₃ | CH | 2 |
| Me | SOCF₃ | CH | 2 |
| Et | SOCF₃ | CH | 2 |
| Pr | SOCF₃ | CH | 2 |
| CyPr | SOCF₃ | CH | 2 |
| CH₂CyPr | SOCF₃ | CH | 2 |
| CF₃ | SOCF₃ | CH | 2 |

TABLE 14-continued

| R¹ | R² | A³ | n |
|---|---|---|---|
| CH=CH₂ | SOCF₃ | CH | 2 |
| CH₂CF₃ | SOCF₃ | CH | 2 |
| C≡CH | SOCF₃ | CH | 2 |
| Me | SO₂CF₃ | CH | 2 |
| Et | SO₂CF₃ | CH | 2 |
| Pr | SO₂CF₃ | CH | 2 |
| CyPr | SO₂CF₃ | CH | 2 |
| CH₂CyPr | SO₂CF₃ | CH | 2 |
| CF₃ | SO₂CF₃ | CH | 2 |
| CH=CH₂ | SO₂CF₃ | CH | 2 |
| CH₂CF₃ | SO₂CF₃ | CH | 2 |
| C≡CH | SO₂CF₃ | CH | 2 |

TABLE 15

| R¹ | R² | A³ | n |
|---|---|---|---|
| Me | CF(CF₃)₂ | CH | 2 |
| Et | CF(CF₃)₂ | CH | 2 |
| Pr | CF(CF₃)₂ | CH | 2 |
| CyPr | CF(CF₃)₂ | CH | 2 |
| CH₂CyPr | CF(CF₃)₂ | CH | 2 |
| CF₃ | CF(CF₃)₂ | CH | 2 |
| CH=CH₂ | CF(CF₃)₂ | CH | 2 |
| CH₂CF₃ | CF(CF₃)₂ | CH | 2 |
| C≡CH | CF(CF₃)₂ | CH | 2 |
| Et | CF₃ | CF | 2 |
| CyPr | CF₃ | CF | 2 |
| CH₂CyPr | CF₃ | CF | 2 |
| CF₃ | CF₃ | CF | 2 |
| CH=CH₂ | CF₃ | CF | 2 |
| Et | OCF₃ | CF | 2 |
| CyPr | OCF₃ | CF | 2 |
| CH₂CyPr | OCF₃ | CF | 2 |
| CF₃ | OCF₃ | CF | 2 |
| Et | SCF₃ | CF | 2 |
| CyPr | SCF₃ | CF | 2 |
| CH₂CyPr | SCF₃ | CF | 2 |
| CF₃ | SCF₃ | CF | 2 |

TABLE 16

| R¹ | R² | A³ | n |
|---|---|---|---|
| Et | CF₂CF₃ | CF | 2 |
| CyPr | CF₂CF₃ | CF | 2 |
| CH₂CyPr | CF₂CF₃ | CF | 2 |
| CF₃ | CF₂CF₃ | CF | 2 |
| Et | SOCF₃ | CF | 2 |
| CyPr | SOCF₃ | CF | 2 |
| CH₂CyPr | SOCF₃ | CF | 2 |
| CF₃ | SOCF₃ | CF | 2 |
| Et | SO₂CF₃ | CF | 2 |
| CyPr | SO₂CF₃ | CF | 2 |
| CH₂CyPr | SO₂CF₃ | CF | 2 |
| CF₃ | SO₂CF₃ | CF | 2 |
| Et | CF(CF₃)₂ | CF | 2 |
| CyPr | CF(CF₃)₂ | CF | 2 |
| CH₂CyPr | CF(CF₃)₂ | CF | 2 |
| CF₃ | CF(CF₃)₂ | CF | 2 |

TABLE 17

| R¹ | R² | A³ | n |
|---|---|---|---|
| Et | CF₃ | CBr | 2 |
| CyPr | CF₃ | CBr | 2 |
| CH₂CyPr | CF₃ | CBr | 2 |
| CF₃ | CF₃ | CBr | 2 |
| CH=CH₂ | CF₃ | CBr | 2 |
| Et | OCF₃ | CBr | 2 |
| CyPr | OCF₃ | CBr | 2 |
| CH₂CyPr | OCF₃ | CBr | 2 |
| CF₃ | OCF₃ | CBr | 2 |
| Et | SCF₃ | CBr | 2 |
| CyPr | SCF₃ | CBr | 2 |
| CH₂CyPr | SCF₃ | CBr | 2 |
| CF₃ | SCF₃ | CBr | 2 |
| Et | CF₂CF₃ | CBr | 2 |
| CyPr | CF₂CF₃ | CBr | 2 |
| CH₂CyPr | CF₂CF₃ | CBr | 2 |
| CF₃ | CF₂CF₃ | CBr | 2 |
| Et | SOCF₃ | CBr | 2 |
| CyPr | SOCF₃ | CBr | 2 |
| CH₂CyPr | SOCF₃ | CBr | 2 |
| CF₃ | SOCF₃ | CBr | 2 |
| Et | SO₂CF₃ | CBr | 2 |
| CyPr | SO₂CF₃ | CBr | 2 |
| CH₂CyPr | SO₂CF₃ | CBr | 2 |
| CF₃ | SO₂CF₃ | CBr | 2 |
| Et | CF(CF₃)₂ | CBr | 2 |
| CyPr | CF(CF₃)₂ | CBr | 2 |
| CH₂CyPr | CF(CF₃)₂ | CBr | 2 |
| CF₃ | CF(CF₃)₂ | CBr | 2 |

(In [Table 1] to [Table 17] above, Me represents a methyl group, Et represents an ethyl group, Pr represents an n-propyl group, and CyPr represents a cyclopropyl group.)

In the formula (X-1), compounds of the present invention wherein $Y^1$ is a sulfur atom, $G^1$ is CH, $G^2$ is $CR^6$, $R^6$ is $CF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is $OCF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is $CF_2CF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is $CH_2CF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is $SCF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is $SOCF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is $SO_2CF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is a 2-pyridyl group, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is $CR^6$, $R^6$ is a pyrimidin-2-yl group, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is CH, and $R^1$, $R^2$, $A^3$ and n are the combinations shown in [Table 1] to [Table 17].

In the formula (X-1), compounds of the present invention wherein $Y^1$ is a sulfur atom, G is a nitrogen atom, $G^2$ is $CR^6$, $R^6$ is $CF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is $CH_2CF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is $SOCF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is $SO_2CF_3$, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-1), compounds of the present invention wherein $Y^1$ is a sulfur atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

In the formula (X-1), compounds of the present invention wherein $Y^1$ is a sulfur atom, $G^1$ is CH, $G^2$ is a nitrogen atom, and $R^1$, $R^2$, $A^3$ and n are the combinations shown in [Table 1] to [Table 17].

In the formula (X-1), compounds of the present invention wherein $Y^1$ is a sulfur atom, $G^1$ is $CR^6$, $R^6$ is $OCF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is a sulfur atom, $G^1$ is $CR^6$, $R^6$ is $CF_2CF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is a sulfur atom, $G^1$ is $CR^6$, $R^6$ is $CF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is a sulfur atom, $G^1$ is $CR^6$, $R^6$ is $SCF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ and $G^2$ are CH, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is $CR^6$, $R^6$ is $CF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is $CR^6$, $R^6$ is $OCF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is $CR^6$, $R^6$ is $SCF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is $CR^6$, $R^6$ is $CF_2CF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is $CR^6$, $R^6$ is a 2-pyridyl group, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is $CR^6$, $R^6$ is a pyrimidin-2-yl group, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is $CR^6$, $R^6$ is $OCF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is $CR^6$, $R^6$ is $CF_2CF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is $CR^6$, $R^6$ is $CF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is $CR^6$, $R^6$ is $SCF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is CH, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is $CH_2CF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is $SOCF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is $SO_2CF_3$, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-1), compounds of the present invention wherein $Y^1$ is an oxygen atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

In the formula (X-1), compounds of the present invention wherein $Y^1$ is an oxygen atom, $G^1$ is CH, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is $CR^6$, $R^6$ is $OCF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is $CR^6$, $R^6$ is $CF_2CF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is $CR^6$, $R^6$ is $CF_3$, $G^2$ is a nitrogen atom, and $R^1$, $R^2$, $A^3$ and n are the combinations shown in [Table 1] to [Table 17].

In the formula (X-1), compounds of the present invention wherein $Y^1$ is an oxygen atom, $G^1$ is $CR^6$, $R^6$ is $SCF_3$, $G^2$ is a nitrogen atom, and $R^1$, $R^2$, $A^3$ and n are the combinations shown in [Table 1] to [Table 17].

(X-2)

In the formula (X-2), compounds of the present invention wherein $Y^1$ is a sulfur atom, $G^1$ is CH, $G^2$ is CH, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is $CR^6$, $R^6$ is $CF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is $CR^6$, $R^6$ is $OCF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is $CR^6$, $R^6$ is $CF_2CF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is $CR^6$, $R^6$ is $SCF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is $CR^6$, $R^6$ is $SO_2CF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is $CR^6$, $R^6$ is a 2-pyridyl group, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is $CR^6$, $R^6$ is a pyrimidin-2-yl group, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is CH, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is $CR^6$, $R^6$ is $SOCF_3$, and $R^1$, $R^2$, $A^3$ and n are the combinations shown in [Table 1] to [Table 17].

In the formula (X-2), compounds of the present invention wherein Y is a sulfur atom, $G^1$ is a nitrogen atom, $G^2$ is $CR^6$, $R^6$ is $SO_2CF_3$, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-2), compounds of the present invention wherein $Y^1$ is a sulfur atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

In the formula (X-2), compounds of the present invention wherein $Y^1$ is a sulfur atom, $G^1$ is CH, $G^2$ is a nitrogen atom, and $R^1$, $R^2$, $A^3$ and n are the combinations shown in [Table 1] to [Table 17].

In the formula (X-2), compounds of the present invention wherein $Y^1$ is a sulfur atom, G is $CR^6$, $R^6$ is $CF_2CF_3$, $G^2$ is a nitrogen atom, and $R^1$, $R^2$, $A^3$ and n are the combinations shown in [Table 1] to [Table 17].

In the formula (X-2), compounds of the present invention wherein $Y^1$ is a sulfur atom, $G^1$ is $CR^6$, $R^6$ is $CF_3$, $G^2$ is a nitrogen atom, and $R^1$, $R^2$, $A^3$ and n are the combinations shown in [Table 1] to [Table 17].

In the formula (X-2), compounds of the present invention wherein $Y^1$ is an oxygen atom, $G^1$ and $G^2$ are CH, and $R^1$, $R^2$, $A^3$ and n are the combinations shown in [Table 1] to [Table 17].

In the formula (X-2), compounds of the present invention wherein $Y^1$ is an oxygen atom, $G^1$ is CH, $G^2$ is $CR^6$, $R^6$ is $CF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is CH, $G^2$ is $CR^6$, $R^6$ is $OCF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is CH, $G^2$ is $CR^6$, $R^6$ is $SCF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is CH, $G^2$ is $CR^6$, $R^6$ is $CF_2CF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is CH, $G^2$ is $CR^6$, $R^6$ is a 2-pyridyl group, and $R^1$, $R^2$, $A^3$ and n are the combinations shown in [Table 1] to [Table 17].

In the formula (X-2), compounds of the present invention wherein $Y^1$ is an oxygen atom, $G^1$ is CH, $G^2$ is $CR^6$, $R^6$ is a 5-$CF_3$ pyridyl group, and $R^1$, $R^2$, $A^3$ and n are the combinations shown in [Table 1] to [Table 17].

In the formula (X-2), compounds of the present invention wherein $Y^1$ is an oxygen atom, $G^1$ is CH, $G^2$ is $CR^6$, $R^6$ is a pyrimidin-2-yl group, and $R^1$, $R^2$, $A^3$ and n are the combinations shown in [Table 1] to [Table 17].

In the formula (X-2), compounds of the present invention wherein $Y^1$ is an oxygen atom, $G^1$ is CH, $G^2$ is a nitrogen atom, and $R^1$, $R^2$, $A^3$ and n are the combinations shown in [Table 1] to [Table 17].

In the formula (X-2), compounds of the present invention wherein $Y^1$ is an oxygen atom, $G^1$ is $CR^6$, $R^6$ is $CF_2CF_3$, $G^2$ is a nitrogen atom, and $R^1$, $R^2$, $A^3$ and n are the combinations shown in [Table 1] to [Table 17].

In the formula (X-2), compounds of the present invention wherein $Y^1$ is an oxygen atom, $G^1$ is $CR^6$, $R^6$ is $CF_3$, $G^2$ is a nitrogen atom, and $R^1$, $R^2$, $A^3$ and n are the combinations shown in [Table 1] to [Table 17].

In the formula (X-2), compounds of the present invention wherein $Y^1$ is an oxygen atom, G is $CR^6$, $R^6$ is $SCF_3$, $G^2$ is a nitrogen atom, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is CH, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is $CR^6$, $R^6$ is $CH_2CF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-2), compounds of the present invention wherein $Y^1$ is an oxygen atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

(X-3)

In the formula (X-3), compounds of the present invention wherein $Y^1$ is a sulfur atom, $G^1$ is CH, $G^2$ is CH, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is $CR^6$, $R^6$ is $CF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is $CR^6$, $R^6$ is $OCF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is $CR^6$, $R^6$ is $CF_2CF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is $CR^6$, $R^6$ is $SCF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is $CR^6$, $R^6$ is $SO_2CF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is $CR^6$, $R^6$ is a 2-pyridyl group, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is $CR^6$, $R^6$ is a pyrimidin-2-yl group, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is CH, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is $SOCF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is $SO_2CF_3$, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-3), compounds of the present invention wherein $Y^1$ is a sulfur atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

In the formula (X-3), compounds of the present invention wherein $Y^1$ is a sulfur atom, $G^1$ is CH, $G^2$ is a nitrogen atom, and $R^1$, $R^2$, $A^3$ and n are the combinations shown in [Table 1] to [Table 17].

In the formula (X-3), compounds of the present invention wherein $Y^1$ is a sulfur atom, $G^1$ is $CR^6$, $R^6$ is $CF_2CF_3$, $G^2$ is a nitrogen atom, and $R^1$, $R^2$, $A^3$ and n are the combinations shown in [Table 1] to [Table 17].

In the formula (X-3), compounds of the present invention wherein $Y^1$ is a sulfur atom, $G^1$ is $CR^6$, $R^6$ is $CF_3$, $G^2$ is a nitrogen atom, and $R^1$, $R^2$, $A^3$ and n are the combinations shown in [Table 1] to [Table 17].

In the formula (X-3), compounds of the present invention wherein $Y^1$ is an oxygen atom, G and $G^2$ are CH, and $R^1$, $R^2$, $A^3$ and n are the combinations shown in [Table 1] to [Table 17].

In the formula (X-3), compounds of the present invention wherein $Y^1$ is an oxygen atom, $G^1$ is CH, $G^2$ is $CR^6$, $R^6$ is $CF_3$, and $R^1$, $R^2$, $A^3$ and n are the combinations shown in [Table 1] to [Table 17].

In the formula (X-3), compounds of the present invention wherein $Y^1$ is an oxygen atom, $G^1$ is CH, $G^2$ is $CR^6$, $R^6$ is $OCF_3$, and $R^1$, $R^2$, $A^3$ and n are the combinations shown in [Table 1] to [Table 17].

In the formula (X-3), compounds of the present invention wherein $Y^1$ is an oxygen atom, $G^1$ is CH, $G^2$ is $CR^6$, $R^6$ is $SCF_3$, and $R^1$, $R^2$, $A^3$ and n are the combinations shown in [Table 1] to [Table 17].

In the formula (X-3), compounds of the present invention wherein $Y^1$ is an oxygen atom, $G^1$ is CH, $G^2$ is $CR^6$, $R^6$ is $CF_2CF_3$, and $R^1$, $R^2$, $A^3$ and n are the combinations shown in [Table 1] to [Table 17].

In the formula (X-3), compounds of the present invention wherein $Y^1$ is an oxygen atom, $G^1$ is CH, $G^2$ is $CR^6$, $R^6$ is a 2-pyridyl group, and $R^1$, $R^2$, $A^3$ and n are the combinations shown in [Table 1] to [Table 17].

In the formula (X-3), compounds of the present invention wherein $Y^1$ is an oxygen atom, $G^1$ is CH, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-3), compounds of the present invention wherein $Y^1$ is an oxygen atom, $G^1$ is CH, $G^2$ is $CR^6$, $R^6$ is a pyrimidin-2-yl group, and $R^1$, $R^2$, $A^3$ and n are the combinations shown in [Table 1] to [Table 17].

In the formula (X-3), compounds of the present invention wherein $Y^1$ is an oxygen atom, $G^1$ is CH, $G^2$ is a nitrogen atom, and $R^1$, $R^2$, $A^3$ and n are the combinations shown in [Table 1] to [Table 17].

In the formula (X-3), compounds of the present invention wherein $Y^1$ is an oxygen atom, $G^1$ is $CR^6$, $R^6$ is $CF_2CF_3$, $G^2$ is a nitrogen atom, and $R^1$, $R^2$, $A^3$ and n are the combinations shown in [Table 1] to [Table 17].

In the formula (X-3), compounds of the present invention wherein $Y^1$ is an oxygen atom, $G^1$ is $CR^6$, $R^6$ is $CF_3$, $G^2$ is a nitrogen atom, and $R^1$, $R^2$, $A^3$ and n are the combinations shown in [Table 1] to [Table 17].

In the formula (X-3), compounds of the present invention wherein $Y^1$ is an oxygen atom, $G^1$ is $CR^6$, $R^6$ is $SCF_3$, $G^2$ is a nitrogen atom, and $R^1$, $R^2$, $A^3$ and n are the combinations shown in [Table 1] to [Table 17].

In the formula (X-3), compounds of the present invention wherein $Y^1$ is an oxygen atom, $G^1$ is a nitrogen atom, $G^2$ is CH, and $R^1$, $R^2$, $A^3$ and n are the combinations shown in [Table 1] to [Table 17].

In the formula (X-3), compounds of the present invention wherein $Y^1$ is an oxygen atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-3), compounds of the present invention wherein $Y^1$ is an oxygen atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-3), compounds of the present invention wherein $Y^1$ is an oxygen atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-3), compounds of the present invention wherein $Y^1$ is an oxygen atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-3), compounds of the present invention wherein $Y^1$ is an oxygen atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-3), compounds of the present invention wherein $Y^1$ is an oxygen atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-3), compounds of the present invention wherein $Y^1$ is an oxygen atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

(X-4)

In the formula (X-4), compounds of the present invention wherein $Y^2$ is a sulfur atom, $G^1$ is CH, $G^2$ is CH, and $R^1$, $R^2$, $A^3$ and n are the combinations shown in [Table 1] to [Table 17].

In the formula (X-4), compounds of the present invention wherein $Y^2$ is a sulfur atom, $G^1$ is CH, $G^2$ is $CR^6$, $R^6$ is $CF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is CH, $G^2$ is $CR^6$, $R^6$ is $OCF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is CH, $G^2$ is $CR^6$, $R^6$ is $CF_2CF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is CH, $G^2$ is $CR^6$, $R^6$ is $SCF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is CH, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is $SOCF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is $SO_2CF_3$, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-4), compounds of the present invention wherein $Y^2$ is a sulfur atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

In the formula (X-4), compounds of the present invention wherein $Y^2$ is an oxygen atom, $G^1$ is a nitrogen atom, $G^2$ is CH, and $R^1$, $R^2$, $A^3$ and n are the combinations shown in [Table 1] to [Table 17].

In the formula (X-4), compounds of the present invention wherein $Y^2$ is an oxygen atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-4), compounds of the present invention wherein $Y^2$ is an oxygen atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-4), compounds of the present invention wherein $Y^2$ is an oxygen atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-4), compounds of the present invention wherein $Y^2$ is an oxygen atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-4), compounds of the present invention wherein $Y^2$ is an oxygen atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-4), compounds of the present invention wherein $Y^2$ is an oxygen atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-4), compounds of the present invention wherein $Y^2$ is an oxygen atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

(X-5)

In the formula (X-5), compounds of the present invention wherein $Y^2$ is a sulfur atom, $G^1$ is CH, $G^2$ is CH, and $R^1$, $R^2$, $A^3$ and n are the combinations shown in [Table 1] to [Table 17].

In the formula (X-5), compounds of the present invention wherein $Y^2$ is a sulfur atom, $G^1$ is CH, $G^2$ is $CR^6$, $R^6$ is $CF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is CH, $G^2$ is $CR^6$, $R^6$ is $OCF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is CH, $G^2$ is $CR^6$, $R^6$ is $CF_2CF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is CH, $G^2$ is $CR^6$, $R^6$ is $SCF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is CH, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is $SOCF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is $SO_2CF_3$, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-5), compounds of the present invention wherein $Y^2$ is a sulfur atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

In the formula (X-5), compounds of the present invention wherein $Y^2$ is an oxygen atom, $G^1$ is a nitrogen atom, $G^2$ is CH, and $R^1$, $R^2$, $A^3$ and n are the combinations shown in [Table 1] to [Table 17].

In the formula (X-5), compounds of the present invention wherein $Y^2$ is an oxygen atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-5), compounds of the present invention wherein $Y^2$ is an oxygen atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-5), compounds of the present invention wherein $Y^2$ is an oxygen atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-5), compounds of the present invention wherein $Y^2$ is an oxygen atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-5), compounds of the present invention wherein $Y^2$ is an oxygen atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-5), compounds of the present invention wherein $Y^2$ is an oxygen atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-5), compounds of the present invention wherein $Y^2$ is an oxygen atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

(X-6)

In the formula (X-6), compounds of the present invention wherein $Y^2$ is a sulfur atom, $G^1$ is a nitrogen atom, $G^2$ is CH, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is $CF_3$, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is $OCF_3$, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is $CF_2CF_3$, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is $SCF_3$, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is $SOCF_3$, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is $SO_2CF_3$, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is a 2-pyridyl group, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is a 5-$CF_3$ pyridin-2-yl group, and $R^1$, $R^2$, $A^3$ and n are the combinations shown in [Table 1] to [Table 17].

In the formula (X-6), compounds of the present invention wherein $Y^2$ is a sulfur atom, $G^1$ is a nitrogen atom, $G^2$ is $CR^6$, $R^6$ is a pyrimidin-2-yl group, and $R^1$, $R^2$, $A^3$ and n are the combinations shown in [Table 1] to [Table 17].

(X-7)

In the formula (X-7), compounds of the present invention wherein $Y^2$ is a sulfur atom, $G^1$ is a nitrogen atom, $G^2$ is CH, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, $R^6$ is $CF_3$, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, $R^6$ is $OCF_3$, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, $R^6$ is $CF_2CF_3$, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, $R^6$ is $SCF_3$, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, $R^6$ is $SOCF_3$, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, $R^6$ is $SO_2CF_3$, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, $R^6$ is a 2-pyridyl group, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, $R^6$ is a 5-$CF_3$ pyridin-2-yl group, and $R^1, R^2, A^3$ and n are the combinations shown in [Table 1] to [Table 17].

In the formula (X-7), compounds of the present invention wherein $Y^2$ is a sulfur atom, $G^1$ is a nitrogen atom, $G^2$ is $CR^6$, R is a pyrimidin-2-yl group, and $R^1, R^2, A^3$ and n are the combinations shown in [Table 1] to [Table 17].

(X-8)

In the formula (X-8), compounds of the present invention wherein $G^1$ is CH, $G^2$ is CH, $G^3$ is CH, and $R^1, R^2, A^3$ and n are the combinations shown in [Table 1] to [Table 17].

In the formula (X-8), compounds of the present invention wherein $G^1$ is CH, $G^2$ is $CR^6$, $R^6$ is $CF_3$, $G^3$ is CH, and $R^1, R^2, A^3$ and n are the combinations shown in [Table 1] to [Table 17].

In the formula (X-8), compounds of the present invention wherein $G^1$ is CH, $G^2$ is $CR^6$, $R^6$ is $OCF_3$, $G^3$ is CH, and $R^1, R^2, A^3$ and n are the combinations shown in [Table 1] to [Table 17]

In the formula (X-8), compounds of the present invention wherein $G^1$ is CH, $G^2$ is $CR^6$, $R^6$ is $CF_2CF_3$, $G^3$ is CH, and $R^1, R^2, A^3$ and n are the combinations shown in [Table 1] to [Table 17].

In the formula (X-8), compounds of the present invention wherein $G^1$ is CH, $G^2$ is $CR^6$, $R^6$ is $SCF_3$, $G^3$ is CH, and $R^1, R^2, A^3$ and n are the combinations shown in [Table 1] to [Table 17]

In the formula (X-8), compounds of the present invention wherein $G^1$ is CH, $G^2$ is CH, $G^3$ is a nitrogen atom, and $R^1, R^2, A^3$ and n are the combinations shown in [Table 1] to [Table 17].

In the formula (X-8), compounds of the present invention wherein $G^1$ is CH, $G^2$ is $CR^6$, $R^6$ is $CF_3$, $G^3$ is a nitrogen atom, and $R^1, R^2, A^3$ and n are the combinations shown in [Table 1] to [Table 17].

In the formula (X-8), compounds of the present invention wherein $G^1$ is CH, $G^2$ is $CR^6$, $R^6$ is $OCF_3$, $G^3$ is a nitrogen atom, and $R^1, R^2, A^3$ and n are the combinations shown in [Table 1] to [Table 17].

In the formula (X-8), compounds of the present invention wherein $G^1$ is CH, $G^2$ is $CR^6$, $R^6$ is $CF_2CF_3$, $G^3$ is a nitrogen atom, and $R^1, R^2, A^3$ and n are the combinations shown in [Table 1] to [Table 17].

In the formula (X-8), compounds of the present invention wherein $G^1$ is CH, $G^2$ is $CR^6$, $R^6$ is $SCF_3$, $G^3$ is a nitrogen atom, and $R^1, R^2, A^3$ and n are the combinations shown in [Table 1] to [Table 17].

In the formula (X-8), compounds of the present invention wherein $G^1$ is a nitrogen atom, $G^2$ is CH, $G^3$ is a nitrogen atom, and $R^1, R^2, A^3$ and n are the combinations shown in [Table 1] to [Table 17].

In the formula (X-8), compounds of the present invention wherein $G^1$ is a nitrogen atom, $G^2$ is $CR^6$, $R^6$ is $CF_3$, $G^3$ is a nitrogen atom, and $R^1, R^2, A^3$ and n are the combinations shown in [Table 1] to [Table 17].

In the formula (X-8), compounds of the present invention wherein $G^1$ is a nitrogen atom, $G^2$ is $CR^6$, $R^6$ is $OCF_3$, $G^3$ is a nitrogen atom, and $R^1, R^2, A^3$ and n are the combinations shown in [Table 1] to [Table 17].

In the formula (X-8), compounds of the present invention wherein $G^1$ is a nitrogen atom, $G^2$ is $CR^6$, $R^6$ is $CF_2CF_3$, $G^3$ is a nitrogen atom, and $R^1, R^2, A^3$ and n are the combinations shown in [Table 1] to [Table 17].

In the formula (X-8), compounds of the present invention wherein $G^1$ is a nitrogen atom, $G^2$ is $CR^6$, $R^6$ is $SCF_3$, $G^3$ is a nitrogen atom, and $R^1, R^2, A^3$ and n are the combinations shown in [Table 1] to [Table 17].

In the formula (X-8), compounds of the present invention wherein $G^1$ is a nitrogen atom, $G^2$ is CH, $G^3$ is CH, and $R^1, R^2, A^3$ and n are the combinations shown in [Table 1] to [Table 17].

In the formula (X-8), compounds of the present invention wherein $G^1$ is a nitrogen atom, $G^2$ is $CR^6$, $R^6$ is $CF_3$, $G^3$ is CH, and $R^1, R^2, A^3$ and n are the combinations shown in [Table 1] to [Table 17].

In the formula (X-8), compounds of the present invention wherein $G^1$ is a nitrogen atom, $G^2$ is $CR^6$, $R^6$ is $OCF_3$, $G^3$ is CH, and $R^1, R^2, A^3$ and n are the combinations shown in [Table 1] to [Table 17].

In the formula (X-8), compounds of the present invention wherein $G^1$ is a nitrogen atom, $G^2$ is $CR^6$, $R^6$ is $CF_2CF_3$, $G^3$ is CH, and $R^1$, $R^2$, $A^3$ and n are the combinations shown in [Table 1] to [Table 17].

In the formula (X-8), compounds of the present invention wherein $G^1$ is a nitrogen atom, $G^2$ is $CR^6$, $R^6$ is $SCF_3$, $G^3$ is CH, and $R^1$, $R^2$, $A^3$ and n are the combinations shown in [Table 1] to [Table 17].

Examples of the pest on which the composition of the present invention has an effect include arthropod pests such as pest insects and pest mites and nematoda. Specifically, examples of the pests include those shown below.

Hemiptera: Delphacidae such as *Laodelphax striatellus, Nilaparvata lugens*, and *Sogatella furcifera*, Deltocephalidae such as *Nephotettix cincticeps, Nephotettix virescens*, and *Empoasca onukii*, Aphididae such as *Aphis gossypii, Myzus persicae, Brevicoryne brassicae, Aphis spiraecola, Macrosiphum euphorbiae, Aulacorthum solani, Rhopalosiphum padi, Toxoptera citricidus*, and *Hyalopterus pruni*, Pentatomidae such as *Nezara antennata, Riptortus clavetus, Leptocorisa chinensis, Eysarcoris parvus*, and *Halyomorpha mista*, Aleyrodidae such as *Trialeurodes vaporariorum, Bemisia tabaci, Dialeurodes citri*, and *Aleurocanthus spiniferus*, Coccidae such as *Aonidiella aurantii, Comstockaspis perniciosa, Unaspis citri, Ceroplastes rubens, Icerya purchasi, Planococcus kraunhiae, Pseudococcus longispinis*, and *Pseudaulacaspis pentagona*, Tingidae, Cimicoidea such as *Cimex lectularius*, and Psyliidae.

Lepidoptera: Pyralidae such as *Chilo suppressalis, Tryporyza incertulas, Cnaphalocrocis medinalis, Notarcha derogata, Plodia interpunctella, Ostrinia furnacalis, Hellula undalis*, and *Pediasia teterrellus*, Noctuidae such as *Spodoptera litura, Spodoptera exigua, Pseudaletia separata, Mamestra brassicae, Agrotis ipsilon, Plusia nigrisigna, Trichoplusia* spp., *Heliothis* spp., and *Helicoverpa* spp., Pieridae such as *Pieris rapae, Adoxophyes* spp., Tortricidae such as *Grapholita molesta, Leguminivora glycinivorella, Matsumuraeses azukivora, Adoxophyes orana fasciata, Adoxophyes honmai., Homona magnanima, Archips fuscocupreanus*, and *Cydia pomonella*, Gracillariidae such as *Caloptilia theivora* and *Phyllonorycter ringoneella*, Carposinidae such as *Carposina niponensis*, Lyonetiidae such as *Lyonetia* spp., Lymantriidae such as *Lymantria* spp. and *Euproctis* spp., Yponomeutidae such as *Plutella xylostella*, Gelechiidae such as *Pectinophora gossypiella* and *Phthorimaea operculella*, Arctiidae such as *Hyphantria cunea*, and Tineidae such as *Tinea translucens* and *Tineola bisselliella*.

Thysanoptera: Thripidae such as *Frankliniella occidentalis, Thrips parmi, Scirtothrips dorsalis, Thrips tabaci*, and *Frankliniella intonsa*.

Diptera: *Culex* such as *Culex pipiens pallens, Culex tritaeniorhynchus*, and *Culex quinquefasciatus, Aedes* spp. such as *Aedes aegypti* and *Aedes albopictus, Anopheles* spp. such as *Anopheles sinensis*, Chironomidae, Muscidae such as *Musca domestica* and *Muscina stabulans*, Calliphoridae, Sarcophagidae, Fanniidae, Anthomyiidae such as *Delia platura* and *Delia antiqua*, Agromyzidae such as *Agromyza oryzae, Hydrellia griseola, Liriomyza sativae, Liriomyza trifolii*, and *Chromatomyia horticola*, Chloropidae such as *Chlorops oryzae*, Tephritidae such as *Dacus cucurbitae* and *Ceratitis capitata*, Drosophilidae, Phoridae such as *Megaselia spiracularis*, Psychodidae such as *Clogmia albipunctata*, Sciaridae, Simuliidae, Tabanidae such as *Tabanus trigonus, Stomoxys*, and Stomoxyidae.

Coleoptera: Corn rootworm such as *Diabrotica virgifera virgifera* and *Diabrotica undecimpunctata howardi*, Scarabaeidae such as *Anomala cuprea, Anomala rufocuprea*, and *Popillia japonica*, Curculionidae such as *Sitophilus zeamais, Lissorhoptrus oryzophilus, Callosobruchuys chienensis, Echinocnemus squameus, Anthonomus grandis*, and *Sphenophorus venatus*, Tenebrionidae such as *Tenebrio molitor* and *Tribolium castaneum*, Chrysomelidae such as *Oulema oryzae, Aulacophora femoralis, Phyllotreta striolata*, and *Leptinotarsa decemlineata*, Dermestidae such as *Anthrenus verbasci* and *Dermestes maculates*, Anobiidae such as *Lasioderma serricorne, Epilachna* such as *Epilachna vigintioctopunctata*, Lyctidae such as *Lyctus brunneus* and *Tomicus piniperda*, Bostrychidae, Ptinidae, Cerambycidae such as *Anoplophora malasiaca, Agriotes* spp., and *Paederus fuscipes*.

Orthoptera: *Locusta migratoria, Gryllotalpa africana, Oxya yezoensis, Oxya japonica*, and Grylloidea.

Siphonaptera: *Ctenocephalides felis, Ctenocephalides canis, Pulex irritans, Xenopsylla cheopis*, and the like.

Anoplura: *Pediculus humanus corporis, Pediculus humanus humanus, Phthirus pubis, Haematopinus eurysternus, Dalmalinia ovis, Haematopinus suis, Linognathus setosus*, and the like.

Mallophaga: *Dalmalinia ovis, Dalmalinia bovis, Menopon gallinae, Trichodectes canis, Felicola subrostrata*, and the like.

Hymenoptera: Formicidae such as *Monomorium pharaosis, Formica fusca japonica, Ochetellus glaber, Pristomyrmex pungens, Pheidole noda, Acromyrmex* spp., *Solenopsis* spp., and *Linepithema humile*, Vespidae, Bethylidae, and Tenthredinidae such as *Athalia rosae* and *Athalia japonica*.

Nematoda: *Aphelenchoides besseyi, Nothotylenchus acris, Meloidogyne incognita, Meloidogyne hapla, Meloidogyne javanica, Heterodera glycines, Globodera rostochiensis, Pratylenchus coffeae*, and *Pratylenchus neglectus*.

Blattodea: *Blattella germanica, Periplaneta fuliginosa, Periplaneta americana, Periplaneta brunnea*, and *Blatta orientalis*.

Isoptera: *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapritermes nitobei, Sinocapritermes mushae*, and the like.

Acarina: Tetranychidae such as *Tetranychus urticae, Tetranychus kanzawai, Panonychus citri, Panonychus ulmi*, and *Oligonychus* spp., Eriophyidae such as *Aculops pelekassi, Phyllocoptruta citri, Aculops lycopersici, Calacarus carinatus, Acaphylla theavagrans, Eriophyes chibaensis*, and *Aculus schlechtendali*, Tarsonemidae such as *Polyphagotarsonemus latus*, Tenuipalpidae such as *Brevipalpus phoenicis*, Tuckerellidae, Metastigmata such as *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus*, and *Rhipicephalus sanguineus*, Acaridae such as *Tyrophagus putrescentiae* and *Tyrophagus similis*, Pyroglyphidae such as *Dermatophagoides farinae* and *Dermatophagoides ptrenyssnus*, Cheyletidae such as *Cheyletus eruditus, Cheyletus malaccensis, Cheyletus moorei*, and *Cheyletiella yasguri*, Sarcoptidae such as *Octodectes cynotis* and *Sacroptes scabiei*, Demodicidae such as *Demodex canis*, Listrophoridae, Oribatei, Dermanyssidae such as *Ornithonyssus bacoti, Ornithonyssus sylvairum*, and *Dermanyssus*

*gallinae*, Trombiculidae such as *Leptotrombidium akamushi*, Arachnida such as *Chiracanthium japonicum* and *Latrodectus hasseltii*, and the like.

Chilopoda: *Thereuonema hilgendorfi, Scolopendra subspinipes*, and the like.

Diplopoda: *Oxidus gracilis, Nedyopus tambanus*, and the like.

Isopoda: *Armadillidium vulgare*, and the like.

Gastropoda: *Limax marginatus, Limax flavus*, and the like.

The pest control agent of the present invention contains the compound of the present invention and an inert carrier. The pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powders, flowables, microcapsule formulations, aerosols, fumigants, poisonous baits, resin formulations, shampoo agent, paste formulation, foam agent, carbon dioxide preparation, tablet, and the like. These formulations may be processed into mosquito repellent coil, electric mosquito repellent mat, mosquito repellent liquid formulation, smoking agent, fumigant, sheet formulation, spot-on agent, or oral treatment agent, and used.

The pest control agent of the present invention usually contains the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), chemical fertilizers (ammonium sulfate, ammonium phosphate, ammonium nitrate, urea, ammonium chloride, etc.) and the like, and synthetic resins (polyester resins such as polypropylene, polyacrylonitrile, polymethylmethacrylate and polyethylene terephthalate, nylon resins such as nylon-6, nylon-11 and nylon-66, polyamide resin, polyvinyl chloride, polyvinylidene chloride, vinyl chloride-propylene copolymer, and the like).

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants, and alkylsulfates, alkylbenzene sulfonates and alkylsulfates.

The other auxiliaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

Examples of a base material of the resin formulation include vinyl chloride polymer, polyurethane and the like, and a plasticizer such as ester phthalates (dimethyl phthalate, dioctyl phthalate, etc.), ester adipates or stearic acid may be added to these base materials as necessary. The resin formulation is obtained by kneading a compound into the base material using an ordinary kneading apparatus, then molding it by injection molding, extrusion molding, press molding or the like, and can be processed into a plate, film, taped, reticular or string resin formulation by further undergoing molding or cutting step as necessary. These resin formulations are processed into, for example, a collar for animal, an ear tag for animal, a sheet formulation, an induction cord, and a gardening pole.

Examples of a base material of the poisonous bait include grain powder, vegetable oil, sugar, crystalline cellulose and the like, and further, an antioxidant such as dibutylhydroxytoluene and nordihydroguaiaretic acid, a preservative such as dehydroacetic acid, a substance for preventing erroneous eating from children and pets such as red pepper powder, a pest attractant such as cheese flavor, onion flavor and peanut oil or the like is added as necessary.

The method for controlling pests of the present invention is carried out by applying an effective amount of the composition of the present invention to a pest directly and/or pest habitats (plants, soil, in-house, animal body, etc.). In the method for controlling pests of the present invention, the compound is usually used in the form of the pest control agent of the present invention.

When the pest control agent of the present invention is used in pest controlling in the agricultural field, the application amount is usually 1 to 10000 g per the amount of the compound of the present invention per 10000 $m^2$. When the pest control agent of the present invention is formulated into an emulsifiable concentrate, a wettable powder, a flowable or the like, the pest control agent is usually diluted with water so as to have a concentration of the active ingredient of 0.01 to 10000 ppm and applied, and dust formulations, granules and the like are usually applied as they are.

These formulations and formulation solutions diluted with water may be directly treated by spraying on a pest or a plant such as crops which should be protected from pests, and also may be treated on a soil in order to control a pest that inhabits in the soil of cultivated land.

Also, the resin formulation processed into a sheet or string can be also treated by a method such as winding it around crops, spreading it in the vicinity of crops, or spreading it to the soil around crop roots.

When the pest control agent of the present invention is used in controlling the pest that inhabits in the house, the application amount is usually 0.01 to 1000 mg in an amount of the compound of the present invention per 1 $m^2$ of an area to be treated, in the case of using it on a planar area, and is usually 0.01 to 500 mg in an amount of the compound of the present invention per 1 $m^2$ of a space to be treated, in the case of using it in a space. When the pest control agent of the present invention is formulated into an emulsifiable concentrate, a wettable powder, a flowable or the like, the pest control agent is usually diluted with water so as to have a concentration of the active ingredient of 0.1 to 10000 ppm and applied, and oil formulations, aerosols, fumigants, poisonous baits and the like are applied as they are.

When the arthropod pest control agent of the present invention is used in the control of external parasites on livestock such as cows, horses, pigs, sheep, goats and chickens, and small animals such as dogs, cats, rats and mice, veterinary known methods can be applied to the animals. As specific methods, the formulation is administered, for example, by way of a tablet, mixing in feed, a suppository and injection (intramuscular, subcutaneous, intravenous, intraperitoneal injections, etc.), when systemic control is intended, and the formulation is used, for example, by way of spraying an oil solution or aqueous solution, pour-on or spot-on treatment, washing an animal with a shampoo formulation, or putting a collar or ear tag made of a resin formulation to an animal, when non-systemic control is intended. The amount of the compound of the present invention when administered to an animal body is usually in the range from 0.1 to 1000 mg per 1 kg of the weight of an animal.

The pest control agent of the present invention can be used in the farmland where the following "crops" are grown.

Crops: corn, rice, wheat, barley, rye, oat, sorghum, cotton, soybean, peanut, sarrazin, sugar beet, rapeseed, sunflower, sugar cane, tobacco, etc.

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, *macadamia* nut, etc.), berry fruits (blueberry, cranberry, blackberry, raspberry, etc.), grape, persimmon, olive, loquat, banana, coffee, date, coconut, oil palm, etc.

Trees other than fruit trees: tea, mulberry, flowering trees and shrubs (azalea, camellia, hydrangea, sasanqua, *Illicium religiosum*, cherry tree, tulip tree, crape myrtle, fragrant olive, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horsechestnut, etc.), sweet viburnum, *Podocarpus macrophyllus*, Japanese cedar, Japanese cypress, croton, spindle tree, Chinese hawthorn, etc.

Lawn: zoysia (Japanese lawn grass, mascarene grass, etc.), Bermuda grass (*Cynodon dactylon*, etc.), bent grass (creeping bent grass, *Agrostis stolonifera, Agrostis tenuis*, etc.), bluegrass (Kentucky bluegrass, rough bluegrass, etc.), fescue (tall fescue, chewing fescue, creeping fescue, etc.), ryegrass (darnel, perennial ryegrass, etc.), cocksfoot, timothy grass, etc.

Others: flowers (rose, carnation, chrysanthemum, *Eustoma grandiflorum* Shinners (prairie gentian), gypsophila, gerbera, pot marigold, salvia, petunia, verbena, tulip, aster, gentian, lily, pansy, cyclamen, orchid, lily of the valley, lavender, stock, ornamental kale, primula, poinsttia, gladiolus, cattleya, daisy, cymbidium, begonia, etc.), bio-fuel plants (*Jatropha, curcas*, safflower, *Camelina alyssum*, switchgrass, miscanthus, reed canary grass, *Arundo donax*, kenaf, cassava, willow, algae, etc.), foliage plants, etc.

The "crops" also contains genetically modified crops.

The pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist include the following:

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether), dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, and 2,3,5,6-tetrafluoro-4-(methoxymethyl)benzyl (1RS,3RS;1RS,3SR)-2,2-dimethyl-3-(2-methyl-1-propenyl)cyclopropanecarboxylate, 2,3,5,6-tetrafluoro-4-(methoxymethyl)benzyl(EZ)-(1RS,3RS;1RS,3SR)-2,2-dimethyl-3-(2-cyano-1-propenyl)cyclopropanecarboxylate.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, and triazuron.
(7) Phenylpyrazole-Based Compounds
acetoprole, ethiprole, fipronil, vaniliprole, pyriprole, and pyrafluprole.
(8) Bt Toxins
Living spores derived from *Bacillus thuringiensis* and produced crystalline toxins and mixtures thereof.
(9) Hydrazine Compounds
chromafenozide, halofenozide, methoxyfenozide, and tebufenozide.
(10) Organic Chlorine Compounds
aldrin, dieldrin, dienochlor, endosulfan, and methoxychlor.
(11) Other Active Ingredients of Insecticide
machine oil, nicotine-sulfate; avermectin-B), bromopropylate, buprofezin, chlorphenapyr, cyantraniliprole, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, cyantraniliprole, compounds represented by the following formula (K)

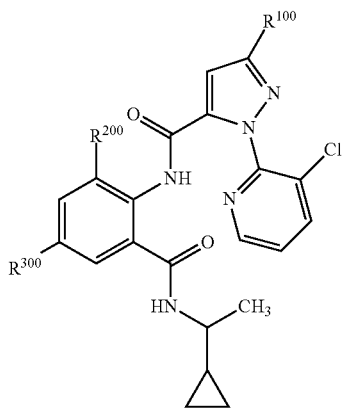

(K)

wherein
$R^{100}$ represents chlorine, bromine or a trifluoromethyl group,
$R^{200}$ represents chlorine, bromine or a methyl group, and
$R^{300}$ represents chlorine, bromine or a cyano group, and compounds represented by the following formula (L)

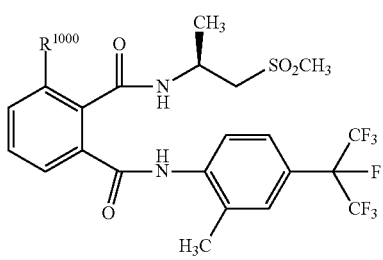

(L)

wherein
$R^{1000}$ represents chlorine, bromine or iodine.

Active Ingredients of Miticide
acequinocyl, amitraz, benzoximate, bifenaate, bromopropylate, chinomethionat, chlorobenzilate, CPCBS (chlorfenson), clofentezine, cyflumetofen, kelthane(dicofol), etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.
Active Ingredients of Nematicide
DCIP, fosthiazate, levamisol, methylsothiocyanate, morantel tartarate, and imicyafos.
Active Ingredients of Fungicide
azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol; cyclic amine fungicidal compounds such as fenpropimorph, tridemorph, and fenpropidin; benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.
Active Ingredients of Herbicide
(1) Phenoxy Fatty Acid Herbicidal Compounds
2,4-PA, MCP, MCPB, phenothiol, mecoprop, fluoroxypyr, triclopyr, clomeprop, and naproanilide.
(2) Benzoate Herbicidal Compounds
2,3,6-TBA, dicamba, clopyralid, picloram, aminopyralid, quinclorac, and quinmerac.
(3) Urea Herbicidal Compounds
diuron, linuron, chlortoluron, isoproturon, fluometuron, isouron, tebuthiuron, methabenzthiazuron, cumyluron, daimuron, and methyl-daimuron.
(4) Triazine Herbicidal Compounds
atrazine, ametoryn, cyanazine, simazine, propazine, simetryn, dimethametryn, prometryn, metribuzin, triaziflam, and indaziflam.
(5) Bipyridinium Herbicidal Compounds
paraquat, and diquat.
(6) Hydroxybenzonitrile Herbicidal Compounds
bromoxynil, and ioxynil.
(7) Dinitroaniline Herbicidal Compounds
pendimethalin, prodiamine, and trifluralin.
(8) Organophosphorus Herbicidal Compounds
amiprofos-methyl, butamifos, bensulide, piperophos, anilofos, glyphosate, glufosinate, glufosinate-P, and bialaphos.
(9) Carbamate Herbicidal Compounds
di-allate, tri-allate, EPTC, butylate, benthiocarb, esprocarb, molinate, dimepiperate, swep, chlorpropham, phenmedipham, phenisopham, pyributicarb, and asulam.
(10) Acid Amide Herbicidal Compounds
propanil, propyzamide, bromobutide, and etobenzanid.
(11) Chloroacetanilide Herbicidal Compounds
acetochlor, alachlor, butachlor, dimethenamid, propachlor, metazachlor, metolachlor, pretilachlor, thenylchlor, and pethoxamid.

(12) Diphenyl Ether Herbicidal Compounds
   acifluorfen-sodium, bifenox, oxyfluorfen, lactofen, fomesafen, chlomethoxynil, and aclonifen.
(13) Cyclic Imide Herbicidal Compounds
   oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) Pyrazole Herbicidal Compounds
   benzofenap, pyrazolate, pyrazoxyfen, topramezone, and pyrasulfotole.
(15) Triketone Herbicidal Compounds
   isoxaflutole, benzobicyclon, sulcotrione, mesotrione, tembotrione, and tefuryltrione.
(16) Aryloxyphenoxypropionate Herbicidal Compounds
   clodinafop-propargyl, cyhalofop-butyl, diclofop-methyl, fenoxaprop-ethyl, fluazifop-butyl, haloxyfop-methyl, and quizalofop-ethyl, metamifop.
(17) Trione Oxime Herbicidal Compounds
   alloxydim-sodium, sethoxydim, butroxydim, clethodim, cloproxydim, cycloxydim, tepraloxydim, tralkoxydim, and profoxydim.
(18) Sulfonyl Urea Herbicidal Compounds
   chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds
   imazamethabenz-methyl, imazamethapyr, imazamox, imazapyr, imazaquin, and imazethapyr.
(20) Sulfonamide Herbicidal Compounds
   flumetsulam, metosulam, diclosulam, florasulam, cloransulam-methyl, penoxsulam, and pyroxsulam.
(21) Pyrimidinyloxybenzoate Herbicidal Compounds
   pyrithiobac-sodium, bispyribac-sodium, pyriminobac-methyl, pyribenzoxim, pyriftalid, and pyrimisulfan.
(22) Other Herbicidal Compounds
   bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.
   Active Ingredients of Plant Growth Regulator
   hymexazol, paclobutrazol, uniconazole-P, inabenfide, prohexadione-calcium, aviglycine), 1-naphthalene acetamide, abscisic acid, indolebutyric acid, ethychlozate, ethephon, cloxyfonac, chlormequat, dichlorprop, gibberellins, prohydrojasmon, benzyladenine, forchlorfenuron, maleic hydrazide, calcium peroxide, mepiquat-chlorideand 4-CPA (4-chlorophenoxyacetic acid).
   Active Ingredients of Synergist
   piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, CH$_3$I, t-phenylbutenone, diethylmaleate, DMC, FDMC, ETP, and ETN.

EXAMPLES

Hereinbelow, the present invention will be further described in detail by production examples, formulation examples, test examples, and the like. However, the present invention is not limited to these examples.

Here, in production examples and reference production examples, unless otherwise specified, $^1$H-NMR shows a data obtained by using tetramethylsilane as an internal standard in a deuterated chloroform solvent.

Production Example 1

41 mg of sodium hydride (60% oil-based) was suspended into 4 ml of 1-methyl-2-pyrrolidone (NMP), and 0.13 g of 2-ethylthioimidazol was added under ice cooling. After stirring the mixture for 10 minutes, 0.2 g of 2-chloro-3-methyl-6-trifluoromethyl-3H-imidazo[4,5,b]pyridine was added, and the mixture was stirred under room temperature for 3 hours. Water was poured, and the deposited precipitate was obtained by filtration and was applied to a silica gel column chromatography to obtain 0.28 g of 2-(2-ethylthio-3H-imidazol-3-yl)-3-methyl-6-trifluoromethyl-3H-imidazo[4,5,b]pyridine (Compound of Present Invention (1)).

(Compound of Present Invention (1))

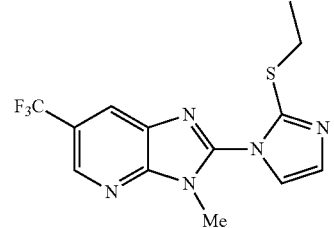 [SMILES: CCSc1nccn1-c1nc2cc(C(F)(F)F)cnc2n1C]

$^1$H-NMR: 8.77 (d, 1H), 8.35 (d, 1H), 7.28-7.31 (m, 2H), 3.80 (s, 3H), 3.17 (q, 2H), 1.36 (t, 3H)

Production Example 2

0.22 g of 3-chloroperoxybenzoic acid (purity of 65% or more) was added to 3 ml of a solution of 0.13 g of 2-(2-ethylthio-3H-imidazol-3-yl)-3-methyl-6-trifluoromethyl-3H-imidazo[4,5,b]pyridine in chloroform under ice cooling, and the mixture was stirred at room temperature for 1 hour. A 10% aqueous sodium thiosulfate solution was poured into the reaction mixture, and the mixture was extracted with chloroform. The organic layer was washed with a saturated aqueous sodium bicarbonate solution, then dried over anhydrous magnesium sulfate and concentrated under reduced pressure. The resulting residue was applied to a silica gel column chromatography to obtain 0.12 g of 2-(2-ethylsulfonyl-3H-imidazol-3-yl)-3-methyl-6-trifluoromethyl-3H-imidazo[4,5,b]pyridine (Compound of Present Invention (2)).

103
(Compound of Present Invention (2))

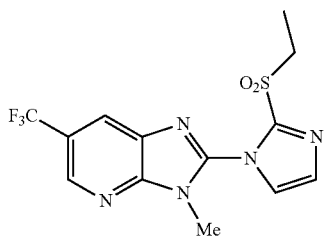 [SMILES: CCS(=O)(=O)c1nccn1-c1nc2cc(C(F)(F)F)cnc2n1C]

¹H-NMR: 8.80 (d, 1H), 8.35 (d, 1H), 7.50-7.51 (m, 1H), 7.40-7.41 (m, 1H), 3.78 (s, 3H), 3.46 (q, 2H), 1.37 (t, 3H)

Production Example 3

0.32 g of sodium ethanethiolate was added to a mixture of 0.71 g of 2-(3-chloro-thiophen-2-yl)-3-methyl-6-trifluoromethylthio-3H-imidazo[4,5-b]pyridine and 4 ml of NMP, under ice cooling, and the mixture was stirred at 70° C. for 4 hours. Water was poured into the reaction mixture, and the mixture was extracted with ethyl acetate. The organic layer was washed with water and dried over anhydrous magnesium sulfate, then concentrated under reduced pressure and applied to a silica gel column chromatography to obtain 0.57 g of 2-(3-ethylthiophen-2-yl)-3-methyl-6-trifluoromethylthio-3H-imidazo[4,5-b]pyridine (Compound of Present Invention (3)).

(Compound of Present Invention (3))

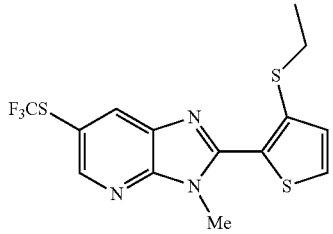

¹H-NMR: 8.64 (d, 1H), 8.39 (d, 1H), 7.62 (d, 1H), 7.20 (d, 1H), 3.96 (s, 3H), 2.90 (q, 2H), 1.26 (t, 3H)

Production Example 4

0.09 g of 3-chloroperoxybenzoic acid (purity of 65% or more) was added to 0.09 g of a solution of 0.06 g of 2-(3-ethylthiophen-2-yl)-3-methyl-6-trifluoromethylthio-3H-imidazo[4,5-b]pyridine in 3 ml of chloroform under ice cooling, and the mixture was stirred at room temperature for 1 hour. A 10% aqueous sodium thiosulfate solution was poured into the reaction mixture, and the mixture was extracted with chloroform. The organic layer was washed with a saturated aqueous sodium bicarbonate solution, then dried over anhydrous magnesium sulfate and concentrated under reduced pressure. The resulting residue was applied to a silica gel column chromatography to obtain 0.06 g of 2-(3-ethylsulfonylthiophen-2-yl)-3-methyl-6-trifluoromethyl thio-3H-imidazo[4,5-b]pyridine (Compound of Present Invention (4)).

104
(Compound of Present Invention (4))

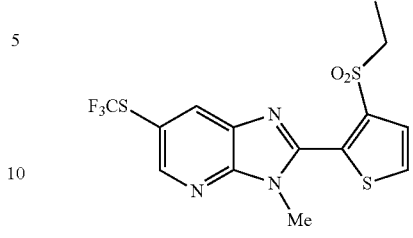

¹H-NMR: 8.70 (d, 1H), 8.38 (d, 1H), 7.73 (d, 1H), 7.61 (d, 1H), 3.85 (s, 3H), 3.31 (q, 2H), 1.30 (t, 3H)

Production Example 5

A mixture of 0.12 g of N²-methyl-5-trifluoromethylpyridine-2,3-diamine, 0.2 g of 3-ethylthio-5-trifluoromethylthiophene-2-carboxylic acid, 0.15 g of EDCI hydrochloride, 9 mg of HOBt and 3 ml of pyridine was stirred at 80° C. for 6 hours. Water was poured into the cooled reaction mixture, and the mixture was extracted with ethyl acetate. The organic layer was washed with water and dried over anhydrous magnesium sulfate, then concentrated under reduced pressure and applied to a silica gel column chromatography to obtain 0.3 g of 2-(3-ethylthio-5-trifluoromethylthiophen-2-yl)-3-methyl-6-t rifluoromethyl-3H-imidazo[4,5,b]pyridine (Compound of Present Invention (5)).

(Compound of Present Invention (5))

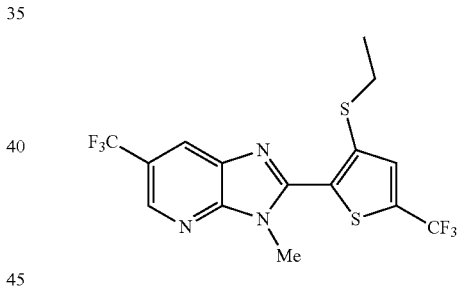

¹H-NMR: 8.74 (d, 1H), 8.35 (d, 1H), 7.51 (s, 3H), 3.99 (s, 3H), 2.92 (q, 2H), 1.27 (t, 3H)

Production Example 6

0.08 g of 3-chloroperoxybenzoic acid (purity of 65% or more) was added to a solution of 0.06 g of 2-(3-ethylthio-5-trifluoromethylthiophen-2-yl)-3-methyl-6-t rifluoromethyl-3H-imidazo[4,5,b]pyridine in 3 ml of chloroform under ice cooling, and the mixture was stirred for 2 hours and at room temperature for 1 hour. A 10% aqueous sodium thiosulfate solution was poured into the reaction mixture, and the mixture was extracted with chloroform. The organic layer was washed with a saturated aqueous sodium bicarbonate solution, then dried over anhydrous magnesium sulfate and concentrated under reduced pressure. The resulting residue was applied to a silica gel column chromatography to obtain 0.06 g of 2-(3-ethylsulfonyl-5-trifluoromethylthiophen-2-yl)-3-methyl-6-trifluoromethyl-3H-imidazo[4,5,b]pyridine (Compound of Present Invention (6)).

(Compound of Present Invention (6))

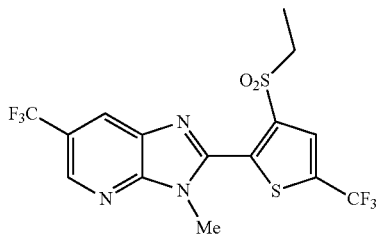 [SMILES: CCS(=O)(=O)c1cc(C(F)(F)F)sc1-c1nc2cc(C(F)(F)F)cnc2n1C]

¹H-NMR: 8.79 (d, 1H), 8.34 (d, 1H), 7.93 (s, 1H), 3.99 (s, 3H), 3.35 (q, 2H), 1.33 (t, 3H)

Production Example 7

A mixture of 0.15 g of N²-methyl-5-trifluoromethylpyridine-2,3-diamine, 0.2 g of 3-ethylthio-5-trifluoromethylthiophene-2-carboxylic acid, 0.15 g of EDCI hydrochloride, 9 mg of HOBt and 3 ml of pyridine was stirred at 80° C. for 6 hours. Water was poured into the cooled reaction mixture, and the mixture was extracted with ethyl acetate. The organic layer was washed with water and dried over anhydrous magnesium sulfate, then concentrated under reduced pressure and applied to a silica gel column chromatography to obtain 0.19 g of 2-(3-ethylthio-5-trifluoromethylthiophen-2-yl)-3-methyl-6-trifluoromethylthio-3H-imidazo[4,5,b]pyridine (Compound of Present Invention (7)).

(Compound of Present Invention (7))

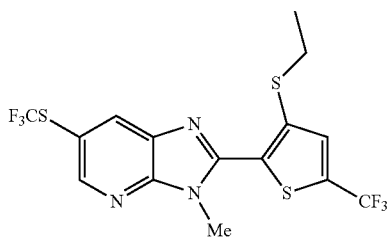

¹H-NMR: 8.68 (d, 1H), 8.42 (d, 1H), 7.51 (s, 1H), 3.98 (s, 3H), 2.93 (q, 2H), 1.28 (t, 3H)

Production Example 8

0.12 g of 3-chloroperoxybenzoic acid (purity of 65% or more) was added to 3 ml of a solution of 0.1 g of 2-(2-ethylthio-5-trifluoromethylthiophen-3-yl)-3-methyl-6-trifluoromethylthio-3H-imidazo[4,5,b]pyridine in chloroform under ice cooling, and the mixture was stirred for 2 hours and at room temperature for 1 hour. A 10% aqueous sodium thiosulfate solution was poured into the reaction mixture, and the mixture was extracted with chloroform. The organic layer was washed with a saturated aqueous sodium bicarbonate solution, then dried over anhydrous magnesium sulfate and concentrated under reduced pressure. The resulting residue was applied to a silica gel column chromatography to obtain 0.09 g of 2-(2-ethylsulfonyl-5-trifluoromethylthiophen-3-yl)-3-methyl-6-trifluoromethylthio-3H-imidazo[4,5,b]pyridine (Compound of Present Invention (8)).

(Compound of Present Invention (8))

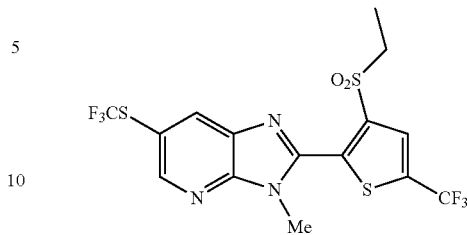

¹H-NMR: 8.81 (d, 1H), 8.60 (d, 1H), 7.94 (s, 1H), 3.92 (s, 3H), 3.36 (q, 2H), 1.34 (t, 3H)

Production Example 9

A mixture of 0.16 g of N²-methyl-5-pentafluoromethylpyridine-2,3-diamine, 0.2 g of 3-ethylthio-5-trifluoromethylthiophene-2-carboxylic acid, 0.15 g of EDCI hydrochloride, 9 mg of HOBt and 3 ml of pyridine was stirred at 80° C. for 6 hours. Water was poured into the cooled reaction mixture, and the mixture was extracted with ethyl acetate. The organic layer was washed with water and dried over anhydrous magnesium sulfate, then concentrated under reduced pressure and applied to a silica gel column chromatography to obtain 0.18 g of 2-(3-ethylthio-5-trifluoromethylthiophen-3-yl)-3-methyl-6-pentafluoromethylthio-3H-imidazo[4,5,b]pyridine (Compound of Present Invention (9)).

(Compound of Present Invention (9))

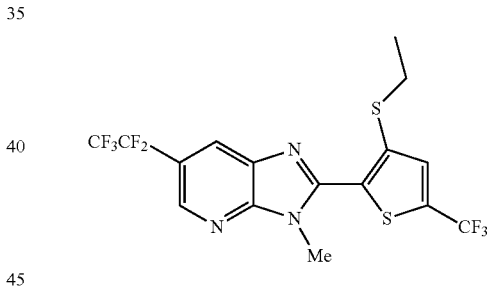

¹H-NMR: 8.69 (d, 1H), 8.33 (d, 1H), 7.51 (s, 1H), 4.00 (s, 3H), 2.93 (q, 2H), 1.28 (t, 3H)

Production Example 10

0.08 g of 3-chloroperoxybenzoic acid (purity of 65% or more) was added to 3 ml of a solution of 0.07 g of 2-(2-ethylthio-5-trifluoromethylthiophen-3-yl)-3-methyl-6-pentafluoroethyl-3H-imidazo[4,5,b]pyridine in chloroform under ice cooling, and the mixture was stirred for 2 hours and at room temperature for 1 hour. A 10% aqueous sodium thiosulfate solution was poured into the reaction mixture, and the mixture was extracted with chloroform. The organic layer was washed with a saturated aqueous sodium bicarbonate solution, then dried over anhydrous magnesium sulfate and concentrated under reduced pressure. The resulting residue was applied to a silica gel column chromatography to obtain 0.07 g of 2-(2-ethylsulfonyl-5-trifluoromethylthiophen-3-yl)-3-methyl-6-pentafluoroethyl-3H-imidazo[4,5,b]pyridine (Compound of Present Invention (10)).

(Compound of Present Invention (10))

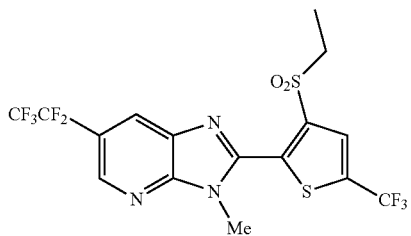

¹H-NMR: 8.74 (d, 1H), 8.32 (d, 1H), 7.27 (s, 1H), 3.90 (s, 3H), 3.36 (q, 2H), 1.34 (t, 3H)

Production Example 11

66 mg of sodium hydride (60% oil-based) was suspended into 3 ml of NMP, and 0.25 g of 5-ethylthio-2-trifluoroethyl-1H-1,2,4-triazole was added under ice cooling. After stirring the mixture for 10 minutes, 0.3 g of 2-chloro-3-methyl-6-trifluoromethyl-3H-imidazo[4,5,b]pyridine was added, and the mixture was stirred under room temperature for 3 hours. Water was poured, and the deposited precipitate was obtained by filtration and applied to a silica gel column chromatography to obtain 0.2 g of 2-(5-ethylthio-3-trifluoroethyl-1H-1,2,4-triazol-3-yl)-3-methyl-6-trifluoromethyl-3H-imidazo[4,5,b]pyridine (Compound of Present Invention (11)).

(Compound of Present Invention (11))

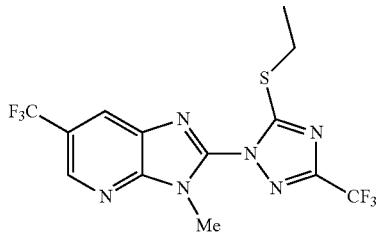 [SMILES: CCSc1nc(C(F)(F)F)nn1-c1nc2cc(C(F)(F)F)cnc2n1C]

¹H-NMR: 8.75 (d, 1H), 8.37 (d, 1H), 4.17 (s, 3H), 3.39 (q, 2H), 1.51 (t, 3H)

Production Example 12

0.19 g of 3-chloroperoxybenzoic acid (purity of 65% or more) was added to 3 ml of a solution of 0.1 g of 2-(5-ethylthio-3-trifluoroethyl-1H-1,2,4-triazol-3-yl)-3-methyl-6-trifluoromethyl-3H-imidazo[4,5,b]pyridine in chloroform under ice cooling, and the mixture was stirred for 2 hours and at room temperature for 1 hour. A 10% aqueous sodium thiosulfate solution was poured into the reaction mixture, and the mixture was extracted with chloroform. The organic layer was washed with a saturated aqueous sodium bicarbonate solution, then dried over anhydrous magnesium sulfate and concentrated under reduced pressure. The resulting residue was applied to a silica gel column chromatography to obtain 0.08 g of 2-(5-ethylsulfonyl-3-trifluoroethyl-1H-1,2,4-triazol-1-yl)-3-methyl-6-trifluoromethyl-3H-imidazo[4,5,b]pyridine (Compound of Present Invention (12)).

(Compound of Present Invention (12))

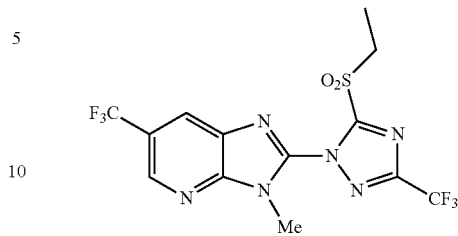

¹H-NMR: 8.86 (d, 1H), 8.42 (d, 1H), 3.94 (s, 3H), 3.79 (q, 2H), 1.53 (t, 3H)

Production Example 13

A mixture of 0.72 g of 2-(2-bromothiophen-3-yl)-3-methyl-6-trifluoromethyl-3H-imidazo[4,5-b]pyridine, 0.25 g of ethyl mercaptan sodium salt (80%), 0.08 g of copper iodide and 4 ml of N-methylpyrrolidinone was stirred at 70° C. for 4 hours. Water and aqueous ammonium (28%) were poured into the reaction mixture, and the mixture was extracted with ethyl acetate. The combined organic layers were dried over anhydrous sodium sulfate and then concentrated under reduced pressure. The resulting residue was applied to a silica gel column chromatography to obtain 0.30 g of 2-(2-ethylthiothiophen-3-yl)-3-methyl-6-trifluoromethyl-3H-imidazo[4,5-b]pyridine (Compound of Present Invention (13)).

(Compound of Present Invention (13))

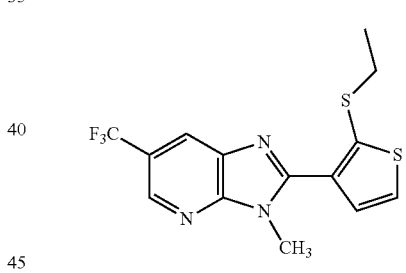

¹H-NMR (CDCl₃) δ: 8.70 (1H, d), 8.31 (1H, d), 7.48 (1H, d), 7.28 (1H, d), 3.90 (3H, s), 2.87 (2H, q), 1.24 (3H, t)

Production Example 14

0.20 g of 3-chloroperoxybenzoic acid (69 to 75%) was added to a mixture of 0.20 g of 2-(2-ethylthiothiophen-3-yl)-3-methyl-6-trifluoromethyl-3H-imidazo[4,5-b]pyridine and 3 ml of chloroform, under ice cooling, and the mixture was heated to room temperature and stirred for 2 hours. A saturated aqueous sodium bicarbonate solution and a saturated aqueous sodium thiosulfate solution were poured to the reaction mixture, and the mixture was extracted twice with ethyl acetate. The combined organic layers were dried over anhydrous sodium sulfate and then concentrated under reduced pressure. The resulting residue was applied to a silica gel column chromatography to obtain 0.20 g of 2-(2-ethylsulfonylthiophen-3-yl)-3-methyl-6-trifluoromethyl-3H-imidazo[4,5-b]pyridine (Compound of Present Invention (14)).

(Compound of Present Invention (14))

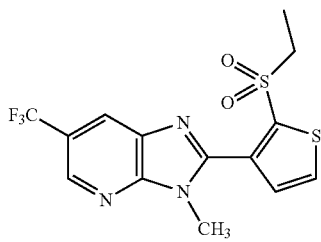 [SMILES: CCS(=O)(=O)c1sccc1-c1nc2cc(C(F)(F)F)cnc2n1C]

$^1$H-NMR (CDCl$_3$) δ: 8.74 (1H, d), 8.30 (1H, d), 7.89 (1H, d), 7.35 (1H, d), 3.82 (3H, s), 3.58 (2H, q), 1.38 (3H, t)

Production Example 15

A mixture of 0.22 g of 2-(3-chlorothiophen-2-yl)-3-methyl-6-trifluoromethyl-3H-imidazo[4,5-b]pyridine, 0.23 g of 2-(3-bromothiophen-2-yl)-3-methyl-6-trifluoromethyl-3H-imidazo[4,5-b]pyridine, 0.21 g of ethyl mercaptan sodium salt (80%) and 4 ml of DMF was stirred at 100° C. for 30 minutes. Water was poured into the reaction mixture, and the mixture was extracted with ethyl acetate. The combined organic layers were dried over anhydrous sodium sulfate and then concentrated under reduced pressure. The resulting residue was applied to a silica gel column chromatography to obtain 0.41 g of 2-(3-ethylthiothiophen-2-yl)-3-methyl-6-trifluoromethyl-3H-imidazo[4,5-b]pyridine (Compound of Present Invention (15)).
(Compound of Present Invention (15))

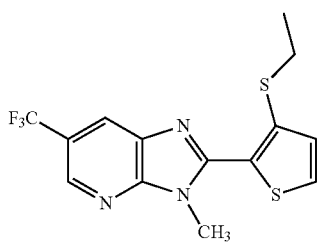 [SMILES: CCSc1ccsc1-c1nc2cc(C(F)(F)F)cnc2n1C]

$^1$H-NMR (CDCl$_3$) δ: 8.70 (1H, d), 8.32 (1H, d), 7.62 (1H, d), 7.20 (1H, d), 3.98 (3H, s), 2.90 (2H, q), 1.26 (3H, t)

Production Example 16

0.25 g of 3-chloroperoxybenzoic acid (69 to 75%) was added to a mixture of 0.25 g of 2-(3-ethylthiothiophen-2-yl)-3-methyl-6-trifluoromethyl-3H-imidazo[4,5-b]pyridine and 5 ml of chloroform, under ice cooling, then the mixture was heated to room temperature and stirred for 1 hour. A saturated aqueous sodium bicarbonate solution and a saturated aqueous sodium thiosulfate solution were poured to the reaction mixture, and the mixture was extracted twice with ethyl acetate. The combined organic layers were dried over anhydrous sodium sulfate and then concentrated under reduced pressure. The resulting residue was applied to a silica gel column chromatography to obtain 0.10 g of 2-(3-ethylsulfinylthiophen-2-yl)-3-methyl-6-trifluoromethyl-3H-imidazo[4,5-b]pyridine (Compound of Present Invention (16)) and 0.12 g of 2-(3-ethylsulfonylthiophen-2-yl)-3-methyl-6-trifluoromethyl-3H-imidazo[4,5-b]pyridine (Compound of Present Invention (17)).

(Compound of Present Invention (16))

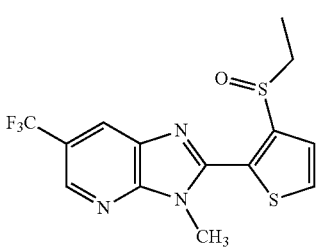 [SMILES: CCS(=O)c1ccsc1-c1nc2cc(C(F)(F)F)cnc2n1C]

$^1$H-NMR (CDCl$_3$) δ: 8.71 (1H, dd), 8.29 (1H, dd), 7.80 (1H, d), 7.74 (1H, d), 4.15 (3H, s), 3.47-3.36 (1H, m), 3.28-3.16 (1H, m), 1.41 (3H, t).

(Compound of Present Invention (17))

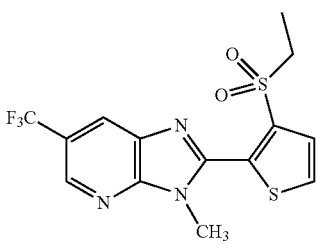 [SMILES: CCS(=O)(=O)c1ccsc1-c1nc2cc(C(F)(F)F)cnc2n1C]

$^1$H-NMR (CDCl$_3$) δ: 8.76 (1H, d), 8.31 (1H, d), 7.73 (1H, d), 7.61 (1H, d), 3.86 (3H, s), 3.31 (2H, q), 1.30 (3H, t)

Production Example 17

A mixture of 0.95 g of N$^2$-methyl-5-trifluoromethylpyridine-2,3-diamine, 0.94 g of 4-ethylthiothiophene-3-carboxylic acid, 1.15 g of EDCI hydrochloride, 0.06 g of HOBt and 8 ml of pyridine was stirred at 80° C. for 2 hours. A saturated aqueous sodium bicarbonate solution was poured into the cooled reaction mixture, and the mixture was extracted with ethyl acetate. The organic layer was washed with water, then dried over anhydrous sodium sulfate and concentrated under reduced pressure to obtain 4-ethylthiothiophene-3-carboxylic acid (2-methylamino-5-trifluoromethylpyridin-3-yl)-amide. A mixture of 4-ethylthiothiophene-3-carboxylic acid (2-methylamino-5-trifluoromethylpyridin-3-yl)-amide obtained above, 2.1 g of p-toluenesulfonic acid-hydrate and 10 mL of N-methylpyrrolidone was heated and stirred at 130° C. for 4 hours. Water was poured into the cooled reaction mixture, and the mixture was extracted with ethyl acetate. The organic layer was washed with water, then dried over anhydrous sodium sulfate and then concentrated under reduced pressure. The resulting residue was applied to a silica gel column chromatography to obtain 1.36 g of 2-(4-ethylthiothiophen-3-yl)-3-methyl-6-trifluoromethyl-3H-imidazo[4,5-b]pyridine (Compound of Present Invention (18)).

(Compound of Present Invention (18))

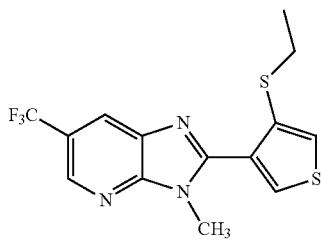 [SMILES: CCSc1cscc1-c1nc2cc(C(F)(F)F)cnc2n1C]

¹H-NMR (CDCl₃) δ: 8.71 (1H, d), 8.32 (1H, d), 7.74 (1H, d), 7.31 (1H, d), 3.89 (3H, s), 2.77 (2H, q), 1.23 (3H, t)

Production Example 18

1.02 g of 3-chloroperoxybenzoic acid (69 to 75%) was added to a mixture of 1.01 g of 2-(4-ethylthiothiophen-3-yl)-3-methyl-6-trifluoromethyl-3H-imidazo[4,5-b]pyridine and 10 ml of chloroform, under ice cooling, then the mixture was heated to room temperature and stirred for 3 hours. A saturated aqueous sodium bicarbonate solution and a saturated aqueous sodium thiosulfate solution were poured into the reaction mixture, and the mixture was extracted twice with ethyl acetate. The combined organic layers were dried over anhydrous sodium sulfate and then concentrated under reduced pressure. The resulting residue was applied to a silica gel column chromatography to obtain 0.51 g of 2-(4-ethyl-sulfinylthiophen-3-yl)-3-methyl-6-trifluoromethyl-3H-imidazo[4,5-b]pyridine (Compound of Present Invention (19)) and 0.52 g of 2-(4-ethylsulfonylthiophen-3-yl)-3-methyl-6-trifluoromethyl-3H-imidazo[4,5-b]pyridine (Compound of Present Invention (20)).

(Compound of Present Invention (19))

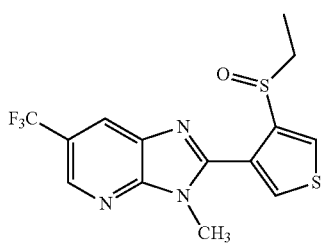 [SMILES: CCS(=O)c1cscc1-c1nc2cc(C(F)(F)F)cnc2n1C]

¹H-NMR (CDCl₃) δ: 8.71 (1H, d), 8.28 (1H, d), 8.18 (1H, d), 7.98 (1H, d), 4.11 (3H, s), 3.52-3.39 (1H, m), 3.16-3.04 (1H, m), 1.35 (3H, t).

(Compound of Present Invention (20))

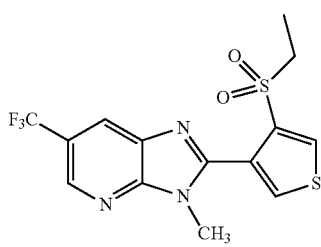 [SMILES: CCS(=O)(=O)c1cscc1-c1nc2cc(C(F)(F)F)cnc2n1C]

¹H-NMR (CDCl₃) δ: 8.74 (1H, s), 8.35 (1H, d), 8.29 (1H, s), 7.74 (1H, d), 3.82 (3H, s), 3.41 (2H, q), 1.29 (3H, q)

Production Example 19

A mixture of 0.84 g of 5-ethylthio-4-carboxylic acid (2-methylamino-5-trifluoromethylpyridin-3-yl)-amide, 0.88 g of p-toluenesulfonic acid-hydrate, 3 ml of DMF and 1 ml of toluene was heated and stirred at 150° C. for 2 hours. A saturated aqueous sodium bicarbonate solution was poured to the cooled reaction mixture, and the precipitated solid was filtered. The resulting solid was washed with water and n-hexane and then dried to obtain 0.77 g of 2-(5-ethylthiothiazol-4-yl)-3-methyl-6-trifluoromethyl-3H-imidazo[4,5-b]pyridine (Compound of Present Invention (21)).

(Compound of Present Invention (21))

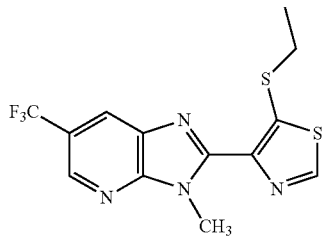 [SMILES: CCSc1scnc1-c1nc2cc(C(F)(F)F)cnc2n1C]

¹H-NMR (CDCl₃) δ: 8.80 (1H, s), 8.68 (1H, d), 8.36 (1H, d), 4.23 (3H, s), 3.13 (2H, q), 1.46 (3H, t)

Production Example 20

0.81 g of 3-chloroperoxybenzoic acid (purity of 65% or more) was added to a mixture of 0.56 g of 2-(5-ethylthiothiazol-4-yl)-3-methyl-6-trifluoromethyl-3H-imidazo[4,5-b]pyridine and 10 ml of chloroform, under ice cooling, and the mixture was stirred at room temperature for 5 hours and then allowed to stand overnight. A 10% aqueous sodium thiosulfate solution was poured into the reaction mixture, and the mixture was extracted with chloroform. The organic layer was washed with a saturated aqueous sodium bicarbonate solution and dried over anhydrous magnesium sulfate, then concentrated under reduced pressure to obtain 0.6 g of 2-(5-ethylsulfonylthiazol-4-yl)-3-methyl-6-trifluoromethyl-3H-imidazo[4,5-b]pyridine (Compound of Present Invention (22)).

(Compound of Present Invention (22))

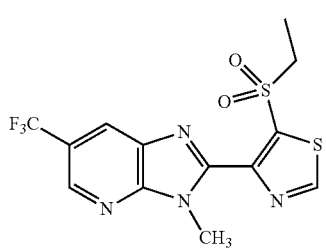 [SMILES: CCS(=O)(=O)c1scnc1-c1nc2cc(C(F)(F)F)cnc2n1C]

¹H-NMR (CDCl₃) δ: 9.15 (1H, s), 8.76 (1H, d), 8.35 (1H, d), 4.16 (2H, q), 4.11 (3H, s), 1.48 (3H, t)

Production Example 21

A solution of 0.49 g of 2-chloro-3-methyl-6-trifluoromethyl-3H-imidazo[4,5-b]pyridine in DMF (2 ml) was added to a mixture of 0.24 g of 2-ethylthio-1H-pyrrole, 0.11 g of sodium hydride (60% oil-based) and 3 ml of DMF, and the mixture was stirred at room temperature for 1.5 hours. Water was poured into the reaction mixture, and the mixture was extracted with ethyl acetate. The organic layer was washed with water, then dried over anhydrous magnesiums sulfate and concentrated under reduced pressure. The resulting residue was applied to a silica gel column chromatography to obtain 0.53 g of 2-(2-ethylthiopyrrol-1-yl)-3-methyl-6-trifluoromethyl-3H-imidazo[4,5-b]pyridine (Compound of Present Invention (23)).

(Compound of Present Invention (23))

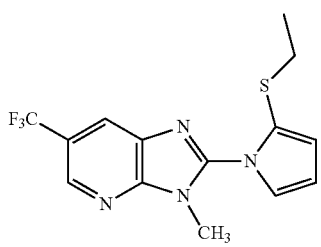 [SMILES: CCSc1cccn1-c1nc2cc(C(F)(F)F)cnc2n1C]

$^1$H-NMR (CDCl$_3$) δ: 8.75 (1H, d), 8.31 (1H, d), 7.09 (1H, dd), 6.64 (1H, dd), 6.44 (1H, t), 3.70 (3H, s), 2.53 (2H, q), 1.09 (3H, t)

Production Example 22

0.5 g of 3-chloroperoxybenzoic acid (purity of 65% or more) was added to a mixture of 0.32 g of 2-(2-ethylthiopyrrol-1-yl)-3-methyl-6-trifluoromethyl-3H-imidazo[4,5-b]pyridine and 8 ml of chloroform, under ice cooling, and the mixture was stirred at room temperature for 3 hours and then allowed to stand overnight at room temperature. A 10% aqueous sodium thiosulfate solution was poured to the reaction mixture, and the mixture was extracted with chloroform. The organic layer was washed with a saturated aqueous sodium bicarbonate solution and dried over anhydrous magnesium sulfate, then concentrated under reduced pressure. The resulting residue was applied to a silica gel column chromatography to obtain 0.33 g of 2-(2-ethylsulfonylpyrrol-1-yl)-3-methyl-6-trifluoromethyl-3H-imidazo[4,5-b]pyridine (Compound of Present Invention (24)).

(Compound of Present Invention (24))

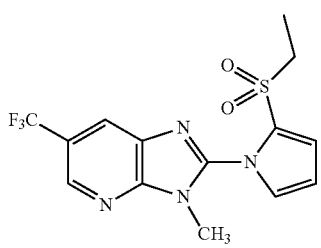 [SMILES: CCS(=O)(=O)c1cccn1-c1nc2cc(C(F)(F)F)cnc2n1C]

$^1$H-NMR (CDCl$_3$) δ: 8.77 (1H, s), 8.31 (1H, s), 7.20 (1H, d), 7.15 (1H, d), 6.58 (1H, t), 3.72 (3H, s), 3.33 (2H, q), 1.31 (3H, t)

Production Example 23

A mixture of 0.22 g of N$^2$-methyl-5-trifluoromethylpyridine-2,3-diamine, 0.26 g of 5-ethylthio-1-methyl-3-trifluoromethyl-1H-pyrazole-4-carboaldehyde, 0.18 g of sodium sulfite, 0.31 g of copper(II) chloride (anhydrous) and 2 ml of N,N-dimethylacetamide was stirred at 150° C. for 8 hours. Ethyl acetate and a saturated aqueous sodium bicarbonate solution were poured into the cooled reaction mixture, and the mixture was filtered. The aqueous layer of the filtrate was extracted with ethyl acetate and then combined with the organic layer of the filtrate, and the mixture was washed with water and dried over anhydrous magnesium sulfate. The mixture was concentrated under reduced pressure, then the resulting residue was applied to a silica gel column chromatography to obtain 0.34 g of 2-(5-ethylthio-1-methyl-3-trifluoromethyl-1H-pyrazol-4-yl)-3-methyl-6-trifluoromethyl-3H-imidazo[4,5-b]pyridine (Compound of Present Invention (25)).

(Compound of Present Invention (25))

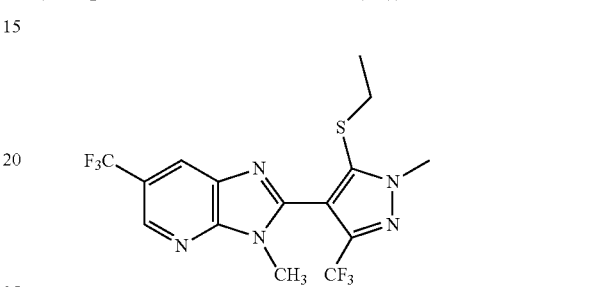

$^1$H-NMR (CDCl$_3$) δ: 8.74 (1H, d), 8.34 (1H, d), 4.13 (3H, s), 3.77 (3H, s), 2.73 (2H, q), 1.16 (3H, t)

Production Example 24

0.35 g of 3-chloroperoxybenzoic acid (purity of 65% or more) was added to a mixture of 0.24 g of 2-(5-ethylthio-1-methyl-3-trifluoromethyl-1H-pyrazol-4-yl)-3-methyl-6-trifluoromethyl-3H-imidazo[4,5-b]pyridine and 5 ml of chloroform, under ice cooling, and the mixture was stirred at room temperature for 6 hours. A 10% aqueous sodium thiosulfate solution was poured into the reaction mixture, and the mixture was extracted with chloroform. The organic layer was washed with a saturated aqueous sodium bicarbonate solution and dried over anhydrous magnesium sulfate, then concentrated under reduced pressure. The resulting residue was applied to a silica gel column chromatography to obtain 0.24 g of 2-(5-ethylsulfonyl-1-methyl-3-trifluoromethyl-1H-pyrazol-4-yl)-3-methyl-6-trifluoromethyl-3H-imidazo[4,5-b]pyridine (Compound of Present Invention (26)).

(Compound of Present Invention (26))

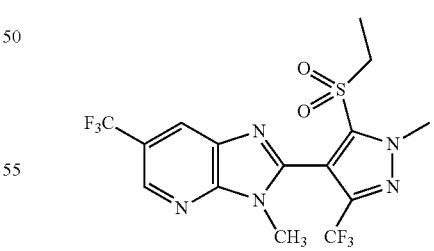

$^1$H-NMR (CDCl$_3$) δ: 8.76 (1H, d), 8.31 (1H, d), 4.37 (3H, s), 3.77 (3H, s), 3.57-3.44 (1H, m), 3.37-3.26 (1H, m), 1.38 (3H, t)

Production Example 25

A mixture of 0.24 g of 3-amino-5-(trifluoromethyl)pyridine-2-thiol, 0.27 g of 5-ethylthio-1-methyl-3-trifluoromethyl-1H-pyrazole-4-carboaldehyde, 0.19 g of sodium sulfite, 0.33 g of copper(II) chloride (anhydrous) and 2 ml of N,N-dimethylacetamide was stirred at 150° C. for 8 hours. Ethyl acetate and a saturated aqueous sodium bicarbonate solution were poured into the cooled reaction mixture, and the mixture was filtered. The aqueous layer of the filtrate was extracted with ethyl acetate and then combined with the organic layer of the filtrate, and the mixture was washed with water and dried over anhydrous magnesium sulfate. The mixture was concentrated under reduced pressure, then the resulting residue was applied to a silica gel column chromatography to obtain 0.21 g of 2-(5-ethylthio-1-methyl-3-trifluoromethyl-1H-pyrazol-4-yl)-6-trifluoromethylthiazolo[5,4-b]pyridine (Compound of Present Invention (27)).
(Compound of Present Invention (27))

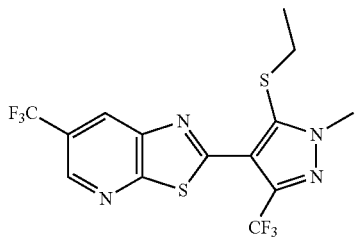 [SMILES: CCSc1c(-c2nc3cc(C(F)(F)F)cnc3s2)c(C(F)(F)F)nn1C]

$^1$H-NMR (CDCl$_3$) δ: 8.86 (1H, d), 8.56 (1H, d), 4.13 (3H, s), 2.90 (2H, q), 1.27 (3H, t).

Production Example 26

0.31 g of 3-chloroperoxybenzoic acid (purity of 65% or more) was added to a mixture of 0.21 g of 2-(5-ethylthio-1-methyl-3-trifluoromethyl-1H-pyrazol-4-yl)-6-trifluoromethylthiazolo[5,4-b]pyridine and 4 ml of chloroform, under ice cooling, and the mixture was stirred at room temperature for 6 hours. A 10% aqueous sodium thiosulfate solution was poured into the reaction mixture, and the mixture was extracted with chloroform. The organic layer was washed with a saturated aqueous sodium bicarbonate solution and dried over anhydrous magnesium sulfate, then concentrated under reduced pressure. The resulting residue was applied to a silica gel column chromatography to obtain 0.24 g of 2-(5-ethylsulfonyl-1-methyl-3-trifluoromethyl-1H-pyrazol-4-yl)-6-trifluoromethylthiazolo[5,4-b]pyridine (Compound of Present Invention (28)).
(Compound of Present Invention (28))

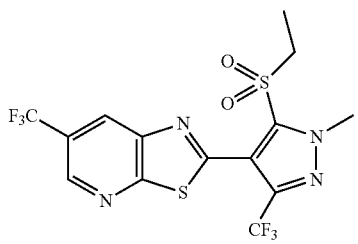 [SMILES: CCS(=O)(=O)c1c(-c2nc3cc(C(F)(F)F)cnc3s2)c(C(F)(F)F)nn1C]

$^1$H-NMR (CDCl$_3$) δ: 8.94 (1H, d), 8.55 (1H, d), 4.35 (3H, s), 3.58 (2H, q), 1.44 (3H, t)

Production Example 27

3.08 g of 3-chloroperoxybenzoic acid (purity of 65% or more) was added to a mixture of 2.44 g of 2-(3-ethylthiothiophen-2-yl)-5-(trifluoromethylthio)benzoxazole and 20 ml of chloroform, under ice cooling, and the mixture was stirred at room temperature for 1 hour. A 10% aqueous sodium thiosulfate solution was poured into the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 2.6 g of 2-(3-ethylsulfonylthiophen-2-yl)-5-(trifluoromethylthio)benzoxazole (Compound of Present Invention (29)).
(Compound of Present Invention (29))

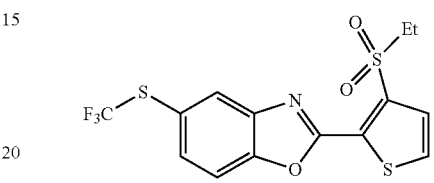

$^1$H-NMR (CDCl$_3$) δ: 8.16 (1H, d), 7.70-7.74 (2H, m), 7.63-7.67 (2H, m), 3.86 (2H, q), 1.41 (3H, t)

Production Example 28

0.31 g of sodium hydride (60%) was added to 20 ml of a solution of 2.76 g of 2-(3-bromothiophen-2-yl)-5-(trifluoromethylthio)benzoxazole and 0.6 ml of ethanethiol in NMP at 0° C., and the mixture was stirred at room temperature for 1 hour. Water was poured into the reaction mixture, and the mixture was extracted with ethyl acetate. The organic layer was washed with a 10% aqueous hydrochloric acid solution and a saturated aqueous salt solution and dried over anhydrous sodium sulfate, then concentrated under reduced pressure. The resulting residue was applied to a silica gel column chromatography to obtain 2.65 g of 2-(3-ethylthiothiophen-2-yl)-5-(trifluoromethylthio)benzoxazole (Compound of Present Invention (30)).
(Compound of Present Invention (30))

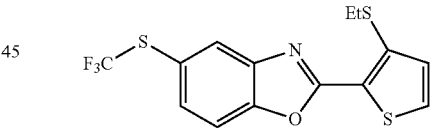

$^1$H-NMR (CDCl$_3$) δ: 8.12 (1H, d), 7.56-7.64 (3H, m), 7.12 (1H, d), 3.15 (2H, q), 1.46 (3H, t)

Production Example 29

1.3 g of 3-chloroperoxybenzoic acid (purity of 65% or more) was added to a mixture of 2.2 g of 2-(3-ethylsulfonylthiophen-2-yl)-5-(trifluoromethyl)benzoxazole and 20 ml of chloroform, under ice cooling, and the mixture was stirred at room temperature for 1 hour. A 10% aqueous sodium thiosulfate solution was poured into the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 0.7 g of 2-(3-ethylsulfonylthiophen-2-yl)-5-(trifluoromethylsulfinyl)benzoxazole (Compound of Present Invention (31)).

(Compound of Present Invention (31))

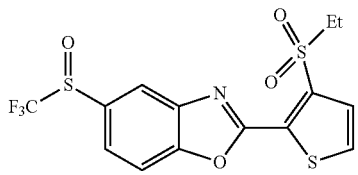 [SMILES: CCS(=O)(=O)c1ccsc1-c1nc2cc(S(=O)C(F)(F)F)ccc2o1]

¹H-NMR (CDCl₃) δ: 8.29 (1H, d), 7.83-7.90 (2H, m), 7.73 (1H, d), 7.68 (1H, d), 3.86 (2H, q), 1.42 (3H, t)

Production Example 30

A mixture of 1.4 g of 2-(3-ethylsulfonylthiophen-2-yl)-5-(trifluoromethylthio)benzoxazole, 0.12 g of sodium tungstate dehydrate and 12 ml of aqueous hydrogen peroxide (30%) was stirred at 80° C. for 5 hours. A 10% aqueous sodium thiosulfate solution was poured into the reaction mixture, and the mixture was extracted with ethyl acetate. The organic layer was washed with a saturated aqueous salt solution and dried over anhydrous sodium sulfate, then concentrated under reduced pressure. The resulting residue was applied into a silica gel column chromatography to obtain 0.4 g of 2-(3-ethylsulfonylthiophen-2-yl)-5-(trifluoromethylsulfonyl)benzoxazole (Compound of Present Invention (32)).
(Compound of Present Invention (32))

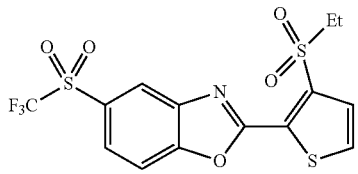 [SMILES: CCS(=O)(=O)c1ccsc1-c1nc2cc(S(=O)(=O)C(F)(F)F)ccc2o1]

¹H-NMR (CDCl₃) δ: 8.55 (1H, d), 8.13 (1H, d), 7.88 (1H, d), 7.75 (1H, d), 7.21 (1H, d), 3.85 (2H, q), 1.43 (3H, t)

Production Example 31

0.87 g of 3-chloroperoxybenzoic acid (purity of 65% or more) was added to a mixture of 0.6 g of 2-(3-ethylthiophen-2-yl)-5-(trifluoromethyl)benzoxazole and 6 ml of chloroform, under ice cooling, and the mixture was stirred at room temperature for 1 hour. A 10% aqueous thiosulfate solution was poured to the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 0.53 g of 2-(3-ethylsulfonylthiophen-2-yl)-5-(trifluoromethyl)benzoxazole (Compound of Present Invention (33)).
(Compound of Present Invention (33))

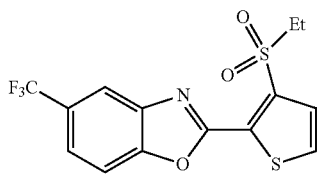 [SMILES: CCS(=O)(=O)c1ccsc1-c1nc2cc(C(F)(F)F)ccc2o1]

¹H-NMR (CDCl₃) δ: 8.12 (1H, d), 7.70-7.73 (3H, m), 7.65 (1H, d), 3.86 (2H, q), 1.41 (3H, t)

Production Example 32

0.57 g of 3-chloroperoxybenzoic acid (purity of 65% or more) was added to a mixture of 0.41 g of 2-(3-ethylthiothiophen-2-yl)-5-(trifluoromethyl)benzoxazole and 4 ml of chloroform, under ice cooling, and the mixture was stirred at room temperature for 1 hour. A 10% aqueous sodium thiosulfate solution was poured to the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 0.33 g of 2-(3-ethylsulfonylthiophen-2-yl)-5-(trifluoromethyl)benzothiazole (Compound of Present Invention (34)).
(Compound of Present Invention (34))

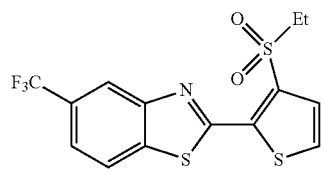 [SMILES: CCS(=O)(=O)c1ccsc1-c1nc2cc(C(F)(F)F)ccc2s1]

¹H-NMR (CDCl₃) δ: 8.37 (1H, d), 8.05 (1H, d), 7.69 (1H, d), 7.63 (1H, d), 7.59 (1H, d), 3.56 (2H, q), 1.37 (3H, t)

Production Example 33

0.06 g of sodium hydride (60%) was added to 5 ml of a solution of 0.53 g of 2-(3-bromothiophen-2-yl)-5-pentafluoroethylbenzoxazole and 0.1 ml of ethanethiol in NMP at 0° C., and the mixture was stirred at room temperature for 1 hour. Water was poured into the reaction mixture, and the mixture was extracted with ethyl acetate. The organic layer was washed with a 10% aqueous hydrochloric acid solution and a saturated aqueous salt solution, and dried over anhydrous sodium sulfate, then concentrated under reduced pressure. To a mixture of the residue and 5 ml of chloroform was added 0.66 g of 3-chloroperoxybenzoic acid (purity of 65% or more), under ice cooling, and the mixture was stirred at room temperature for 1 hour. A 10% aqueous sodium thiosulfate solution was poured into the reaction mixture, and the mixture was extracted with chloroform. The organic layer was washed with a saturated aqueous sodium bicarbonate solution and dried over anhydrous sodium sulfate, then concentrated under reduced pressure. The resulting residue was applied to a silica gel column chromatography to obtain 0.32 g of 2-(3-ethylsulfonylthiophen-2-yl)-5-pentafluoroethylbenzoxazole (Compound of Present Invention (35)).
(Compound of Present Invention (35))

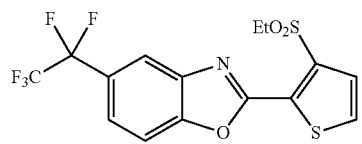

¹H-NMR (CDCl₃) δ: 8.10 (1H, d), 7.70-7.75 (2H, m), 7.64-7.69 (2H, m), 3.87 (2H, q), 1.41 (3H, t)

Production Example 34

0.11 g of sodium hydride (60%) was added to a solution of 0.65 g of 2-(3-bromothiophen-2-yl)-5-(trifluoromethyl)benzoxazole and 0.2 ml of ethanethiol in NMP 6 ml at 0° C., and the mixture was stirred at room temperature for 1 hour. Water was poured to the reaction mixture, and the mixture was extracted with ethyl acetate. The organic layer was washed with a 10% aqueous hydrochloric acid solution and a saturated aqueous salt solution and dried over anhydrous sodium sulfate, then concentrated under reduced pressure. The resulting residue was applied to a silica gel column chromatography to obtain 0.8 g of 2-(3-ethylthiothiophen-2-yl)-5-(trifluoromethyl)benzoxazole (Compound of Present Invention (36)).

(Compound of Present Invention (36))

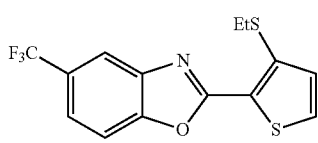

$^1$H-NMR (CDCl$_3$) δ: 8.08 (1H, d), 7.60-7.67 (3H, m), 7.12 (1H, d), 3.16 (2H, q), 1.46 (3H, t)

Production Example 35

0.11 g of sodium hydride (60%) was added to a solution of 0.65 g of 2-(3-bromothiophen-2-yl)-5-(trifluoromethyl)benzothiazole and 0.15 ml of ethanethiol in NMP 6 ml 0° C., and the mixture was stirred at room temperature for 1 hour. Water was poured into the reaction mixture, and the mixture was extracted with ethyl acetate. The organic layer was washed with a 10% aqueous hydrochloric acid solution and a saturated aqueous salt solution and dried over anhydrous sodium sulfate, then concentrated under reduced pressure. The resulting residue was applied to a silica gel column chromatography to obtain 0.61 g of 2-(3-ethylthiothiophen-2-yl)-5-(trifluoromethyl)benzothiazole (Compound of Present Invention (37)).

(Compound of Present Invention (37))

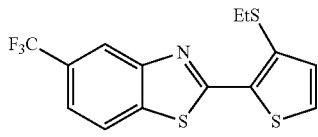

$^1$H-NMR (CDCl$_3$) δ: 8.31 (1H, d), 8.00 (1H, d), 7.60 (1H, dd), 7.52 (1H, d), 7.17 (1H, d), 3.03 (2H, q), 1.35 (3H, t)

Next, the reference production examples for the production of the production intermediate of the compound of the present invention will be shown.

Reference Production Example 1

A mixture of 0.50 g of N$^2$-methyl-5-trifluoromethylthiopyridine-2,3-diamine, 0.44 g of 3-chloro-thiophene-2-carboxylic acid, 0.51 g of EDCI hydrochloride, 30 mg of HOBt and 5 ml of pyridine was stirred at 90° C. for 10 hours. Water was poured into the cooled reaction mixture, and the deposited precipitate was filtered. The filtrate was applied to a silica gel column chromatography to obtain 0.7 g of 2-(3-chlorothiophen-2-yl)-3-methyl-6-trifluoromethylthio-3H-imidazo[4,5,b]pyridine.

2-(3-Chlorothiophen-2-yl)-3-methyl-6-trifluoromethylthio-3H-imidazo[4,5,b]pyridine

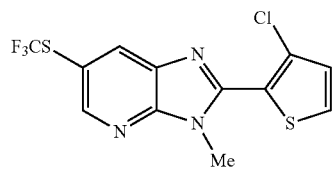

$^1$H-NMR (CDCl$_3$) δ: 8.68 (1H, d), 8.42 (1H, d), 7.61 (1H, d), 7.15 (1H, d), 3.96 (3H, s)

Reference Production Example 2

A mixture of 1.91 g of N$^2$-methyl-5-trifluoromethylpyridine-2,3-diamine, 2.07 g of 3-bromothiophene-2-carboxylic acid, 2.30 g of EDCI hydrochloride, 0.13 g of HOBt and 10 ml of pyridine was stirred at 80° C. for 2 hours. A saturated aqueous sodium bicarbonate solution was poured to the cooled reaction mixture, and the mixture was extracted with ethyl acetate. The organic layer was washed with water, then dried over anhydrous sodium sulfate and concentrated under reduced pressure to obtain 3 g of 2-bromothiophene-3-carboxylic acid (2-methylamino-5-trifluoromethylpyridin-3-yl)-amide.

2-Bromothiophene-3-carboxylic acid (2-methylamino-5-trifluoromethylpyridin-3-yl)-amide

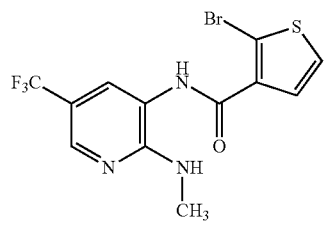 [SMILES: CNc1ncc(C(F)(F)F)cc1NC(=O)c1ccsc1Br]

$^1$H-NMR (CDCl$_3$) δ: 8.38 (1H, s), 7.88 (1H, brs), 7.71 (1H, s), 7.47 (1H, d), 7.34 (1H, d), 5.13 (1H, brs), 3.07 (3H, d)

Reference Production Example 3

A mixture of the 2-bromothiophene-3-carboxylic acid (2-methylamino-5-trifluoromethylpyridin-3-yl)-amide obtained above, 4.19 g of p-toluenesulfonic acid-hydrate and 20 mL of N-methylpyrrolidinone was heated and stirred at 130° C. for 3 hours. Water was poured into the cooled reaction mixture, and the crystal was filtered and dried to obtain 3.23 g of 2-(2-bromothiophen-3-yl)-3-methyl-6-trifluoromethyl-3H-imidazo[4,5-b]pyridine.

2-(2-Bromothiophene-3-yl)-3-methyl-6-trifluoromethyl-3H-imidazo[4,5-b]pyridine

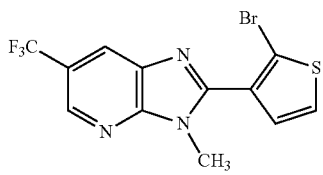 [SMILES: Cn1c(-c2ccsc2Br)nc2cc(C(F)(F)F)cnc21]

$^1$H-NMR (CDCl$_3$) δ: 8.72 (1H, d), 8.33 (1H, d), 7.49 (1H, d), 7.19 (1H, d), 3.91 (3H, s)

Reference Production Example 4

A mixture of 9.68 g of 3,4-dibromothiophene and 80 mL of diethylether was cooled to −70° C., 27 mL of n-butyl lithium (1.63 M hexane solvent) was added over 30 minutes, and the mixture was stirred at −70° C. for 30 minutes. To the mixture was added 5.86 g of diethyl disulfide at such a rate that the internal temperature is maintained at −60° C. or less, and the mixture was stirred at −70° C. for 2 hours. The reaction mixture was heated to −35° C. and then 100 mL of water was added. After heating to room temperature, a 2 N aqueous sodium hydroxide solution was added, and the mixture was extracted with ethyl acetate. The combined organic layers were dried over anhydrous sodium sulfate and then concentrated under reduced pressure. The resulting residue was applied to a silica gel column chromatography to obtain 3.27 g of 3-bromo-4-ethylthiothiophene.

3-Bromo-4-ethylthiothiophene

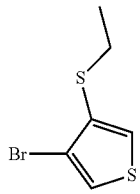

$^1$H-NMR (CDCl$_3$) δ: 7.33 (1H, d), 7.14 (1H, d), 2.89 (2H, q), 1.31 (3H, t)

Reference Production Example 5

A mixture of 3.27 g of 3-bromo-4-ethylthiothiophene and 30 mL of diethylether was cooled to −70° C., 98 mL of n-butyl lithium (1.63 M hexane solvent) was added over 30 minutes, and the mixture was stirred at −70° C. for 30 minutes. CO$_2$ gas was introduced to the mixture at such a rate that the internal temperature is maintained at −60° C. or less, and the mixture was stirred at −60° C. for 1 hour. The reaction mixture was heated to −20° C. and then 100 mL of water was added. After heating to room temperature, a saturated aqueous sodium bicarbonate solution was added, and the mixture was extracted with ethyl acetate. Hydrochloric acid was added to the resulting aqueous layer, and the precipitated crystal was obtained by filtration and dried to obtain 1.66 g of 4-ethylthiothiophene-3-carboxylic acid.

4-Ethylthiothiophene-3-carboxylic acid

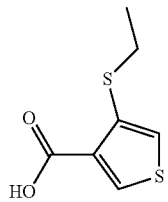

$^1$H-NMR (CDCl$_3$) δ: 8.34 (1H, d), 6.93 (1H, d), 2.94 (2H, q), 1.39 (3H, t)

Reference Production Example 6

0.56 g of ethyl mercaptan sodium salt (80%) was added to a mixture of 0.86 g of 5-chlorothiazole-4-carboxylic acid ethyl ester, 3 ml of DMF and 1 ml of THF, under ice cooling, and then the mixture was stirred at room temperature for 1 hour. Water was poured to the reaction mixture, and the mixture was extracted with ethyl acetate. The organic layer was washed with water, then dried over anhydrous magnesium sulfate and concentrated under reduced pressure. The resulting residue was applied to a silica gel column chromatography to obtain 0.71 g of 5-ethylsulfanylthiazole-4-carboxylic acid ethyl ester.

5-Ethylsulfanylthiazole-4-carboxylic acid ethyl ester

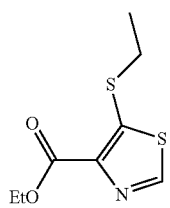

$^1$H-NMR (CDCl$_3$) δ: 8.61 (1H, s), 4.44 (2H, q), 3.06 (2H, q), 1.46 (3H, t), 1.43 (3H, t)

Reference Production Example 7

0.37 g of potassium hydroxide dissolved in 1 ml of an aqueous solution was added to a mixture of 0.71 g of 5-ethylthiothiazole-4-carboxylic acid ethyl ester and 5 ml of methanol, under ice cooling, then the mixture was stirred at room temperature for 2 hours. 1 N hydrochloric acid was poured into the reaction mixture under ice cooling, and the precipitated solid was filtered. The resulting solid was washed with 0.1 N hydrochloric acid and n-hexane, then dried to obtain 0.59 g of 5-ethylthiothiazole-4-carboxylic acid hydrochloride.

5-Ethylthiothiazole-4-carboxylic acid hydrochloride

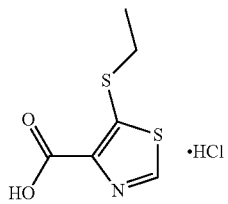

¹H-NMR (DMSO-D₆) δ: 8.84 (1H, s), 2.99 (2H, q), 1.30 (3H, t)

Reference Production Example 8

A mixture of 0.5 g of N²-methyl-5-trifluoromethylpyridine-2,3-diamine, 0.59 g of 5-ethylthiothiazole-4-carboxylic acid hydrochloride, 0.75 g of EDCI hydrochloride, 0.04 g of HOBt and 4 ml of pyridine was stirred at room temperature for 2 hours and then stirred at 60° C. for 30 minutes. Water was poured into the cooled reaction mixture, and the precipitated solid was filtered. The resulting solid was washed with water and n-hexane and then dried to obtain 0.84 g of 5-ethylthio-4-carboxylic acid (2-methylamino-5-trifluoromethylpyridin-3-yl)-amide.

5-Ethylthio-4-carboxylic acid (2-methylamino-5-trifluoromethylpyridin-3-yl)-amide

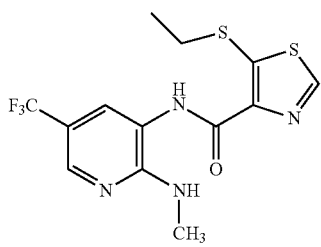 [SMILES: CCSc1scnc1C(=O)Nc1cc(C(F)(F)F)cnc1NC]

¹H-NMR (CDCl₃) δ: 8.67 (1H, brs), 8.59 (1H, d), 8.33 (1H, s), 7.86 (1H, d), 5.15 (1H, brs), 3.11-3.04 (5H, m), 1.48 (3H, t)

Reference Production Example 9

A mixture of 1.91 g of N²-methyl-5-trifluoromethylpyridine-2,3-diamine, 3.24 g of carbodiimidazole and 10 ml of acetonitrile was stirred at 50° C. for 1 hour and at 80° C. for 2 hours. Water was poured into the cooled reaction mixture, and the precipitated crystal was obtained by filtration and dried to obtain 2.0 g of 3-methyl-6-trifluoromethyl-1,3-dihydro-imidazo[4,5-b]pyridin-2-one.

3-Methyl-6-trifluoromethyl-1,3-dihydro-imidazo[4,5-b]pyridin-2-one

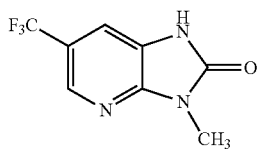

¹H-NMR (CDCl₃) δ: 10.24 (1H, s), 8.39 (1H, s), 7.53 (1H, s), 3.56 (3H, s)

Reference Production Example 10

A mixture of 1.09 g of 3-methyl-6-trifluoromethyl-1,3-dihydro-imidazo[4,5-b]pyridin-2-one, one drop of dimethylformamide and 10 g of phosphorus oxychloride was stirred at 100° C. for 3 hours. The cooled reaction mixture was poured to a saturated aqueous sodium bicarbonate solution, and the mixture was extracted twice with ethyl acetate. The combined organic layers were dried over anhydrous sodium sulfate and then concentrated under reduced pressure. The resulting residue was applied to a silica gel column chromatography to obtain 0.61 g of 2-chloro-3-methyl-6-trifluoromethyl-3H-imidazo[4,5-b]pyridine.

2-Chloro-3-methyl-6-trifluoromethyl-3H-imidazo[4,5-b]pyridine

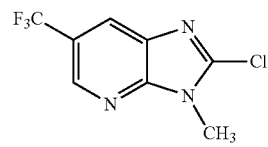

¹H-NMR (CDCl₃) δ: 8.66 (1H, d), 8.19 (1H, d), 3.92 (3H, s)

Reference Production Example 11

One drop of N,N-dimethylformamide and 18 ml of thionyl chloride were added to 92 ml of a solution of 1.66 g of 3-bromo-2-thiophenecarboxylic acid in toluene. After stirring the mixture at 100° C. for 3 hours, the reaction solvent was concentrated under reduced pressure. This was added to 17 ml of a solution of 1.67 g of 2-amino-4-trifluoromethylthiophenol in THF at room temperature. After stirring the mixture for 1 hour, ethyl acetate was added, and the mixture was washed with a saturated aqueous sodium bicarbonate solution, dried over anhydrous sodium sulfate and then concentrated under reduced pressure. This was added to 10 ml of a solution of 3.16 g of triphenylphosphine in THF, subsequently, 3 g of bis(2-methoxyethyl) azodicarboxylate was added, and the mixture was stirred at 50° C. for 4 hours. After cooling, a saturated aqueous ammonium chloride solution was poured to the reaction mixture, and extracted with ethyl acetate. The organic layer was washed with a saturated aqueous salt solution and dried over anhydrous sodium sulfate, then concentrated under reduced pressure. The resulting residue was applied to a silica gel column chromatography to obtain 2.76 g of 2-(3-bromothiophen-2-yl)-5-(trifluoromethylthio)benzoxazole.

2-(3-Bromothiophen-2-yl)-5-(trifluoromethylthio)benzoxazole

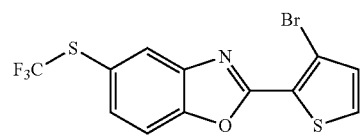 [SMILES: FC(F)(F)Sc1ccc2oc(-c3sccc3Br)nc2c1]

¹H-NMR (CDCl₃) δ: 8.13 (s, 1H), 7.62-7.71 (s, 2H), 7.54 (d, 1H), 7.19 (d, 1H)

Reference Production Example 12

One drop of N,N-dimethylformamide and 7 ml of thionyl chloride were added to 35 ml of a solution of 0.62 g of 3-bromo-2-thiophenecarboxylic acid in toluene. After stirring the mixture at 100° C. for 3 hours, the reaction solvent was concentrated under reduced pressure. The residue was added to 5 ml of a solution of 0.53 g of 2-amino-4-trifluoromethylthiophenol in THF at room temperature. After stirring the mixture for 1 hour, ethyl acetate was added, and the mixture was washed with a saturated aqueous sodium bicarbonate solution, dried over anhydrous sodium sulfate and then concentrated under reduced pressure. The residue was added to 10 ml of a solution of 1.1 g of triphenylphosphine in THF, subsequently, 1.01 g of bis(2-methoxyethyl)azodicarboxylate was added, and the mixture was stirred at 50° C. for 4 hours. After cooling, a saturated aqueous ammonium chloride solution was poured to the reaction mixture, and the mixture was extracted with ethyl acetate. The organic layer was washed with a saturated aqueous salt solution and dried over anhydrous sodium sulfate, then concentrated under reduced pressure. The resulting residue was applied to a silica gel column chromatography to obtain 0.86 g of 2-(3-bromothiophen-2-yl)-5-(trifluoromethyl)benzoxazole.

2-(3-Bromothiophen-2-yl)-5-(trifluoromethyl)benzoxazole

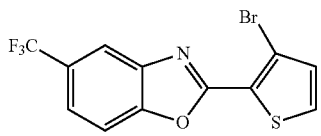

$^1$H-NMR (CDCl$_3$) δ: 8.08 (s, 1H), 7.64-7.72 (s, 2H), 7.54 (d, 1H), 7.20 (d, 1H)

Reference Production Example 13

One drop of N,N-dimethylformamide and 7 ml of thionyl chloride were added to 35 ml of a solution of 0.62 g of 3-bromo-2-thiophenecarboxylic acid in toluene. After stirring the mixture at 100° C. for 3 hours, the reaction solvent was concentrated under reduced pressure. The residue was added to 6 ml of a solution of 0.69 g of 2-amino-4-trifluoromethylbenzenethiol chloride in pyridine at room temperature. After stirring the mixture at 80° C. for 5 hours, water was poured, a 10% aqueous hydrochloric acid solution was added, and the mixture was extracted with ethyl acetate. The organic layer was washed with a saturated aqueous salt solution, dried over anhydrous sodium sulfate and then concentrated under reduced pressure. The resulting residue was applied to a silica gel column chromatography to obtain 0.65 g of 2-(3-bromothiophen-2-yl)-5-(trifluoromethyl)benzothiazole.

2-(3-Bromothiophen-2-yl)-5-(trifluoromethyl)benzothiazole

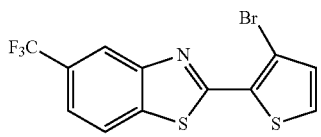 [SMILES: FC(F)(F)c1ccc2sc(-c3sccc3Br)nc2c1]

$^1$H-NMR (CDCl$_3$) δ: 8.34 (s, 1H), 8.04 (d, 1H), 7.64 (d, 1H), 7.51 (d, 1H), 7.17 (d, 1H)

Reference Production Example 14

One drop of N,N-dimethylformamide and 3.5 ml of thionyl chloride were added to 17 ml of a solution of 0.31 g of 3-bromo-2-thiophenecarboxylic acid in toluene. After stirring the mixture at 100° C. for 3 hours, the reaction solvent was concentrated under reduced pressure. The residue was added to 4 ml of a solution of 0.33 g of 2-amino-4-pentafluoroethylthiophenol in THF at room temperature. After stirring the mixture for 1 hour, ethyl acetate was added, and the mixture was washed with a saturated aqueous sodium bicarbonate solution, dried over anhydrous sodium sulfate and then concentrated under reduced pressure. The residue was added to 10 ml of a solution of 0.57 g of triphenylphosphine in THF, subsequently, 0.54 g of bis(2-methoxyethyl)azodicarboxylate was added, and the mixture was stirred at 50° C. for 4 hours. After cooling, a saturated aqueous ammonium chloride solution was poured into the reaction mixture, and the mixture was extracted with ethyl acetate. The organic layer was washed with a saturated aqueous salt solution and dried over anhydrous sodium sulfate, then concentrated under reduced pressure. The resulting residue was applied to a silica gel column chromatography to obtain 0.53 g of 2-(3-bromothiophen-2-yl)-5-pentafluoroethylbenzoxazole.

2-(3-Bromothiophen-2-yl)-5-pentafluoroethylbenzoxazole

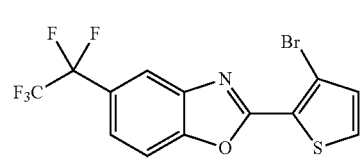 [SMILES: FC(F)(F)C(F)(F)c1ccc2oc(-c3sccc3Br)nc2c1]

$^1$H-NMR (CDCl$_3$) δ: 8.09 (s, 1H), 7.64-7.72 (s, 2H), 7.55 (d, 1H), 7.20 (d, 1H)

Next, formulation examples of the compound of the present invention are shown. The part means part by weight.

Formulation Example 1

10 parts of any one of Compounds of Present Invention 1 to 37 is dissolved in a mixture of 35 parts of xylene and 35 parts of N,N-dimethylformamide, 14 parts of polyoxyethylenestyrylphenyl ether and 6 parts of calcium dodecylbenzenesulfonate are added thereto. The mixture is mixed to obtain each emulsifiable concentrate.

Formulation Example 2

4 parts of sodium lauryl sulfate, 2 parts of calcium lignosulfonate, 20 parts of synthetic hydrous silicon oxide fine powder and 54 parts of diatomaceous earth are mixed, and 20 parts of any one of Compounds of Present Invention 1 to 37 is further added thereto. The mixture is mixed to obtain each wettable powder.

Formulation Example 3

1 part of synthetic hydrous silicon oxide fine powder, 2 parts of calcium lignosulfonate, 30 parts of bentonite and 65 parts of kaolin clay are added to 2 parts of any one of Compounds of Present Invention 1 to 37. Subsequently, an appropriate amount of water is added to this mixture, and the mixture is further stirred, granulated with a granulator, and forced-air dried to obtain each granule.

Formulation Example 4

1 part of any one of Compounds of Present Invention 1 to 37 is dissolved in an appropriate amount of acetone, and 5 parts of synthetic hydrous silicon oxide fine powder, 0.3 parts of PAP and 93.7 parts of Fubasami clay are added thereto. The mixture is sufficiently stirred and mixed to evaporate acetone to obtain each dust formulation.

Formulation Example 5

35 parts of a mixture of polyoxyethylene alkyl ether sulfate ammonium salt and white carbon (weight ratio 1:1), 10 parts of any one of Compounds of Present Invention 1 to 37 and 55 parts of water are mixed, and finely pulverized by wet grinding method to obtain each flowable.

Formulation Example 6

0.1 part of any one of Compounds of Present Invention 1 to 37 is dissolved in 5 parts of xylene and 5 parts of trichloroethane, and the mixture is mixed with 89.9 parts of deodorized kerosene to obtain each oil solution.

Formulation Example 7

10 mg of any one of Compounds of Present Invention 1 to 37 is dissolved in 0.5 ml of acetone, and this solution is applied to 5 g of solid feed powder for animal (solid feed powder for breeding CE-2, product of CLEA Japan, Inc.), and the mixture is uniformly mixed. Subsequently, acetone is evaporated to dryness to obtain each poisonous bait.

Formulation Example 8

0.1 part of any one of Compounds of Present Invention 1 to 37 and 49.9 parts of Neothiozol (Chuo Kasei Co., Ltd.) are filled into an aerosol container, and an aerosol valve is attached, then the container is filled with 25 parts of dimethyl ether and 25 parts of LPG and shaken, and an actuator is attached to obtain an oil-based aerosol.

Formulation Example 9

0.6 parts of any one of Compounds of Present Invention 1 to 37, 0.01 part of BHT (2,6-di-tert-butyl-4-methylphenol), 5 parts of xylene, 3.39 parts of deodorized kerosene and 1 part of emulsifier {RHEODOL MO60 (product name of Kao Corporation)} are mixed and dissolved, and the resulting solution and 50 parts of distilled water are filled into an aerosol container. A valve is attached to the container, and 40 parts of a propellant (LPG) is filled under pressure through the valve to obtain an aqueous aerosol.

Formulation Example 10

0.1 g of any one of Compounds of Present Invention 1 to 37 is dissolved in 2 ml of propylene glycol, and the solution is impregnated in a porous ceramic plate with a size of 4.0 cm×4.0 cm and 1.2 cm in thickness to obtain a heating type smoking agent.

Formulation Example 11

5 parts of any one of Compounds of Present Invention 1 to 37 and 95 parts of an ethylene-methyl methacrylate copolymer (a ratio of methyl methacrylate in the copolymer: 10% by weight, Acryft WD301, manufactured by SUMITOMO CHEMICAL Co., Ltd.) are melt-kneaded with a closed pressurizing kneader (manufactured by Moriyama Works), and the resulting kneaded matter is extruded from a molded matter through a molding die to obtain a rod-shaped molded body with a size of 15 cm in length and 3 mm in diameter.

Formulation Example 12

5 parts of any one of Compounds of Present Invention 1 to 37 and 95 parts of a soft vinyl chloride resin are melt-kneaded with a closed pressurizing kneader (manufactured by Moriyama Works), and the resulting kneaded matter is extruded from a molded matter through a molding die to obtain a rod-shaped molded body with a size of 15 cm in length and 3 mm in diameter.

Formulation Example 13

100 mg of any one of Compounds of Present Invention 1 to 37, 68.75 mg of lactose, 237.5 mg of corn starch, 43.75 mg of microcrystalline cellulose, 18.75 mg of polyvinylpyrrolidone, 28.75 mg of sodium carboxymethyl starch and 2.5 mg of magnesium stearate are mixed, and the resulting mixture was compressed to an appropriate size to obtain a tablet.

Formulation Example 14

25 mg of any one of Compounds of Present Invention 1 to 37, 60 mg of lactose, 25 mg of corn starch, 6 mg of carmellose calcium and an appropriate amount of 5% hydroxypropyl methylcellulose, and the resulting mixture is filled into a hard shell gelatin capsule or a hydroxypropyl methylcellulose capsule to obtain an encapsulated formulation.

Formulation Example 15

Distilled water is added to 1000 mg of any one of Compounds of Present Invention 1 to 37, 500 mg of fumaric acid, 2000 mg of sodium chloride, 150 mg of methylparaben, 50 mg of propylparaben, 25000 mg of granulated sugar, 13000 mg of sorbitol (70% solution), 100 mg of Veegum K (Vanderbilt Co.), 35 mg of flavor and 500 mg of colorant, such that the final volume is 100 ml, and the mixture is mixed to obtain a suspension for oral administration.

Formulation Example 16 parts of any one of Compounds of Present Invention 1 to 37, 5 parts of polysorbate 85 and 3 parts of benzyl alcohol are dissolved in 30 parts of propylene glycol, and a phosphate buffer is added to this solution so as to have a pH of 6.0 to 6.5, then water is added until the total amount is 100 parts to obtain a liquid formulation for oral administration.

Formulation Example 17

5 parts of aluminum distearate is dispersed in 57 parts of fractionated palm oil and 3 parts of polysorbate 85 by heating. 25 parts of saccharin is dispersed in an oily vehicle obtained by cooling this dispersion to room temperature. Further, 10 parts of any one of Compounds of Present Invention 1 to 378 is added thereto to obtain a paste formulation for oral administration.

Formulation Example 18

5% by weight of any one of Compounds of Present Invention 1 to 37 and 95% by weight of limestone filler are mixed, and a granule for oral administration is obtained using wet granulation method.

Formulation Example 19

5 parts of any one of Compounds of Present Invention 1 to 37 is dissolved in 80 parts of diethylene glycol monoethyl ether, and 15 parts of propylene carbonate is mixed therewith to obtain a spot-on solution.

Formulation Example 20

10 parts of any one of Compounds of Present Invention 1 to 37 is dissolved in 70 parts of diethylene glycol monoethyl ether, and 20 parts of 2-octyl dodecanol is mixed therewith to obtain a pour-on solution.

Formulation Example 21

60 parts of NIKKOL TEALS-42 (Nikko Chemicals Co., Ltd., 42% aqueous solution of triethanolamine lauryl sulfate) and 20 parts of propylene glycol are added to 0.5 parts of any one of Compounds of Present Invention 1 to 37, and the mixture is sufficiently stirred and mixed until it becomes a uniform solution, then 19.5 parts of water is added and further sufficiently stirred and mixed to obtain a shampoo agent as a uniform solution.

Formulation Example 22

0.15 parts of any one of Compounds of Present Invention 1 to 37, 95 parts of an animal feed and 4.85 parts of a mixture of secondary calcium phosphate, diatomaceous earth, Aerosil and carbonate (or chalk) are sufficiently stirred and mixed to obtain a feed premix for animal.

Formulation Example 23

7.2 g of any one of Compounds of Present Invention 1 to 37 and 92.8 g of VOSCO S-55 (manufactured by Maruishi Pharmaceutical Co., Ltd.) are dissolved and mixed at 100° C., poured into a suppository mold, and cooled and solidified to obtain a suppository.

Next, the pest control effect of the compound of the present invention is shown as test examples.

Test Example 1

Each of the formulations of Compounds of Present Invention 2 to 4, 6, 8 to 10, 13, 15 to 18, 21 to 24 obtained in Formulation Example 5 was diluted with water so as to have a concentration of the active ingredient of 500 ppm to prepare a test drug solution.

On the other hand, on a cucumber seedling (the first true leaf stage) planted in a plastic cup was inoculated with about 30 *Aphis gossypii*, and leaving it for a day. 20 ml of the test drug solution was sprayed on the seedling.

Six days after spraying, the number of the surviving *Aphis gossypii* parasitized on the leaves of the cucumber was examined, and the control value was calculated according to the following equation:

$$\text{Controlling value}(\%) = \{1-(Cb \times Tai)/(Cai \times Tb)\} \times 100$$

wherein the symbols represent as follows:
Cb: the number of insects in a non-treated section before treatment
Cai: the number of insects in a non-treated section on observation
Tb: the number of insects in a treated section before treatment
Tai: the number of insects in a treated section on observation
wherein the non-treated section refers to a section where the test drug solution prepared by diluting the formulation not containing the compound of the present invention as in Formulation Example 5 with the same amount of water as in the treated section was sprayed.

As a result, in the treated section using each test drug solution of Compounds of Present Invention 2 to 4, 6, 8 to 10, 13, 15 to 18, 21 to 24, the control value was 90% or more.

Test Example 2

Each of the formulations of Compounds of Present Invention 6, 17 and 18 as obtained in Formulation Example 5 was diluted with water, so as to have a concentration of the active ingredient of 500 ppm, to prepare a test drug solution.

On the other hand, a cucumber seedling (the second true leaf stage) planted in a plastic cup was drenched at its foot with 5 ml of the test drug solution, and kept in a greenhouse at 25° C. for 7 days. On the cucumber leaf surface was inoculated about 30 *Aphis gossypii* (whole stage), and further kept in the greenhouse for 6 days, then the number of insects of living *Aphis gossypii* parasitized on the leaves of the cucumber was examined, and the control value was calculated according to the following equation:

$$\text{Controlling value }(\%) = \{1-(Cb \times Tai)/(Cai \times Tb)\} \times 100$$

wherein the symbols represent as follows:
Cb: the number of insects in a non-treated section before treatment
Cai: the number of insects in a non-treated section on observation
Tb: the number of insects in a treated section before treatment
Tai: the number of insects in a treated section on observation
wherein the non-treated section refers to a section where the test drug solution prepared by diluting the formulation not containing the compound of the present invention as in Formulation Example 5 with the same amount of water as in the treated section was used.

As a result, in the treated section using each test drug solution of Compounds of Present Invention 6, 17 and 18, the control value was 90% or more.

Test Example 3

Each of the formulations of Compounds of Present Invention 5, 7, 13 and 22 as obtained in Formulation Example 5 was diluted with water, so as to have a concentration of the active ingredient of 500 ppm, to prepare a test drug solution.

A rice seedling in the second leaf stage planted in a polyethylene cup was sprayed with 10 ml of each test drug solution. After air-drying, 20 third-fourth instar larvae of *Nilaparvata lugens* were released, and kept in the greenhouse at 25° C. After 6 days, the number of *Nilaparvata lugens* parasitized on the rice was examined, and the control value was calculated according to the following equation:

$$\text{Controlling value }(\%) = \{1-(Cb \times Tai)/(Cai \times Tb)\} \times 100$$

wherein the symbols represent as follows:

Cb: the number of insects in a non-treated section before treatment

Cai: the number of insects in a non-treated section on observation

Tb: the number of insects in a treated section before treatment

Tai: the number of insects in a treated section on observation wherein the non-treated section refers to a section where the test drug solution prepared by diluting the formulation not containing the compound of the present invention as in Formulation Example 5 with the same amount of water as in the treated section was used.

As a result, in the treated section using each test drug solution of Compounds of Present Invention 5, 7, 13 and 22, the control value was 90% or more.

Test Example 4

Each of the formulations of Compounds of Present Invention 5, 8, 10 and 22 as obtained in Formulation Example 5 was diluted with water, so as to have a concentration of the active ingredient of 500 ppm, to prepare a test drug solution.

On the other hand, a rice seedling (2 weeks after sowing, the second leaf stage) planted in a plastic cup was drenched at its foot with 5 ml of each test drug solution, and kept in a greenhouse of 25° C. for 7 days. Twenty third-fourth instar larvae of *Nilaparvata lugens* were released, and further kept in the greenhouse for 6 days, then the number of insects of living *Nilaparvata lugens* parasitized on the rice was examined, and the control value was calculated according to the following equation:

Controlling value (%)={1−(Cb×Tai)/(Cai×Tb)}×100 wherein the symbols represent as follows:

Cb: the number of insects in a non-treated section before treatment

Cai: the number of insects in a non-treated section on observation

Tb: the number of insects in a treated section before treatment

Tai: the number of insects in a treated section on observation wherein the non-treated section refers to a section where the test drug solution prepared by diluting the formulation not containing the compound of the present invention as in Formulation Example 5 with the same amount of water as in the treated section was used.

As a result, in the treated section using each test drug solution of Compounds of Present Invention 5, 8, 10 and 22, the control value was 90% or more.

Test Example 5

Each of the formulations of Compounds of Present Invention 5 and 8 as obtained in Formulation Example 5 was diluted with water, so as to have a concentration of the active ingredient of 500 ppm, to prepare a test drug solution.

On the other hand, *Bemisia tabaci* adult was released on a tomato seedling (the third true leaf stage) planted in a polyethylene cup, and made to lay eggs for about 72 hours. The tomato seedling was kept in a greenhouse for 8 days, and when instar larvae hatched from the eggs, the above test drug solution was sprayed in the amount of 20 ml/cup, and the cup was kept in a greenhouse at 25° C. After 7 days, the number of surviving instar larvae on the tomato leaves was examined, and the control value was calculated according to the following equation:

Controlling value (%)={1−(Cb×Tai)/(Cai×Tb)}×100 wherein the symbols represent as follows:

Cb: the number of insects in a non-treated section before treatment

Cai: the number of insects in a non-treated section on observation

Tb: the number of insects in a treated section before treatment

Tai: the number of insects in a treated section at the time of observation wherein the non-treated section refers to a section where the test drug solution prepared by diluting the formulation without the compound of the present invention as in Formulation Example 5 with the same amount of water as in the treated section was used.

As a result, in the treated section using each test drug solution of Compounds of Present Invention 5 and 8, the control value was 90% or more.

Test Example 6

Each of the formulations of Compounds of Present Invention 1, 4 to 10, 14, 17 and 21 to 24 as obtained in Formulation Example 5 was diluted with water, so as to have a concentration of the active ingredient of 500 ppm, to prepare a test drug solution.

On the other hand, cabbage at the third leaf stage planted in a polyethylene cup was sprayed with 20 mL/cup of the test drug solution. After the drug solution was dried, the foliage part was cut off, and then placed in a 50 mL volume cup. Five second instar larvae of *Plutella xylostella* were released into the cup, and the cup was sealed with a lid. The cup was kept at 25° C., and after 5 days, the number of living insects was counted. The death rate was calculated according to the following equation:

Death rate (%)=(Number of dead insects/Number of tested insects)×100

As a result, in the treated section using each test drug solution of Compounds of Present Invention 1, 4 to 10, 14, 17 and 21 to 24, the death rate was 80% or more.

Test Example 7

Each of the formulations of Compounds of Present Invention 4 to 10, 14, 17 and 22 to 24 as obtained in Formulation Example 5 was diluted with water, so as to have a concentration of the active ingredient of 500 ppm, to prepare a test spray solution.

On the other hand, an apple tree was planted in a plastic cup, and grown until the seventh-eighth true leaf was spread. The apple tree was sprayed with 20 mL/cup of the test drug solution. After the drug solution was dried, 60 first-instar *Adoxophyes orana fasciata* were released, and the cup was covered with a plastic cup upside-down in which the bottom was cut off and a filter paper was put thereon. After 7 days, the number of living insects was counted, and the death rate was calculated according to the following equation:

Death rate (%)=(Number of dead insects/Number of tested insects)×100

As a result, in the treated section using each test drug solution of Compounds of Present Invention 4 to 10, 14, 17 and 22 to 24, the death rate was 90% or more.

Test Example 8

Each of the formulations of Compounds of Present Invention as obtained in Formulation Example 5 is diluted with water, so as to have a concentration of the active ingredient of 500 ppm, to prepare a test drug solution.

A filter paper having a diameter of 5.5 cm is spread on the bottom of a polyethylene cup having the same diameter, 0.7 ml of the test drug solution is added dropwise onto the filter paper, and 30 mg of sucrose is uniformly placed as bait. Into the polyethylene cup are released 10 female imagoes of *Musca domestica*, and the cup is sealed with a lid. After 24 hours, the life and death of *Musca domestica* is examined, and the death rate is calculated.

Test Example 9

Each of the formulations of Compounds of Present Invention as obtained in Formulation Example 5 is diluted with water, so as to have a concentration of the active ingredient of 500 ppm, to prepare a test drug solution.

A filter paper having a diameter of 5.5 cm is spread on the bottom of a polyethylene cup having the same diameter, 0.7 ml of the test drug solution is added dropwise onto the filter paper, and 30 mg of sucrose is uniformly placed as bait. Into the polyethylene cup are released 2 male imagoes of *Blattalla germanica*, and the cup is sealed with a lid. After 6 days, the life and death of *Blattalla germanica* is examined, and the death rate is calculated.

Test Example 10

Each of the formulations of Compounds of Present Invention 13 and 21 as obtained in Formulation Example 5 was diluted with water, so as to have a concentration of the active ingredient of 500 ppm, to prepare a test drug solution.

0.7 ml of the test drug solution was added to 100 ml of ion-exchanged water (active ingredient concentration: 3.5 ppm). Twenty last-instar larvae of *Culex pipiens pallens* were released into the solution. One day later, the life and death of the *Culex pipiens pallens* was examined, and the death rate of the pest was calculated.

As a result, in the treatment with Compounds of Present Invention 13 and 21, the death rate was 91% or more.

Test Example 11

2 mg of each of Compounds of Present Invention 26 and 28 was weighed in a screw tube (Maruemu No. 5; 27×55 mm), and 0.2 mL of acetone was added thereto and sealed with a cap to dissolve the compound. The screw tube was rotated and inverted to uniformity coat the drug solution onto the whole inner wall of the tube. After removing the cap, the solution was air-dried for about 2 hours, then non-blood-sucking nymphal ticks, *Haemaphysalis longicornis* (5 ticks/group) were released, and the tube was sealed with the cap. After 2 days, the number of dead tick was examined, and the death rate was calculated according to the following equation:

Death rate (%)=(Number of dead tick/Number of tested tick)×100

As a result, in the treatment with Compounds of Present Invention 26 and 28, the death rate was 100%.

INDUSTRIAL APPLICABILITY

The compound of the present invention has a controlling effect on pests and is useful as an active ingredient of a pest control agent.

The invention claimed is:

1. A compound represented by formula (1) or an N-oxide thereof,

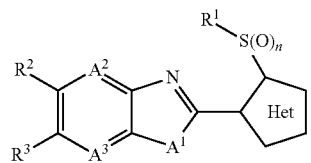

(1)

wherein

Het to which $R^1$—$S(O)_n$ is bonded represents a 5-membered aromatic heterocyclic group represented by the following formula H1, H2, H3 or H4:

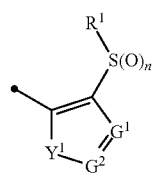

H1

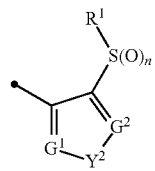

H2

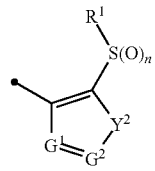

H3

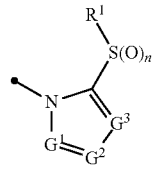

H4 wherein $Y^1$ represents an oxygen atom, a sulfur atom, or $NR^4$;
$Y^2$ represents an oxygen atom, a sulfur atom, or $NR^5$;
$G^1$, $G^2$ and $G^3$ are the same or different and represent $CR^6$ or a nitrogen atom;
$R^1$ represents a C1 to C6 alkyl group optionally having one or more atoms or groups selected from group X, a C2 to C6 alkenyl group optionally having one or more atoms or groups selected from group X, a C2 to C6 alkynyl group optionally having one or more atoms or groups selected from group X, or a C3 to C6 alicyclic hydrocarbon group optionally having one or more atoms or groups selected from group Y;
$R^4$ and $R^6$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^7$, $S(O)_mR^7$, $S(O)_2NR^7R^8$, $NR^7R^8$, $NR^7CO_2R^8$, $NR^7C(O)R^8$, $CO_2R^7$, $C(O)R^8$, $C(O)NR^7R^8$, $SF_5$, a cyano group, a nitro group, a halogen atom, or a hydrogen atom;

$R^5$ represents a C1 to C6 chain hydrocarbon group optionally having one or more atoms or groups selected from group X, a 5- or 6-membered heterocyclic group optionally having one or more atoms or groups selected from group Z, $OR^{12}$, $S(O)_pR^{12}$, $S(O)_2NR^{12}R^{13}$, $NR^{12}R^{13}$, $NR^{12}CO_2R^{13}$, $NR^{12}C(O)R^{13}$, $CO_2R^{12}$, $C(O)R^{12}$, $C(O)NR^{12}R^{13}$, $SF_5$, a cyano group, a nitro group, a halogen atom, or a hydrogen atom;

$R^7$, $R^8$, $R^{12}$ and $R^{13}$ are the same or different and represent a C1 to C6 chain hydrocarbon group optionally having one or more atoms or groups selected from group X, or a hydrogen atom;

each m independently represents 0, 1, or 2;

n represents 0, 1, or 2; and each p independently represents 0, 1, or 2;

wherein, when m is 1 or 2 in $S(O)_mR^7$, $R^7$ does not represent a hydrogen atom, and when p is 1 or 2 in $S(O)_pR^{12}$, $R^{12}$ does not represent a hydrogen atom, $A^1$ represents an oxygen atom, a sulfur atom, or $NR^9$;

$A^2$ represents a nitrogen atom or $CR^{10}$;

$A^3$ represents a nitrogen atom or $CR^{11}$;

$R^2$ and $R^3$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^{14}$, $S(O)_qR^{14}$, $S(O)_2NR^{14}R^{15}$, $NR^{14}R^{15}$, $NR^{14}CO_2R^{15}$, $NR^{14}C(O)R^{15}$, $CO_2R^{14}$, $C(O)R^{15}$, $SF_5$, a cyano group, a nitro group, a halogen atom, or a hydrogen atom;

$R^9$ represents a C1 to C6 chain hydrocarbon group optionally having one or more atoms or groups selected from group X, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $CO_2R^{16}$, $C(O)R^{16}$, a C3 to C6 alicyclic hydrocarbon group optionally having one or more atoms or groups selected from group Y, or a hydrogen atom;

$R^{10}$ and $R^{11}$ are the same or different and represent a C1 to C6 chain hydrocarbon group optionally having one or more halogen atoms, $OR^{17}$, $S(O)_rR^{17}$, $NR^{17}R^{18}$, $CO_2R^{17}$, $C(O)R^{17}$, a cyano group, a nitro group, a halogen atom, or a hydrogen atom;

$R^{14}$, $R^{15}$, $R^{16}$, $R^{17}$ and $R^{18}$ are the same or different and represent a C1 to C6 chain hydrocarbon group optionally having one or more atoms or groups selected from group X, or a hydrogen atom;

each q independently represents 0, 1, or 2; and each r independently represents 0, 1, or 2;

wherein $R^2$ and $R^3$ do not simultaneously represent a hydrogen atom;

when q is 1 or 2 in $S(O)_qR^{14}$, $R^{14}$ does not represent a hydrogen atom;

when r is 1 or 2 in $S(O)_rR^{17}$, $R^{17}$ does not represent a hydrogen atom; and wherein Group X is a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, cyano groups, hydroxy groups, and halogen atoms;

Group Y is a group consisting of C1 to C6 chain hydrocarbon groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, and halogen atoms; and Group Z is a group consisting of C1 to C6 chain hydrocarbon groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C1 to C6 alkylamino groups optionally having one or more halogen atoms, C2 to C8 dialkylamino groups optionally having one or more halogen atoms, halogen atoms, amino groups, cyano groups, $SF_5$, and nitro groups.

2. The compound according to claim 1, wherein $R^1$ is a C1 to C6 alkyl group optionally having one or more atoms or groups selected from group X or a C3 to C6 alicyclic hydrocarbon group optionally having one or more atoms or groups selected from group Y;

$R^2$ and $R^3$ are the same or different and are a C1 to C6 chain hydrocarbon group optionally having one or more atoms or groups selected from group X, $OR^{14}$, $S(O)_qR^{14}$, $SF_5$, a cyano group, a halogen atom, or a hydrogen atom;

$R^4$ and $R^6$ are the same or different and are a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^7$, $S(O)_mR^7$, $SF_5$, a cyano group, a halogen atom, or a hydrogen atom;

$R^5$ is a C1 to C6 chain hydrocarbon group optionally having one or more atoms or groups selected from group X, a 5- or 6-membered heterocyclic group optionally having one or more atoms or groups selected from group Z, $OR^{12}$, $S(O)_pR^{12}$, $SF_5$, a cyano group, a halogen atom, or a hydrogen atom;

$R^9$ is a C1 to C6 chain hydrocarbon group optionally having one or more atoms or groups selected from group X, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), or a C3 to C6 alicyclic hydrocarbon group optionally having one or more atoms or groups selected from group Y;

$R^{10}$ and $R^{11}$ are the same or different and are a C1 to C6 chain hydrocarbon group optionally having one or more halogen atoms, $OR^{17}$, $S(O)_rR^{17}$, $SF_5$, a halogen atom, or a hydrogen atom; and $R^7$, $R^{12}$, $R^{14}$ and $R^{17}$ are the same or different and are a C1 to C6 chain hydrocarbon group optionally having one or more atoms or groups selected from group X.

3. The compound according to claim 1, wherein $R^1$ is a C2 to C6 alkyl group optionally having one or more atoms or groups selected from halogen atoms and a cyclopropyl group (wherein the cyclopropyl group optionally has one or more halogen atoms or one or more C1 to C3 alkyl groups);

$R^2$ is a C1 to C6 alkyl group optionally having one or more halogen atoms, $OR^{14}$, $S(O)_qR^{14}$, $SF_5$, or a halogen atom;

$R^3$ is a hydrogen atom; and $R^{10}$ is a hydrogen atom.

4. The compound according to claim 1, wherein $R^9$ is a C1 to C6 alkyl group optionally having one or more halogen atoms.

5. The compound according to claim 1, wherein $A^2$ is CH; $A^3$ is a nitrogen atom; and $R^3$ is a hydrogen atom.

6. The compound according to claim 1, wherein $R^4$ and $R^6$ are the same or different and are a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, $OR^7$, $S(O)_mR^7$, $SF_5$, a cyano group, a halogen atom, or a hydrogen atom.

7. The compound according to claim 1, wherein Het to which $R^1$—$S(O)_n$ is bonded is H1;

$G^1$ and $G^2$ are the same or different and are $CR^6$; and $R^6$ is a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, or a hydrogen atom.

8. The compound according to claim 1, wherein Het to which $R^1$—$S(O)_n$ is bonded is H1;

$G^1$ is CH; and $G^2$ is $CR^6$, and $CR^6$ is a C1 to C6 alkyl group optionally having one or more halogen atoms or a hydrogen atom.

9. The compound according to claim 1, wherein Het to which $R^1$—$S(O)_n$ is bonded is H2;

$Y^2$ is an oxygen atom or a sulfur atom;

$G^1$ is a nitrogen atom;

$G^2$ is $CR^6$; and $R^6$ is a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, or a hydrogen atom.

10. The compound according to claim 1, wherein Het to which $R^1$—$S(O)_n$ is bonded is H3;

$G^1$ is a nitrogen atom;

$Y^2$ is an oxygen atom or a sulfur atom;

$G^2$ is $CR^6$; and $R^6$ is a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and $SF_5$), a C1 to C6 alkyl group optionally having one or more halogen atoms, or a hydrogen atom.

11. The compound according to claim 1, wherein Het to which $R^1$—$S(O)_n$ is bonded is H3;

$G^1$ is a nitrogen atom;

$Y^2$ is a sulfur atom; and $G^2$ is $CR^6$, and $CR^6$ is a C1 to C6 alkyl group optionally having one or more halogen atoms, or a hydrogen atom.

12. The compound according to claim 1,
wherein Het to which $R^1$—S(O)$_n$ is bonded is H4;
$G^2$ and $G^3$ are the same or different and are $CR^6$; and
$R^6$ is a phenyl group (wherein the phenyl group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and SF$_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C3 alkoxy groups optionally having one or more halogen atoms, C1 to C3 alkylthio groups optionally having one or more halogen atoms, C1 to C3 alkylsulfinyl groups optionally having one or more halogen atoms, C1 to C3 alkylsulfonyl groups optionally having one or more halogen atoms, halogen atoms and SF$_5$), a C1 to C6 alkyl group optionally having one or more halogen atoms, or a hydrogen atom.

13. The compound according to claim 1, wherein $A^2$ is $CR^{10}$; and $R^6$ is a hydrogen atom.

14. A compound represented by formula (2-2) or an N-oxide thereof,

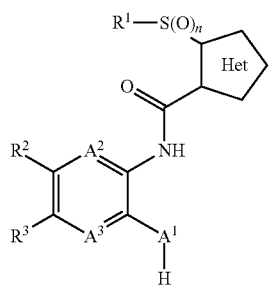

(2-2)

wherein
Het to which $R^1$—S(O)$_n$ is bonded represents a 5-membered aromatic heterocyclic group represented by the following formula H1, H2, H3 or H4:

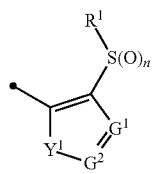

H1

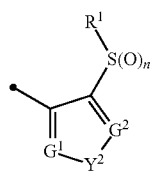

H2

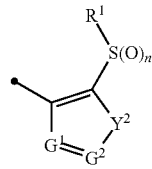

H3

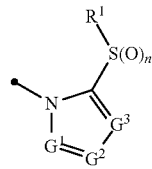

H4 wherein $Y^1$ represents an oxygen atom, a sulfur atom, or $NR^4$;

$Y^2$ represents an oxygen atom, a sulfur atom, or $NR^5$;

$G^1$, $G^2$ and $G^3$ are the same or different and represent $CR^6$ or a nitrogen atom;

$R^1$ represents a C1 to C6 alkyl group optionally having one or more atoms or groups selected from group X, a C2 to C6 alkenyl group optionally having one or more atoms or groups selected from group X, a C2 to C6 alkynyl group optionally having one or more atoms or groups selected from group X, or a C3 to C6 alicyclic hydrocarbon group optionally having one or more atoms or groups selected from group Y;

$R^4$ and $R^6$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, OR$^7$, S(O)$_m$R$^7$, S(O)$_2$NR$^7$R$^8$, NR$^7$R$^8$, NR$^7$CO$_2$R$^8$, NR$^7$C(O)R$^8$, CO$_2$R$^7$, C(O)R$^8$, C(O)NR$^7$R$^8$, SF$_5$, a cyano group, a nitro group, a halogen atom, or a hydrogen atom;

$R^5$ represents a C1 to C6 chain hydrocarbon group optionally having one or more atoms or groups selected from group X, a 5- or 6-membered heterocyclic group optionally having one or more atoms or groups selected from group Z, OR$^{12}$, S(O)$_p$R$^{12}$, S(O)$_2$NR$^{12}$R$^{13}$, NR$^{12}$R$^{13}$, NR$^{12}$CO$_2$R$^{13}$, NR$^{12}$C(O)R$^{13}$, CO$_2$R$^{12}$, C(O)R$^{12}$, C(O)NR$^{12}$R$^{13}$, SF$_5$, a cyano group, a nitro group, a halogen atom, or a hydrogen atom;

$R^7$, $R^8$, $R^{12}$ and $R^{13}$ are the same or different and represent a C1 to C6 chain hydrocarbon group optionally having one or more atoms or groups selected from group X, or a hydrogen atom;

each m independently represents 0, 1, or 2;
n represents 0, 1, or 2, and
each p independently represents 0, 1, or 2;
wherein, when m is 1 or 2 in S(O)$_m$R$^7$, R$^7$ does not represent a hydrogen atom, and when p is 1 or 2 in S(O)$_p$R$^{12}$, R$^{12}$ does not represent a hydrogen atom, $A^1$ represents an oxygen atom, a sulfur atom, or $NR^9$;
$A^2$ represents a nitrogen atom or $C^{10}$;
$A^3$ represents a nitrogen atom or $CR^{11}$;
$R^2$ and $R^3$ are the same or different and represent a C1 to C6 chain hydrocarbon group optionally having one or more atoms or groups selected from group X, a phenyl group optionally having one or more atoms or groups selected from group Z, a 5- or 6-membered heterocyclic group optionally having one or more atoms or groups selected from group Z, $OR^{14}$, $S(O)_qR^{14}$, $S(O)_2NR^{14}R^{15}$, $NR^{14}R^{15}$, $NR^{14}CO_2R^{15}$, $NR^{14}C(O)R^{15}$, $CO_2R^{14}$, $C(O)R^{15}$, $SF_5$, a cyano group, a nitro group, a halogen atom, or a hydrogen atom;

$R^9$ represents a C1 to C6 chain hydrocarbon group optionally having one or more atoms or groups selected from group X, a C1 to C6 chain hydrocarbon group having one phenyl group (wherein the phenyl group optionally has one or more atoms or groups selected from group Z), a C1 to C6 chain hydrocarbon group having one 5- or 6-membered heterocyclic group (wherein the 5- or 6-membered heterocyclic group optionally has one or more atoms or groups selected from group Z), $CO_2R^{16}$, $C(O)R^{16}$, a C3 to C6 alicyclic hydrocarbon group optionally having one or more atoms or groups selected from group Y, or a hydrogen atom;

$R^{10}$ and $R^{11}$ are the same or different and represent a C1 to C6 chain hydrocarbon group optionally having one or more halogen atoms, $OR^{17}$, $S(O)_rR^{17}$, $NR^{17}R^{18}$, $CO_2R^{17}$, $C(O)R^{17}$, a cyano group, a nitro group, a halogen atom, or a hydrogen atom;

$R^{14}$, $R^{15}$, $R^{16}$, $R^{17}$ and $R^{18}$ are the same or different and represent a C1 to C6 chain hydrocarbon group optionally having one or more atoms or groups selected from group X, or a hydrogen atom;

each q independently represents 0, 1, or 2; and each r independently represents 0, 1, or 2, wherein $R^2$ and $R^3$ do not simultaneously represent a hydrogen atom;

when q is 1 or 2 in $S(O)_qR^{14}$, $R^{14}$ does not represent a hydrogen atom; and when r is 1 or 2 in $S(O)_rR^{17}$, $R^{17}$ does not represent a hydrogen atom; and wherein Group X is a group consisting of C1 to C6 alkoxy groups optionally having one or more halogen atoms, C2 to C6 alkenyloxy groups optionally having one or more halogen atoms, C2 to C6 alkynyloxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C3 to C6 cycloalkyl groups optionally having one or more halogen atoms or one or more C1 to C3 alkyl groups, cyano groups, hydroxy groups, and halogen atoms;

Group Y is a group consisting of C1 to C6 chain hydrocarbon groups optionally having one or more halogen atoms, C1 to C6 alkoxy groups optionally having one or more halogen atoms, C2 to C6 alkenyloxy groups optionally having one or more halogen atoms, C2 to C6 alkynyloxy groups optionally having one or more halogen atoms, and halogen atoms; and Group Z is a group consisting of C1 to C6 chain hydrocarbon groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, C2 to C6 alkylcarbonyl groups optionally having one or more halogen atoms, C2 to C6 alkoxycarbonyl groups optionally having one or more halogen atoms, C1 to C6 alkylamino groups optionally having one or more halogen atoms, C2 to C8 dialkylamino groups optionally having one or more halogen atoms, halogen atoms, amino groups, cyano groups, $SF_5$, and nitro groups.

15. The compound according to claim 14, wherein $R^1$ represents a C2 to C6 alkyl group optionally having one or more atoms or groups selected from halogen atoms and a cyclopropyl group (wherein the cyclopropyl group optionally has one or more halogen atoms or one or more C1 to C3 alkyl groups);

$R^4$ and $R^6$ are the same or different and represent a phenyl group (wherein the phenyl group optionally has one or more atoms or groups selected from C1 to C3 alkyl groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, halogen atoms and $SF_5$), a 5- or 6-membered heterocyclic group (wherein the 5- or 6-membered heterocyclic group optionally has one or more atoms or groups selected from C1 to C3 alkyl groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, halogen atoms and $SF_5$), or a C1 to C6 alkyl group optionally having one or more halogen atoms;

$R^5$ represents a 5- or 6-membered heterocyclic group (wherein the 5- or 6-membered heterocyclic group optionally has one or more atoms or groups selected from C1 to C3 alkyl groups optionally having one or more halogen atoms, C1 to C6 alkoxy groups optionally having one or more halogen atoms, C1 to C6 alkylthio groups optionally having one or more halogen atoms, C1 to C6 alkylsulfinyl groups optionally having one or more halogen atoms, C1 to C6 alkylsulfonyl groups optionally having one or more halogen atoms, halogen atoms and $SF_5$) or a C1 to C6 alkyl group optionally having one or more halogen atoms;

$A^2$ represents CH;

$R^2$ and $R^{11}$ are the same or different and represent a C1 to C6 alkyl group optionally having one or more halogen atoms, $OR^{14}$, $S(O)_qR^{14}$, $SF_5$, or a halogen atom;

$R^9$ and $R^{14}$ are the same or different and represent a C1 to C6 alkyl group optionally having one or more halogen atoms; and $R^3$ represents a hydrogen atom;

wherein, when q is 1 or 2 in $S(O)_qR^{14}$, $R^{14}$ does not represent a hydrogen atom.

16. A pest control agent comprising the compound as defined in claim 1, and an inert carrier.

17. A method for controlling pests comprising a step of applying an effective amount of the compound as defined in claim 1 to a pest or pest habitats.

* * * * *